(12) United States Patent
Zhou et al.

(10) Patent No.: US 9,139,868 B2
(45) Date of Patent: Sep. 22, 2015

(54) SILICON AND GERMANIUM DYES FOR USE IN GENETIC IDENTITY

(71) Applicant: PROMEGA CORPORATION, Madison, WI (US)

(72) Inventors: Wenhui Zhou, Santa Maria, CA (US); Poncho Meisenheimer, San Luis Obispo, CA (US); Min Zhou, Santa Maria, CA (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

(21) Appl. No.: 14/210,818

(22) Filed: Mar. 14, 2014

(65) Prior Publication Data

US 2014/0272990 A1    Sep. 18, 2014

Related U.S. Application Data

(60) Provisional application No. 61/789,199, filed on Mar. 15, 2013.

(51) Int. Cl.
| | |
|---|---|
| *C12Q 1/68* | (2006.01) |
| *C07D 311/78* | (2006.01) |
| *C09B 11/24* | (2006.01) |
| *G01N 33/58* | (2006.01) |
| *G01N 21/64* | (2006.01) |
| *C07H 19/04* | (2006.01) |

(52) U.S. Cl.
CPC .............. *C12Q 1/6818* (2013.01); *C09B 11/24* (2013.01); *G01N 21/6456* (2013.01); *G01N 33/582* (2013.01)

(58) Field of Classification Search
CPC .............................. C12Q 1/6818; C09B 11/24
USPC ....... 435/6.1; 536/26.6; 422/430; 549/16, 24, 549/214, 223
See application file for complete search history.

(56) References Cited

U.S. PATENT DOCUMENTS

| | | | |
|---|---|---|---|
| 4,997,928 | A | 3/1991 | Hobbs, Jr. |
| 5,171,534 | A | 12/1992 | Smith et al. |
| 5,332,666 | A | 7/1994 | Probert et al. |
| 2009/0263843 | A1 | 10/2009 | Anderson et al. |
| 2010/0173384 | A1 | 7/2010 | Johnsson et al. |
| 2012/0237961 | A1 | 9/2012 | Gautier et al. |
| 2013/0317207 | A1 | 11/2013 | Kirkland et al. |

FOREIGN PATENT DOCUMENTS

WO            WO 94/05688            3/1994

OTHER PUBLICATIONS

Yuichiro Koide et al: "Development of NIR Fluorescent Dyes Based on Si-rhodamine for in Vivo Imaging", Journal of the American Chemical Society, vol. 134, No. 11, Mar. 21, 2012, pp. 5029-5031.
PCT International Search Report and Written Opinion for Application No. PCT/US2014/027179 dated Jul. 28, 2014 (12 pages).
Yuichiro Koide et al: "Development of an Si-Rhodamine-Based Far-Red to Near-Infrared Fluorescence Probe Selective for Hypochlorous Acid and Its Applications for Biological Imaging", Journal of the American Chemical Society, vol. 133, No. 15, Apr. 20, 2011, pp. 5680-5682.
Dietrich et al: "Fluorescence Resonance Energy Transfer (FRET) and Competing Processes in Donor-Acceptor Substituted DNA Strands: A Comparative Study of Ensemble and Singlemolecule Data", Reviews in Molecular Biotechnology, Elsevier, Amsterdam, NL, vol. 82, No. 3, Jan. 1, 2002, pp. 211-231.
Paquette, Leo A.; "Principles of Modern Heterocyclic Chemistry" (W.A. Benjamin, New York, 1968), particularly Chapters 1, 3, 4, 6, 7, and 9.
Weissberger, "The Chemistry of Heterocyclic Compounds, A Series of Monographs" (John Wiley & Sons, New York, 1950 to present), in particular vols. 13, 14, 16, 19, and 28.
International Union of Pure and Applied Chemistry, "Definitive Rules for Nomenclature of Organic Chemistry" J. Am. Chem. Soc. 1957, vol. 82, 5545-5574.
Wittung et al., "DNA-like double helix formed by peptide nucleic acid" Nature, 368:561 (1994).
Xia, Z and Rao, J. "Biosensing and imaging on bioluminescence resonance energy transfer," 2009. Curr. Opin. Biotech 20: 37-44.

*Primary Examiner* — Jezia Riley
(74) *Attorney, Agent, or Firm* — Michael Best & Friedrich LLP

(57) ABSTRACT

Si- and Ge-based dyes and methods of using same.

6 Claims, 37 Drawing Sheets

Figure 1

Dye Set

Name: ETTOM3885with4686J3nuc

Spectral Calibration

Dye Set: ETTOM3885  Chemistry: matrixStandard
Calibration Date: 07-Jan-2012 09:31:22 AM

| Capillary | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| Run 1 | | | | | | | | | | | | | | | | | | | | | | | | |
| Run 2 | | | | | | | | | | | | | | | | | | | | | | | | |
| Run 3 | | | | | | | | | | | | | | | | | | | | | | | | |
| Overall | | | | | | | | | | | | | | | | | | | | | | | | |

Legend: ■ Passed  ■ Failed  * Borrowed  ☐ Not Calibrated

Capillary Run Data

| Capillary | Pass/Fail/Borrowed | qValue | Condition Number | Peak 1 | Peak 2 | Peak 3 | Peak 4 | Peak 5 | Peak 6 |
|---|---|---|---|---|---|---|---|---|---|
| 1 | Pass | 0.993 | 5.324 | 20105 | 10341 | 15003 | 34416 | 20175 | 6550 |
| 2 | Pass | 0.993 | 5.316 | 23905 | 11988 | 20850 | 46442 | 26267 | 9346 |
| 3 | Pass | 0.991 | 5.320 | 8725 | 4421 | 7157 | 17063 | 9661 | 3229 |
| 4 | Pass | 0.992 | 5.270 | 14547 | 7338 | 10586 | 24527 | 14506 | 4773 |
| 5 | Pass | 0.993 | 5.358 | 27512 | 14367 | 20569 | 48180 | 29050 | 9175 |
| 6 | Pass | 0.992 | 5.365 | 32807 | 16551 | 27596 | 60490 | 35612 | 12524 |
| 7 | Borrowed Cap 8 | 0.992 | 5.268 | 27106 | 13133 | 18878 | 43861 | 26584 | 8590 |
| 8 | Pass | 0.992 | 5.268 | 27106 | 13133 | 18878 | 43861 | 26584 | 8590 |
| 9 | Borrowed Cap 8 | 0.992 | 5.268 | 27106 | 13133 | 18878 | 43861 | 26584 | 8590 |

Figure 5. 6 FAM with 3 nucleotide spacer and #4688 in the G5 spectral calibration on the 3500 instrument.

Reaction and condition: (I) *sec*-BuLi, THF, -78°C; Cl$_2$Z(R$_3$)$_2$, -78°C to rt; (IIa) chlorinil/DCM, rt; (IIb) KMnO$_4$, acetone, rt; (III) chlorinil/NaHCO$_3$/acetone/DCM, rt; (IV) sec-BuLi, THF, -78°C to rt; (Va) TFA/DCM, 2% TIPS; (Vb) Pd(PPh$_3$)4, 1,3-dimethylbarbituric acid, DCM, 45°C; (VI) TSTU/DIPEA/DMF, rt.

Reaction and condition: (IV) sec-BuLi, THF, -78°C to rt; (Vc) 2NHCl/ACN reflux or 2N HCl/ ACN, 80oC, microwave; (Vb) Pd(PPh$_3$)4, 1,3-dimethylbarbituric acid, DCM, 45°C; (VI) TSTU/DIPEA/DMF, rt.

Figure 12. Absorbance and emission of Si/Ge xanthene dyes in TE-4 at pH 7.4

|  | Absorbance (nm) | Emission(nm) | Quantum Yields |
|---|---|---|---|
| PBI 4679 | 647 | 666 | 0.5 |
| PBI 4687 | 647 | 663 | 0.5 |
| PBI 4757 | 662 | 679 | 0.5 |
| PBI 5119 | 653 | 666 | 0.76 |
| PBI 4911 | 634 | 652 | 0.5 |
| PBI 4939 | 641 | 649 | 0.5 |
| PBI 4988 | 643 | 657 | 0.6 |
| PBI 4990 | 639 | 659 | 0.2 |
| PBI 4771 | 646 | 662 | 0.34 |
| PBI 4876 | 615 | 631 | 2xTom dye |
| PBI 4914 | 592 | 606 | 0.58 |
| PBI 4754 | 645 | 664 | 0.59 |
| PBI 4964 | 644 | 663 | 0.6 |
| PBI 4977 | 643 | 661 | 0.6 |
| PBI 4984 | 642 | 659 | 0.58 |
| PBI 4986 | 652 | 659 | 0.6 |
| PBI 5117 | 650 | 666 | 0.61 |
| PBI 5152 | 632 | 652 | 0.5 |
| PBI 5151 | 630 | 650 | 0.53 |
| PBI 5155 | 606 | 622 | 0.78 |

CC3 TTTT WZ88 ILS

CC3 TTTT WZ88 ILS
Fluorescein Channel Included

CC3 TTTT WZ88 ILS
JOE Channel Included

CC3 TTTT WZ88 ILS
ET-TMR Channel Included

CC3 TTTT WZ88 ILS
ET-CXR Channel Included

CC3 TTTT WZ88 ILS
ET-TOM Channel Included

6TMR TTTT WZ88 ILS

6TMR TTTT WZ88 ILS
Fluorescein Included

6TMR TTTT WZ88 ILS
JOE Channel Included

6TMR TTTT WZ88 ILS
ET-TMR Channel Included

6TMR TTTT WZ88 ILS
ET-CXR Channel Included

6TMR TTTT WZ88 ILS
ET-TOM Channel Included

CC3 TTTT WZ88 ILS
CC3 TTTT WZ88 ILS was diluted 1 to 40 in TE$^{-4}$ before starting the freeze – thaws CC3 TTTT WZ88 ILS
CC3 TTTT WZ88 ILS was diluted 1 to 40 in TE⁻⁴ before starting the freeze - thaws CC3 TTTT WZ88 ILS
CC3 TTTT WZ88 ILS was diluted 1 to 40 in TE$^{-4}$ before starting the freeze - thaws

CC3 TTTT WZ88 ILS

CC3 TTTT WZ88 ILS
CC3 TTTT WZ88 ILS was put through freeze – thaws and then diluted 1 to 40 in TE$^{-4}$ CC3 TTTT WZ88 ILS
CC3 TTTT WZ88 ILS was put through freeze – thaws and then diluted 1 to 40 in TE$^{-4}$ 6TMR TTTT WZ88 ILS
6TMR TTTT WZ88 ILS was diluted 1 to 40 in TE$^{-4}$ before starting the freeze - thaws 6TMR TTTT WZ88 ILS
6TMR TTTT WZ88 ILS was diluted 1 to 40 in TE$^{-4}$ before starting the freeze - thaws 6TMR TTTT WZ88 ILS
6TMR TTTT WZ88 ILS was diluted 1 to 40 in TE$^{-4}$ before starting the freeze - thaws 6TMR TTTT WZ88 ILS
6TMR TTTT WZ88 ILS was put through freeze – thaws and then diluted 1 to 40 in TE$^{-4}$ 6TMR TTTT WZ88 ILS
6TMR TTTT WZ88 ILS was put through freeze – thaws and then diluted 1 to 40 in TE$^{-4}$

6TMR TTTT WZ88 ILS

SILICON AND GERMANIUM DYES FOR USE IN GENETIC IDENTITY

CROSS REFERENCE TO RELATED APPLICATIONS

This application claims priority to U.S. Provisional Application No. 61/789,199, filed Mar. 15, 2013, which is incorporated herein by reference in its entirety.

BACKGROUND

Fluorescent dyes are widely used in biological research and medical diagnostics. Fluorescent dyes tend to be superior to conventional techniques because they are less expensive, less toxic and can generally be detected with sufficient sensitivity. A diversity of fluorescent dyes with a distinguishable color range has made it more practical to perform multiplexed assays capable of detecting multiple biologic targets at the same time.

Further improvement in the properties of the dyes is needed in order to meet the increasing demands of new instruments and new biological applications. In particular, additional strategies to allow for fine-tuning of the wave-lengths of the dyes for maximal signal detection and to provide additional colors are needed.

SUMMARY

In some aspects, the invention provides a method of detecting the presence of a nucleic acid polymer in a sample comprising contacting a sample suspected of containing a nucleic acid polymer with a composition comprising a conjugate comprising a compound of Formula (I) and an oligonucleotide; and detecting the presence or amount of the compound in the sample, wherein the compound of formula (I) is a component in an ET cassette In other aspects, the invention provides a method of detecting the presence of a nucleic acid polymer in a sample comprising contacting a sample suspected of containing a nucleic acid polymer with a composition comprising a conjugate comprising a compound of Formula (II) and an oligonucleotide; and detecting the presence or amount of the compound in the sample; wherein the compound of formula (II) is a component in an ET cassette and In some aspects, the invention provides a compound selected from the group consisting of:

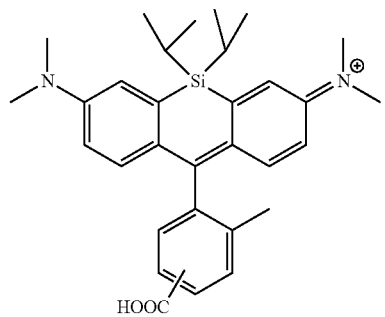

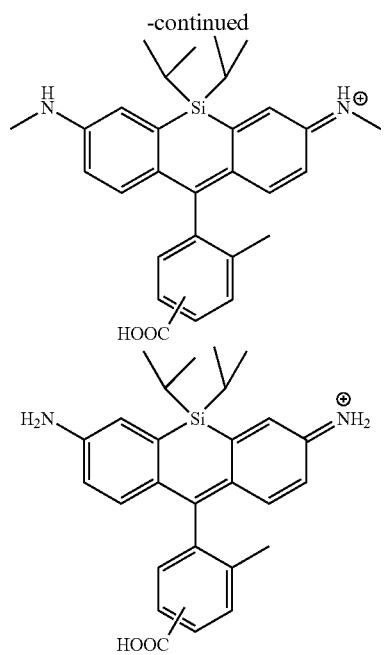

In other aspects, the invention provides a kit comprising a compound according to formula (I) or (II) in an ET cassette, at least one locus-specific primer, and instructions for use.

In some aspects, the invention provides a method of detecting the presence of a nucleic acid polymer in a sample comprising: contacting a sample suspected of containing a nucleic acid polymer with a composition comprising a conjugate comprising a compound according to the present invention and an oligonucleotide; and detecting the presence or amount of the compound in the sample.

In some aspects, the invention provides a method of monitoring binding to a target of interest, e.g., a drug target, comprising contacting a sample comprising a fusion protein comprising the target of interest with a small molecule or biomolecule conjugated to a dye described herein; and detecting binding of the small molecule conjugate to the target of interest. In some aspects, the fusion protein comprises a luciferase protein fused to the target of interest. In other aspects, the fusion protein comprises a fluorescent protein fused to the target of interest. In some aspects, wherein the fusion protein comprises a luciferase protein, binding is detected by bioluminescence resonance energy transfer (BRET). In some aspects, wherein the fusion protein comprises a fluorescent protein, binding is detected by fluorescent resonance energy transfer (FRET). In some aspects, the sample comprises a cell expressing the fusion protein.

In other aspects, the invention provides a kit comprising a compound according to the present invention or a labeled small molecule or biomolecule according to the present invention. In some aspects, the kit comprises a labeled biomolecule or labeled small molecule, e.g., drug or drug compound. In some aspects, the kit further comprises cells expressing a fusion protein comprising a protein or target of interest. In other aspects, the kit further comprises a vector for expressing a fusion protein comprising a protein or target of interest.

Other aspects of the invention will become apparent by consideration of the detailed description and accompanying drawings.

BRIEF DESCRIPTION OF THE DRAWINGS

FIG. 1 illustrates a spectral calibration run with PBI-4686 with an excellent Q value of 0.99.

FIG. 12 illustrates absorbance and emission spectral properties of Si-/Ge-dyes in aqueous buffer.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

In some embodiments, the invention provides a new use for a new class of fluorophores which are rhodamine-based structures with central oxygen bridge atom replaced by silicon or germanium. These dyes have high extinction coefficient and high quantum yield with tunable absorption and emission wavelength. (See FIG. 12). The general structure of new Si-rhodamine derivatives is exemplarily shown below:

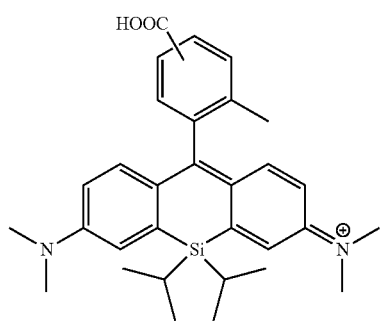

The important feature of these fluorophores is the presence of di-isopropyl at Si of the xanthene ring, which improves the energy transfer (ET) efficiency of an ET cassette in the electrophoresis capillary matrix, resulting in the signal of amplicons passing instrument calibration and also improving dye stability, allowing labeled oligos to be stored in aqueous buffers for reasonably long periods of time (See FIGS. 3-8).

Among other things, the invention provides a new use for silica/germanium dyes in DNA typing or analysis of short tandem repeats (STRs) using multiplex PCR. These highly efficient energy transfer silica/germanium acceptor dyes, with tunable absorbance and emission wavelength, and are compatible with different donor dyes, have great potential benefit of being used in multiplex STR analysis systems and kits at the desired color channels with minimal laser excitation sources. (See FIGS. 3-8).

The Foster energy transfer (FRET) refers to the non-radiative transfer of an electronic excitation optically induced electronic coherence on the donor are resonant with electronic energy gap of the acceptor. The FRET efficiency depends on the following physical parameters: (1) spectral overlap of donor emission spectrum and acceptor absorption spectrum; (2) the relative orientation of the donor emission dipole moment and the acceptor absorption dipole moment; and (3) the distance between the donor and acceptor. (See FIG. 11).

Figure 9:
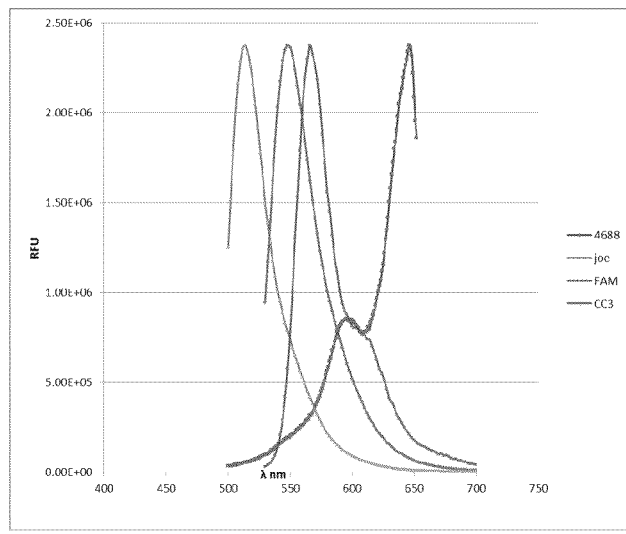
FIG. 9 illustrates the overlap of different donor dye absorbance and emission spectra of Si-rhodamine PBI-4688 dye.

Although the absorbance spectra of silica and germanium dyes have much less overlap with the emission spectra of FAM or JOE compared to TMR, ROX and other known fluorescent dyes, such as those disclosed in U.S. patent application Ser. No. 13/682,589, the amplicon signals from labeled primers of interest comprising silica and germanium dyes of the present invention are much brighter than other FAM/JOE-dye ET cassettes. (See FIGS. 3 and 9).

The relative orientation of the donor emission dipole moment and the acceptor absorption dipole moment implies the energy transfer is typically efficient between the same types of molecules. However, the silica/germanium dyes of the present invention were found to be compatible as acceptor dyes with different donor dyes such as FAM, JOE, CC3 and Dyomics 485L (See FIGS. 3-8).

Increased multiplexing of dye labels allows for shorter oligo primers and, consequently, faster analysis times and improved analysis of damaged (fragmented) DNA samples. Since STR analysis instruments have fixed emission lasers (or diodes), increasing the number of multiplex dyes is limited by the identification of a stable and efficient ET pairs. The robust ET acceptor properties of the silica/germanium dyes of the present invention improves the ability to create STR analysis systems and kits with increased multiplexing capabilities.

DEFINITIONS

As used herein, the following terms and expressions have the indicated meanings. It will be appreciated that the compounds of the present invention contain asymmetrically substituted carbon atoms and may be isolated in optically active or racemic forms. It is well known in the art how to prepare optically active forms such as by resolution of racemic forms or by synthesis from optically active starting materials. All chiral, diastereomeric, racemic forms and all geometric isomeric forms of a structure are part of this invention.

Specific values listed below for radicals, substituents, and ranges, are for illustration only; they do not exclude other defined values or other values within defined ranges for the radicals and substituents.

As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, the suitable indicated groups can include, e.g., —X, —R, —O⁻, —OR, —SR, —S⁻, —NR$_2$, —NR$_3$, =NR$_3$, —CX$_3$, —CN, —OCN, —SCN, —N=C=O, —NCS, —NO, —NO$_2$, =N$_2$, —N$_3$, NC(=O)R, —C(=O)R, —C(=O)NRR, —S(=O)$_2$O⁻, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=O)(O)$_2$, —P(=O)(OH)$_2$, —C(=O)R, —C(=O)X, —C(S)R, —C(O)OR, —C(O)O, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is oxo (=O) or thioxo (=S), or the like, then two hydrogen atoms on the substituted atom are replaced.

As used herein, the term "alkyl" refers to a branched, unbranched, or cyclic hydrocarbon having, for example, from 1 to 30 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

The term "alkenyl" refers to a monoradical branched or unbranched partially unsaturated hydrocarbon chain (i.e. a carbon-carbon, sp$^2$ double bond). In some embodiments, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In some embodiments, the alkynyl group can have from 2 to 10 carbon atoms, or 2 to 6 carbon atoms. In other embodiments, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In some embodiments, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

As used herein, "aryl" or "Ar" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 30 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In some embodiments, the haloalkyl can be substituted with 1, 2, 3, 4, or 5 halo groups. In other embodiments, the haloalkyl can be substituted with 1, 2, or 3 halo groups. The term haloalkyl also include perfluoroalkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2-20 carbon atoms in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In some embodiments, the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1$-$C_6)$alkylaryl. In other embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; Principles of Modern Heterocyclic Chemistry (W. A. Benjamin, New York, 1968), particularly Chapters 1, 3, 4, 6, 7, and 9; The Chemistry of Heterocyclic Compounds, A Series of Monographs" (John Wiley & Sons, New York, 1950 to present), in particular Volumes 13, 14, 16, 19, and 28; and *J. Am. Chem. Soc.* 1960, 82, 5566. In some embodiments, "heterocycle" includes a "carbocycle" as defined herein, wherein one or more (e.g. 1, 2, 3, or 4) carbon atoms have been replaced with a heteroatom (e.g. O, N, or S).

Examples of heterocycles, by way of example and not limitation, include, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In some embodiments, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "amino" refers to —NH$_2$. The amino group can be optionally substituted as defined herein for the term "substituted".

The term "alkylamino" refers to —NR$_2$, wherein at least one R is alkyl and the second R is alkyl or hydrogen.

The term "acylamino" refers to N(R)C(=O)R, wherein each R is independently hydrogen, alkyl, or aryl.

The term "hydroxyalkyl" refers to an alkyl group substituted by —OH.

The term "alkylcarboxylic acid" refers to an alkyl group substituted by —COOH.

The term "interrupted" indicates that another group is inserted between two adjacent carbon atoms (and the hydrogen atoms to which they are attached (e.g., methyl (CH$_3$), methylene (CH$_2$) or methine (CH))) of a particular carbon chain being referred to in the expression using the term "interrupted, provided that each of the indicated atoms' normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl (SO$_2$). Alkyl groups can be interrupted by one ore more (e.g., 1, 2, 3, 4, 5, or about 6) of the aforementioned suitable groups. The site of interruption can also be between a carbon atom of an alkyl group and a carbon atom to which the alkyl group is attached.

An "effective amount" generally means an amount that provides a desired effect, for example, an amount sufficient to bring about a reaction.

As used herein, "contacting" refers to the act of touching, making contact, or of bringing to immediate or close proximity, including at the molecular level, for example, to bring about a chemical reaction or physical change, e.g., in a solution, cell, or other reaction mixture.

The term "amino acid" includes a residue of a natural amino acid in D or L form as well as unnatural amino acids (e.g. phosphoserine, phosphothreonine, phosphotyrosine, hydroxyproline, gamma-carboxyglutamate, hippuric acid, octahydroindole-2-carboxylic acid, statine, 1,2,3,4-tetrahydroisoquinoline-3-carboxylic acid, penicillamine, ornithine, citruline, alpha-methylalanine, para-benzolylphenylalanine, phenylglycine, propargylglycine, sacrosine, and tert-butylglycine). The term also comprises natural and unnatural amino acids bearing a conventional amino protecting group (e.g. acetyl or benzoylcarboyl), as well as natural and unnatural amino acids protected at the carboxy terminus (e.g. as ($C_{1-6}$ alkyl, phenyl or benzyl ester or amide; or as an alpha-methylbenzyl amide). Other suitable amino and carboxy protecting groups are known to those skilled in the art. (See, e.g., Greene, T. W.; Wutz, P. G. M. *Protecting Groups in Organic Synthesis*, 2$^{nd}$ edition, John Wiley & Sons, Inc., New York (1991) and references cited therein).

The term "peptide" refers to a sequence of 2 to 35 amino acids or peptidyl residues. The sequence may be linear or cyclic. For example, a cyclic peptide can be prepared or may result for the formation of a disulfide bridge between two cysteine residues in a sequence. Suitably, a peptide comprises 3 to 20, or 5 to 15 amino acids. Peptide sequences specifically recited herein are written with the amino terminus on the left and the carboxy terminus on the right.

The term "reactive group" refers to an activated ester of a carboxylic acid, an amine, an alcohol, a sulfonyl halide, a mercaptan, a boronate, a phosphoramidite, an isocyanate, a haloacetamide, an aldehyde, an azide, an acyl nitrile, a photoactivateable group or an alkyl halide.

The term "conjugated substance" refers to a covalently bound substance such as a surface (e.g. a bead, solid support, resin, particle, or an assay plate), biological molecule or biomolecule (e.g., proteins, nucleotides, polynucleotides including DNA and RNA, enzyme substrates, antibodies, nanobodies, polypeptides, polypeptide-based toxins, amino acids, lipids, carbohydrates, haptens, ion-complexing agents, such as metal chelators, microparticles, synthetic or natural polymers, cells, viruses, other fluorescent molecules or surfaces), small molecules (e.g., drugs, drug compounds), or other moieties of interest, e.g. a chloroalkane or a cyanobenzothiazole. Other suitable conjugated substances include, but are not limited to, a lanthanide-complexing group; a nickel-complexing group; a cobalt-complexing group; ethylenediamine tetraacetic acid; nitriloacetic acid; a nucleotide; a substrate of an enzyme; an inhibitor of an enzyme, preferably an irreversible inhibitor of an enzyme forming a covalent bond with an enzyme; an agonist of a receptor; a ligand that binds with a KD of at least 10 µM to a nucleic acid; a ligand that binds with a KD of at least 10 µM to a protein; a substrate of SNAP-tag; a substrate of CLIP-tag; a substrate of Halo-tag, a ligand binding to dihydrofolate reductase; methotrexate; trimethoprim; a substrate of biotin ligase; a substrate of phosphopantetheine transferase; a substrate of lipoic acid ligase; biotin; a ligand binding to streptavidin, avidin or neutravidin; a cofactor of an enzyme; a hormone; a toxin; a fluorophore; a nucleic acid polymer; a hapten; an antigen; a drug; a lipid; a lipid assembly; a non-biological organic polymer; a polymeric microparticle; an animal cell a plant cell; a bacterium, a yeast; a virus; and a protist.

A "tracer" is a type of conjugated substance where a dye of the present invention is conjugated to a substance as defined above, possibly through a linker.

The term "traceless linker" or "self-immolative linker" refers to a linker wherein cleavage of a conjugated substance from the linker results in spontaneous cleavage of the linker from the dye to release the unbound dye. Exemplary traceless linkers include:

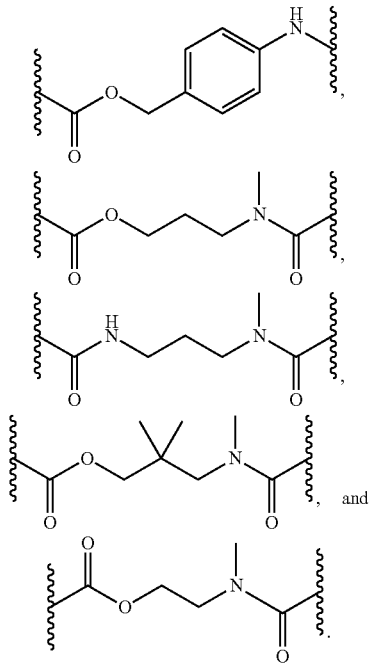

As would be recognized by one of ordinary skill in the art, further variations in linker length and substitution are possible.

The term "ET cassette" refers to any pair of dyes which transfer excited states from the donor to the acceptor.

Methods of Use

Among other things, the dyes of the present invention may be used in any way that other near-IR fluorescent dyes are used. Some examples are discussed below.

The dyes of the present invention provide an effective tool for covalently labeling substances for a wide variety of applications. Labeling allows one to study interactions involving biomolecules such as proteins, glycoproteins, nucleic acids and lipids, as well as small molecules, e.g., drugs or drug compounds, inorganic chemicals or any combinations thereof. The interactions may be studied in cell-free biological systems, in cellular systems or in vivo. Analyzing the various interactions is often a significant part of scientific research and development, drug design, screening and optimization, phylogenetic classification, genotyping individuals, parental and forensic identification, environmental studies, diagnosis, prognosis, and/or treatment of disease conditions.

In some aspects of the invention, the conjugates of the invention are used to label a sample so that the sample can be identified or quantitated. For instance, such conjugates may be added as part of an assay for a biological target analyte or as a detectable tracer element in a biological or non-biological fluid.

The sample may be obtained directly from biological materials, e.g., a wash from a solid material (organic or inorganic), a medium in which cells have been cultured, a cell lysate, a buffer solution in which cells have been placed for evaluation, or physiological sources, e.g., blood, plasma, serum, urine, etc. When the sample comprises cells, the cells are optionally single cells, including microorganisms, or multiple cells associated with other cells in two or three dimensions, including multicellular organisms, embryos, tissues, biopsies, filaments, biofilms, and the like. When the sample comprises cells, the cells may be lysed, e.g., a cell lysate, or whole cells. The cells may also be in an animal, i.e, the dyes of the present invention may be used for in vivo imaging.

Alternatively, the sample is a solid, optionally a smear or scrape or a retentate removed from a liquid or vapor by filtration. In some aspects of the invention, the sample is obtained from a biological fluid, including separated or unfiltered physiological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot.

In other embodiments, the sample is present on or in a solid or semi-solid matrix. In some aspects of the invention, the matrix is a membrane. In other aspects, the matrix is an electrophoretic gel, such as those used for separating and characterizing nucleic acids or proteins, or a blot prepared by transfer from an electrophoretic gel to a membrane. In other aspects, the matrix is a silicon chip or glass slide, and the analyte of interest has been immobilized on the chip or slide in an array (e.g., the sample comprises proteins or nucleic acid polymers in a microarray). In yet other aspects, the matrix is a microwell plate or microfluidic chip, and the sample is analyzed by automated methods, typically by various methods of high-throughput screening, such as drug screening.

The dye conjugates are generally utilized by combining the conjugate as described above with the sample of interest under conditions selected to yield a detectable optical response. The sample is then illuminated at a wavelength selected to elicit the optical response. Typically, a specified characteristic of the sample is determined by comparing the optical response with a standard or expected response.

A detectable optical response means a change in, or occurrence of, an optical signal that is detectable either by observation or instrumentally. Typically, the detectable response is a change in fluorescence, such as a change in the intensity, excitation or emission wavelength distribution of fluorescence, fluorescence lifetime, fluorescence polarization, or a combination thereof. The degree and/or location of the labeling, compared with a standard or expected response, indicates whether, and to what degree, the sample possesses a given characteristic. Some dyes of the invention may exhibit little fluorescence emission, but are still useful as chromophoric dyes. Such chromophores are useful as energy acceptors in FRET applications, or to simply impart the desired color to a sample or portion of a sample.

For biological applications, the dye conjugates are typically used in an aqueous, mostly aqueous or aqueous-miscible solution prepared according to methods generally known in the art. The exact concentration of the dye compound is dependent upon the experimental conditions and the desired results, but typically ranges from about one nanomolar to one millimolar or more. The optimal concentration may be determined by systematic variation until satisfactory results, with minimal background fluorescence, are accomplished.

The dye conjugates may be used to label samples containing biological components. The sample may comprise heterogeneous mixtures of components (including intact cells, cell extracts, cell lysates, bacteria, viruses, organelles, and mixtures thereof) or a single component or homogeneous group of components (e.g., natural or synthetic amino acid, nucleic acid or carbohydrate polymers, or lipid membrane complexes). The dyes are generally non-toxic to living cells and other biological components within the concentrations of use.

The dye conjugate may be combined with the sample in a way that facilitates contact between the dye conjugate and the sample components of interest. Typically, the dye conjugate or a solution containing the dye conjugate is simply added to the sample. Certain dyes of the invention, e.g., those that are substituted by one or more sulfonic acid moieties, may be less permeant to membranes of biological cells, but once inside viable cells are typically well retained. Treatments that permeabilize the plasma membrane, such as electroporation, shock treatments or high extracellular ATP, may be used to introduce selected dye conjugates into cells. Alternatively, selected dye conjugates can be physically inserted into cells, e.g., by pressure microinjection, scrape loading, patch clamp methods, or phagocytosis.

Dyes that incorporate an aliphatic amine or a hydrazine residue may be microinjected into cells where they can be fixed in place by aldehyde fixatives such as formaldehyde or glutaraldehyde. This property makes such dyes useful for intracellular applications such as neuronal tracing.

Dyes that possess a lipophilic substituent, such as phospholipids, may non-covalently incorporate into lipid assemblies, e.g., for use as probes for membrane structure, or for incorporation in liposomes, lipoproteins, films, plastics, lipophilic microspheres or similar materials; or for tracing. Lipophilic dyes are useful as fluorescent probes of membrane structure.

Chemically reactive dye compounds may covalently attach to a corresponding functional group on a wide variety of materials to form dye conjugates as described above. Using dye compounds to label reactive sites on the surface of cells, in cell membranes, in intracellular compartments such as organelles, or in the cytoplasm, permits the determination of their presence or quantity, accessibility, activity or their spatial and temporal distribution in the sample. Photoreactive dyes may be used similarly to photolabel components of the outer membrane of biological cells or as photo-fixable polar tracers for cells.

In some embodiments, chloroalkane-labeled dyes may be used with HaloTag® protein to detect proteins of interest by generating a fusion protein between the HaloTag® protein and the protein of interest. Generally, these fusion proteins are expressed by a cell from a HaloTag® fusion construct, and the fusion protein is detected through use of the chloroalkane-labeled dye. This allows detection of protein expression or determination of a protein expression time-course, protein localization or migration. In addition, these proteins can be detected in gels using this fluorescent label. The dyes may also be utilized in other orthogonal labeling systems, such as cutinase, dihydrofolate reductase/trimethoprim SNAP-tag, Clip Tag, Alkyl cytosine transferase (see U.S. Patent Application No. 2012/0237961, which is incorporated by reference herein) and Acyl Carrier Protein (see U.S. Patent Application No. 2010/0173384, which is incorporated by reference herein). In addition, HaloTag is also orthogonal to other labeling chemistries such as Hsuingen cyclizations (click chemistry), hydrazone and oxime formation and the Staudinger ligation.

Optionally, the sample is washed after labeling to remove residual, excess or unbound dye compound or dye conjugate. The sample is optionally combined with one or more other solutions in the course of labeling, including wash solutions, permeabilization and/or fixation solutions, and solutions containing additional detection reagents. An additional detection reagent typically produces a detectable response due to the presence of a specific cell component, intracellular substance or cellular condition, according to methods generally known in the art. When the additional detection reagent has, or yields a product with, spectral properties that differ from those of the subject dye compounds, multi-color applications are possible. This is particularly useful where the additional detection reagent is a dye or dye conjugate having spectral properties that are detectably distinct from those of the labeling dye.

The dye conjugates are used according to methods known in the art, e.g., use of antibody conjugates in microscopy and immunofluorescent assays; or nucleotide or oligonucleotide conjugates for nucleic acid hybridization assays, nucleic acid amplification reactions, and nucleic acid sequencing (e.g., U.S. Pat. Nos. 5,332,666, 5,171,534, and 4,997,928, and WO 94/05688). Dye conjugates of multiple independent dyes of the invention possess utility for multi-color applications.

At any time after or during labeling, the sample is illuminated with a wavelength of light selected to give a detectable optical response and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors.

The optical response is optionally detected by visual inspection or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

Exemplary Methods of Use
  i. Detection of Nucleic Acid Polymers

In some embodiments, a dye oligonucleotide conjugate of the present invention is combined with a sample that contains, or is thought to contain, a nucleic acid polymer, incubating the mixture of dye oligonucleotide conjugate, e.g., probe or primer, and sample for a time sufficient for the oligonucleotide in the conjugate to combine with nucleic acid polymers in the sample to form nucleic acid hybrids (complexes) (i.e., a probe), or to prime nucleic acid synthesis (i.e., a primer), which may be detected. The characteristics of the labeled molecules, including the presence, location, intensity, excitation and emission spectra, fluorescence polarization, fluorescence lifetime, and other physical properties of the fluorescent signal, can be used to detect, differentiate, sort, quantitate, sequence and/or analyze aspects or portions of the sample. The dye conjugates of the invention are optionally used in conjunction with one or more additional reagents (e.g., detectably different fluorescent reagents) including dyes of the same class having different spectral properties.

In some embodiments, the dyes of the present invention can be used in the Internal Lane Standard (ILS). An ILS is used to assign reproducible sizing of DNA fragments separated by electrophoresis and detected using a variety of fluorescence-detection instruments. In some embodiments, the ILS consists of double-stranded DNA from 2-21 peaks ranging in size from 60 bp to 500 bp. In some embodiments, fragments of 60-200 bp are spaced at 20 bp intervals and fragments of 200-500 bp are spaced every 25 bases.

Typically, the dye conjugate is prepared for use by dissolving the dye conjugate in an aqueous or aqueous miscible solution that is compatible with the sample and intended use. For biological samples, where minimal perturbation of cell morphology or physiology is desired, the solution is selected accordingly.

The labeling solution is made by dissolving the dye conjugate directly in an aqueous solvent such as water, a buffer solution, such as buffered saline (preferably non-phosphate for some viability discrimination applications), a Tris(hydroxymethyl)-aminomethane (TRIS) buffer (preferably containing EDTA), or a water-miscible organic solvent such as dimethylsulfoxide (DMSO), dimethylformamide (DMF), or a lower alcohol such as methanol or ethanol. The dye conjugate is usually preliminarily dissolved in an organic solvent (e.g., 100% DMSO) at a concentration of greater than about 100 times that used in the labeling solution, then diluted one or more times with an aqueous solvent such as water or buffer, such that the dye conjugate is present in an effective amount.

Typically labeling solutions for cellular samples have a dye concentration greater than 0.1 nM and less than 50 µM, more typically greater than 1 nM and less than 10 µM, e.g., between 0.5 and 5 µM. Labeling solutions for electrophoretic gels typically have a dye concentration of greater than 0.1 µM and less than 10 µM, more typically about 0.5 to 2 µM. The same holds true when the dye is added to the gel before being combined with nucleic acids. Labeling solutions for detection and quantitation of free nucleic acids in solution typically have a concentration of 0.1 µM to 2 µM. The optimal concentration and composition of the labeling solution is determined by the nature of the sample (including physical, biological, biochemical and physiological properties), the nature of the dye-sample interaction (including the transport rate of the dye to the site of the nucleic acids), and the nature of the analysis being performed, and can be determined according to standard procedures.

The nucleic acid in the sample may be DNA or RNA, or a mixture or a hybrid thereof. Any DNA is optionally single-, double-, triple-, or quadruple-stranded DNA; any RNA is optionally single stranded ("ss") or double stranded ("ds"). The nucleic acid may be a natural polymer (biological in origin) or a synthetic polymer (modified or prepared artificially). The nucleic acid polymer (for instance, one containing at least 8 bases or base pairs) may be present as nucleic acid fragments, oligonucleotides, or larger nucleic acid polymers with secondary or tertiary structure. The nucleic acid is optionally present in a condensed phase such as a chromosome. The nucleic acid polymer optionally contains one or more modified bases or links or contains labels that are non-covalently or covalently attached. For example, the modified base can be a naturally occurring modified base such as Ψ (pseudouridine) in tRNA, 5-methylcytosine, 6-methylaminopurine, 6-dimethylaminopurine, 1-methylguanine, 2-methylamino-6-hydroxypurine, 2-dimethylamino-6-hydroxypurine, 5-amino-DU, isoC, isoG, or other known minor bases (see, e.g., Davidson, The Biochemistry Of The Nucleic Acids (1976)) or is synthetically altered to contain an unusual linker such as morpholine derivatized phosphates (AntiVirals, Inc., Corvallis, Oreg.), or peptide nucleic acids such as N-(2-aminoethyl)glycine units (Wittung et al., Nature, 368:561 (1994)) or contain a simple reactive functional group (<10 carbons) that is an aliphatic amine, carboxylic acid, alcohol, thiol or hydrazine, or contain a fluorescent label or other hapten, such as inosine, bromodeoxyuridine, iododeoxyuridine, biotin, digoxigenin, 2,4-dinitrophenyl, where the label is originally attached on the nucleotide (e.g., CHROMA-TIDE™ labeled nucleotides, Molecular Probes, Eugene, Oreg.) or located on the 3' or 5' end of a nucleic acid polymer, or ligands non-covalently attached to the nucleic acids. The sensitivity of the dyes for nucleic acid polymers containing primarily modified bases and links may be diminished by interference with the binding mode. Some embodiments of the dyes may inhibit non-specific nuclease activity but not restriction endonuclease activity at certain dye:base pair ratios.

The sample that contains a nucleic acid is optionally a biological structure (i.e., an organism or a discrete unit of an organism), or a solution (including solutions that contain biological structures), or a solid or semi-solid material. Consequently, the nucleic acid is optionally free in solution, immobilized in or on a solid or semi-solid material, extracted from a biological structure (e.g., from lysed cells, tissues, organisms or organelles), or remains enclosed within a biological structure. In order for the nucleic acids to bind to the dyes, it is necessary that the nucleic acids be in an aqueous environment to allow contact with the dye, even if the nucleic acids are not enclosed in a biological structure.

The biological structure that contains the nucleic acid is optionally a cell or tissue, for example, where the nucleic acid is present in a cell or interstitial space, as a prokaryote or eukaryote microorganism, or as a virus, viroid, chromosome or organelle. Alternatively, the biological structure may not be contained in a tissue or cell and is present either as a virus or as a microorganism or other cell, or is present as a cellular component removed from its parent cell (e.g., a plasmid or chromosome, or a mitochondrion or nucleus or other organelle). Typically, the biological structure is an organelle, chromosome or cell that is optionally contained within a eukaryote cell. The cell present inside a eukaryote cell is typically a parasite or other infectious agent such as a virus, bacterium, protozoa, mycoplasma or mycobacterium. When the nucleic acid is contained in a biological structure that is a cell, the cells are viable or dead cells or a mixture thereof, i.e., the integrity of the cell membrane is optionally intact or disrupted by natural (autolytic), mechanical or chemical means or by environmental means such as changes in temperature or pressure. Alternatively, the cells are blebbing or undergoing apoptosis or in a cycle of growth or cell division.

When the nucleic acid is present in a solution, the sample solution can vary to contain one of purified or synthetic nucleic acids such as oligonucleotides to crude mixtures such as cell extracts or homogenates or other biological fluids, or dilute solutions from biological, industrial, or environmental sources. In some cases, it is desirable to separate the nucleic acids from a mixture of biomolecules or fluids in the solution prior to combination with the dye. Numerous techniques exist for separation and purification of nucleic acids from generally crude mixtures with other proteins or other biological molecules. These include such means as chromatographic techniques and electrophoretic techniques using a variety of supports or solutions or in a flowing stream. Alternatively, mixtures of nucleic acids may be treated with RNase or DNase so the nucleic acid polymer is not degraded in the presence of the nuclease can be discriminated from degradation products using the subject dyes.

The relatively low toxicity of the dyes of the invention to living systems generally enables the examination of nucleic acids in living samples with little or no damage caused by the dye itself. For use with intact cells or samples in a gel, more permeant dyes may be employed, although some cells readily take up dyes that have been shown to be impermeant to other cells by means other than passive diffusion across cell-membranes, e.g., by phagocytosis or other types of ingestion. These dyes can be used in standard gel-based applications. The photostability, toxicity, binding affinity, quantum yield, and fluorescence enhancement of dyes are determined according to standard methods known in the art.

In some embodiments, a dye oligonucleotide conjugate, e.g., probe or primer, is employed in methods and kits for the identification of alleles in a physiological sample. In some embodiments, an appropriate set of loci, primers and amplification protocols is selected to generate amplified alleles from multiple co-amplified loci which, in one embodiment, do not overlap in size or which are labeled in a way which enables one to differentiate between the alleles from different loci which overlap in size. In addition, this method contemplates the selection of short tandem repeat (STR) loci which are compatible for use with a single amplification protocol. Successful combinations can be generated by trial and error of locus combinations, by selection of primer pair sequences, and by adjustment of primer concentrations to identify an equilibrium in which all included loci may be amplified. The number of loci which may be amplified in a multiplex amplification reaction step may be from 2 to 50, or any integer between 2 and 50, e.g. 16, 17, 18, 21, 23, or 26, so long as the reaction produces amplified alleles that can be identified. In some embodiments, the amplified fragments are less than 500 bp in length.

Synthesis of the primers used in the present method can be conducted using any standard procedure for oligonucleotide synthesis known to those skilled in the art. At least one primer for each locus is covalently attached to a different dye label.

Samples of genomic DNA can be prepared for use in the method of this invention using any method of DNA preparation which is compatible with the amplification of DNA. Many such methods are known by those skilled in the art. When the at least one DNA sample to be analyzed is human genomic DNA, the DNA may be prepared from samples, selected from the group consisting of tissue, blood, semen, vaginal cells, hair, saliva, urine, bone, buccal samples, amniotic fluid containing placental cells or fetal cells, chorionic villus, and mixtures of any of the samples listed above.

Once a sample of genomic DNA is prepared, the targeted loci can be co-amplified in the multiplex amplification step. Any one of a number of different amplification methods can be used to amplify the loci, including, but not limited to, polymerase chain reaction (PCR), transcription based amplification and strand displacement amplification (SDA). In one embodiment, the DNA sample is subjected to PCR amplification using primer pairs specific to each locus in the set.

At least one primer for each locus can be covalently attached to a dye label, one of which comprises a dye of the present invention. The primers and dyes attached thereto are selected for use in the multiplex amplification reaction such that the alleles amplified using primers for each locus labeled with one color do not overlap with the alleles of the other loci in the set co-amplified therein using primers labeled with the same color, when the alleles are separated, e.g., by gel or capillary electrophoresis. Fluorescent labels suitable for attachment to primers for use in the present invention are commercially available. See, e.g. fluorescein and carboxy-tetramethylrhodamine labels and their chemical derivatives from PE Biosystems and Molecular Probes. In some embodiments, at least four or five different labels are used to label the different primers used in the multiplex amplification reaction. When a size marker is included to evaluate the multiplex reaction, the primers used to prepare the size marker may be labeled with a different label from the primers used to amplify the loci of interest in the reaction.

Once a set of amplified alleles is produced from the multiplex amplification step, the amplified alleles are evaluated. The evaluation step of this method can be accomplished by any one of a number of different means. Electrophoresis may be used to separate the products of the multiplex amplification reaction, e.g., capillary electrophoresis or denaturing polyacrylamide gel electrophoresis. Gel preparation and electrophoresis procedures and conditions for suitable for use in the evaluating step are known to the art. Separation of DNA fragments in a denaturing polyacrylamide gel and in capillary electrophoresis occurs based primarily on fragment size.

Once the amplified alleles are separated, the alleles and any other DNA in the gel or capillary (e.g., DNA size markers or an allelic ladder) can then be visualized and analyzed. In one embodiment, the method for detection of multiplexes containing numerous loci is fluorescence, where primers for each locus in the multiplexing reaction is followed by detection of the labeled products employing a fluorometric detector.

ii. Other Uses

The fluorescent dyes of the present invention can be used in other techniques known to those skilled in the art. For example, the dyes may be used in antibody staining, in studies of organometallic catalysis in living cells, in biomedical imaging, in in vivo detection of small molecules, thiol-reactive probes, biotin and hapten derivatives, nucleic acid and protein analysis, for probing cellular structure (including cytoskeletal proteins, organelles, lipids and membranes and as fluorescent tracers of cell morphology and fluid flow), and for probing cellular function (including cell viability, cell proliferation, endocytosis, receptors, ion channels, signal transduction, ROS, various cations, and membrane potential.

The dyes may also be used to detect biological phenomena using fluorescent resonance energy transfer FRET or bioluminescence resonance energy transfer (BRET). See, e.g. "The Molecular Probes® Handbook" (www.invitrogen.com) for a description of various uses for the dyes of the present invention. In some embodiments, the dyes disclosed herein can be used as BRET acceptors. If a dye described herein is brought within the energy transfer radius (e.g., typically <10 nm) of a luciferase and is in the correct orientation, radiationless energy transfer will occur, and the dye will emit light at its normal emission. There are many methods known for bringing the dye close to a luciferase, e.g., small molecules or quantum dots (Xia, Z and Rao, J. 2009. Curr. Opin. Biotech 20: 37-44), and these methods enable one to learn something about a biological system of interest.

In some embodiments, the use of a dye disclosed herein in FRET or BRET can be used to ascertain the biological interaction of any two materials of interest such as nucleic acids, lipids, polysaccharides, antibodies, small molecules, e.g. drugs or drug compounds, etc. In some embodiments, the interaction of a small molecule with a protein occurs inside of a living cell. In some embodiments, a dye disclosed herein may be conjugated to a small molecule, e.g., a tracer, that binds to a protein of interest in such a way that the molecule/ protein interaction is not disturbed by the dye conjugation. If the protein of interest is expressed as a luciferase fusion as described above, the interaction of the small molecule with the protein can be measured inside a live cell. Such an assay may also be used to investigate the binding of a promiscuous small molecule with only a single protein regardless of how many other proteins the particular small molecule may bind. In some embodiments, the reactive dyes of the present invention may be used to label a protein(s) or peptide(s) for quantification of protein interactions in situ. In some aspects, a dye label could be attached to the target protein or peptide of interest using the reactive cyanobenzothiazole (CBT) labeling chemistry (see U.S. Patent Application No. 2009/0263843, which is incorporated by reference herein). The CBT labeling chemistry requires a free, N-terminal cysteine residue on the target protein or peptide, which can be generated in situ or in a biochemical format, e.g., by site-specific proteolytic cleavage (e.g. cleavage of an N-terminal reporter such as HaloTag from a C-terminal target protein or peptide). Once proteolysis has occurred and an N-terminal cysteine residue generated, the reactive CBT labeling method can be used to generate a single dye label on the target protein or peptide of interest. This method could also be used for site-specific labeling of receptor ligands (e.g. cytokines or peptide ligands). When the dye-labeled ligand is bound in close proximity to a cell surface receptor labeled with a suitable energy donor (e.g. luciferase for bioluminescence resonance energy transfer (BRET) or a short-wavelength fluorophore for Forster resonance energy transfer (FRET)), energy transfer can occur between the excited state donor and fluorescent dye acceptor, leading to an increase in emission from the conjugated dye. Energy transfer could then be used to quantify the interaction of the protein/peptide that has been labeled with the CBT-dye with the donor-labeled receptor of interest. This labeling method may be compatible with purified components, e.g., purified protein or peptide, or in more complex samples including whole cells or cell lysates. Furthermore, this labeling method may be useful for testing the affinity of unlabeled proteins/peptides for a receptor of interest by competitive displacement of the ligand-receptor complex generating the BRET signal.

Compounds

Compound useful in the methods of the present invention include compounds according to Formula (I):

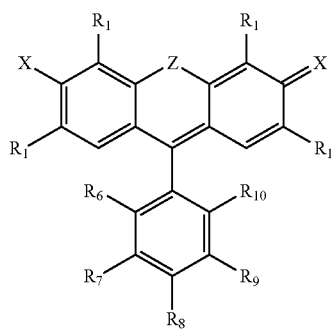

(I)

wherein

Z is $Si(R_{11})(R_{12})$ or $Ge(R_{11})(R_{12})$;

each $R_{11}$ and $R_{12}$ are independently selected from $C_{1-10}$ linear, branched or cyclic alkyl, $C_{1-10}$ alkyl interrupted with one or more heteroatoms, $C_{6-10}$ aryl, heteroaryl or $R_{11}$ and $R_{12}$ may together form a ring;

each X is independently selected from $OR_2$ or $N(R_3)(R_4)$;

each $R_1$ is independently selected from H, $C_{1-4}$ alkyl, sulfonate or halo;

$R_2$ is H, $C_{1-10}$ alkyl, L-R or L-$C_S$;

$R_3$ and $R_4$ are independently selected from H, $C_{1-4}$ alkyl, $C_{1-4}$ alkyl interrupted with one or more heteroatoms, $C_{6-10}$ aryl, peptidyl, heteroaryl, L-R or L-$C_S$;

$R_{6-10}$ are independently H, halo, alkoxy, amino, alkyl, aryl, heteroaryl, $CO_2H$, $SO_3H$, L-$CO_2H$, L-$SO_3H$, L-R or L-$C_S$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group; or $C_S$ is a conjugated substance;

one or more of $R_3$ and $R_4$ or $R_3$ and $R_1$ or $R_4$ and $R_1$ may together form a ring;

and one or more of $R_{6-10}$ may together form a ring.

In some embodiments, the compound is of Formula (II):

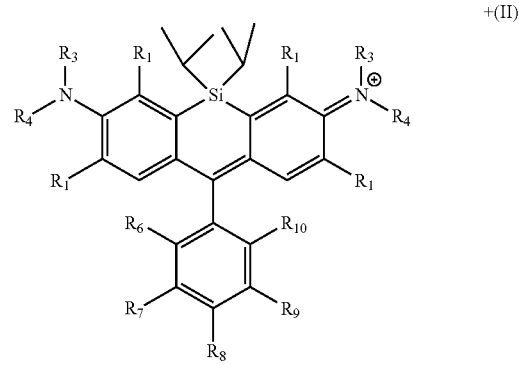

+(II)

wherein each $R_1$ is independently selected from H, $C_{1-4}$ alkyl, sulfonate or halo;

$R_3$ and $R_4$ are independently selected from H, $C_{1-4}$ alkyl, $C_{1-4}$ alkyl interrupted with one or more heteroatoms, L-R or L-$C_S$;

$R_{6-9}$ are independently H, halo, alkyl, aryl, heteroaryl, $CO_2H$, $SO_3H$, L-$CO_2H$, L-$SO_3H$, L-R or L-$C_S$;

$R_{10}$ is alkoxy, alkyl, aryl, heteroaryl, $CO_2H$, $SO_3H$, $SO_2N(R_N)_2$, $CON(R_N)_2$, L-$CO_2H$, L-$SO_3H$, L-R or L-$C_S$;

each $R_N$ is independently selected from H, alkyl, aryl, heteroaryl, L-R, and L-$C_S$ L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group; or $C_S$ is a conjugated substance;

one or more of $R_3$ and $R_4$ or $R_3$ and $R_1$ or $R_4$ and $R_1$ may together form a ring;
and
one or more of $R_{6-9}$ may together form a ring.

In some embodiments, the compound is selected from the group consisting of:

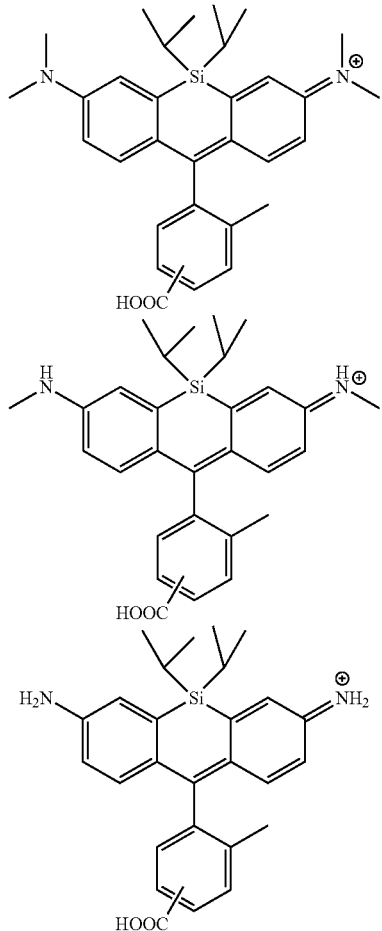

Figure 13:
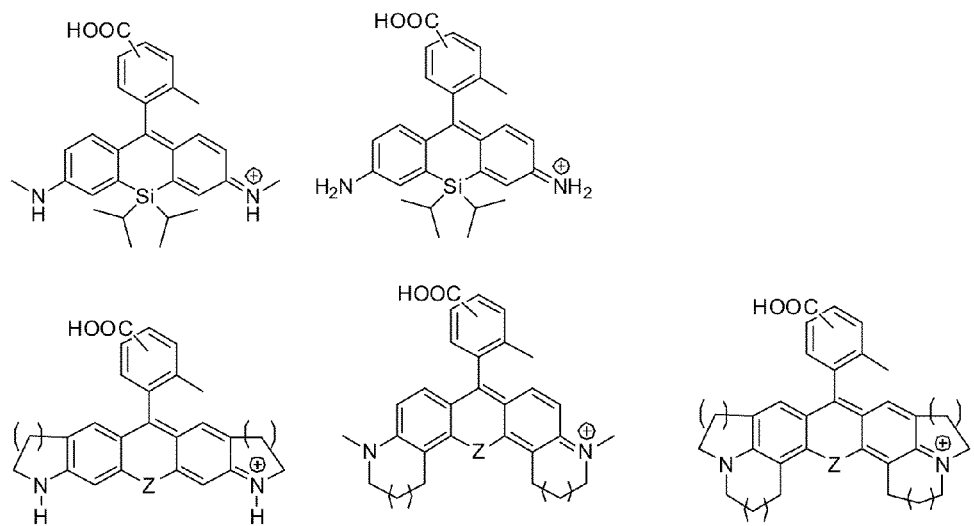
FIG. 13 provides compounds useful in the methods of the present invention.
Figure 14:
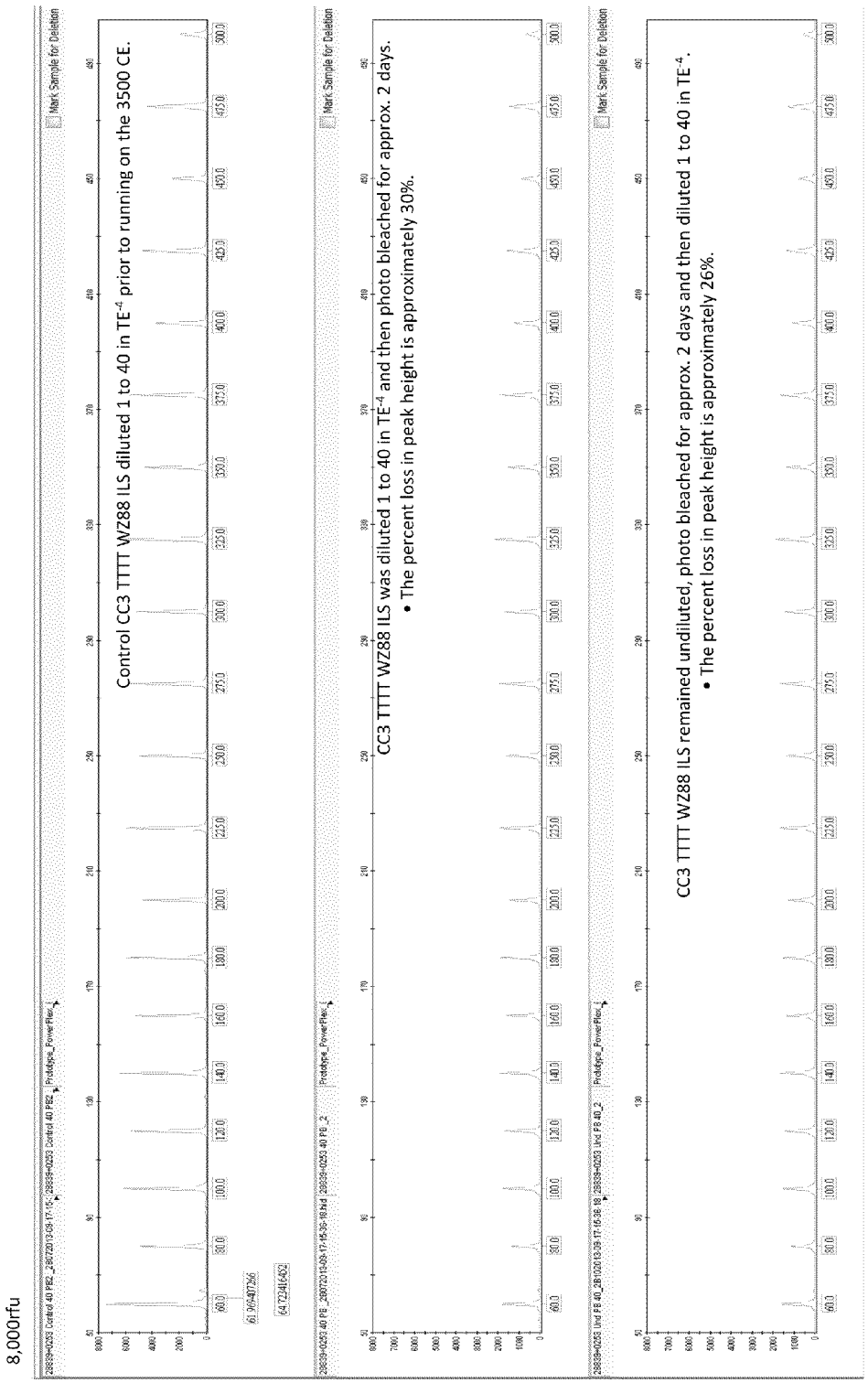
FIG. 14 demonstrates that the CC3-TTTT-WZ88 ILS (diluted or undiluted) experienced approximately 30% loss in peak height after the two day photo-bleaching.
Figure 15:
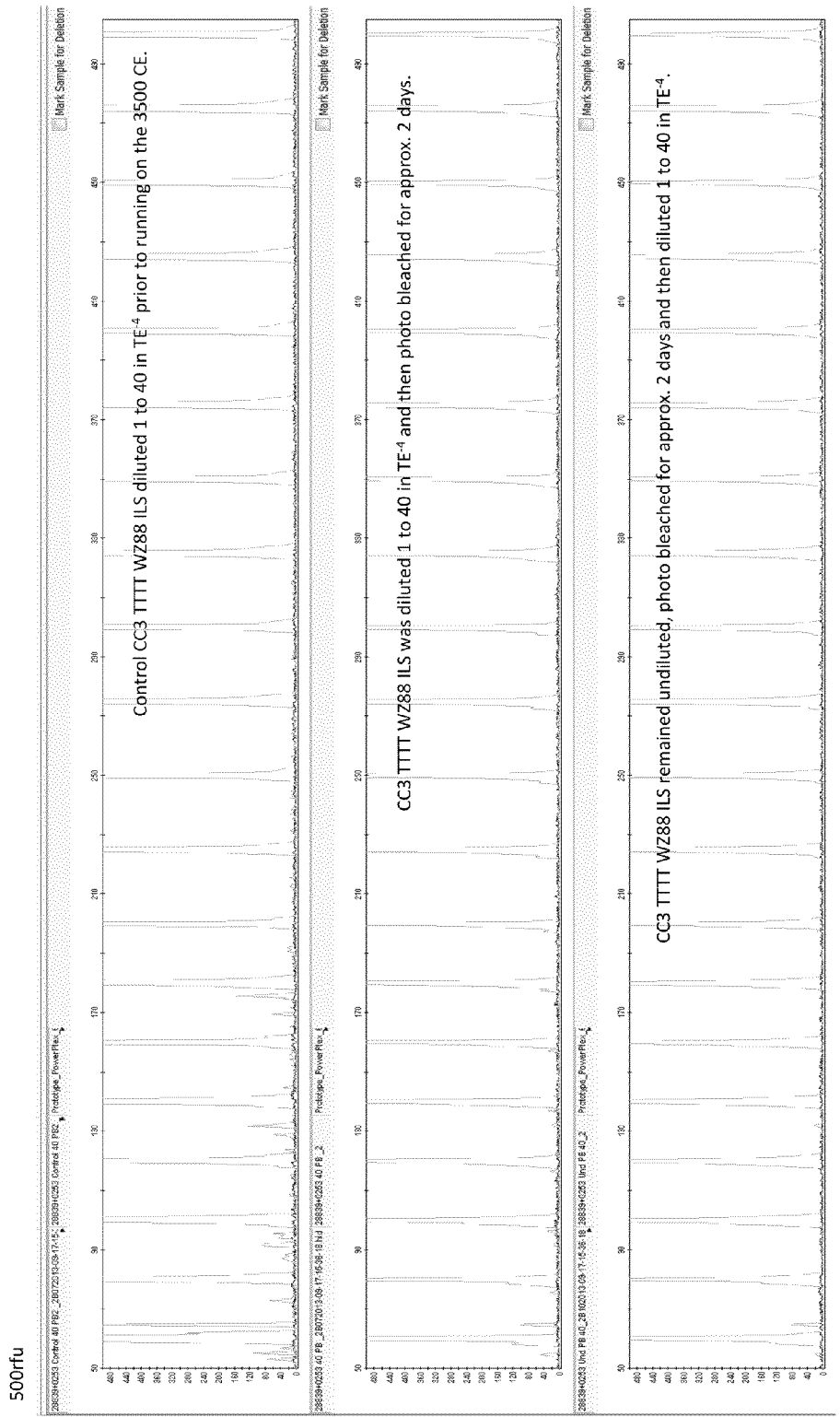
FIG. 15 demonstrates that the CC3-TTTT-WZ88 ILS (diluted or undiluted) showed low signal to noise in the fluorescein channel after the two day photo-bleaching.
Figure 16:
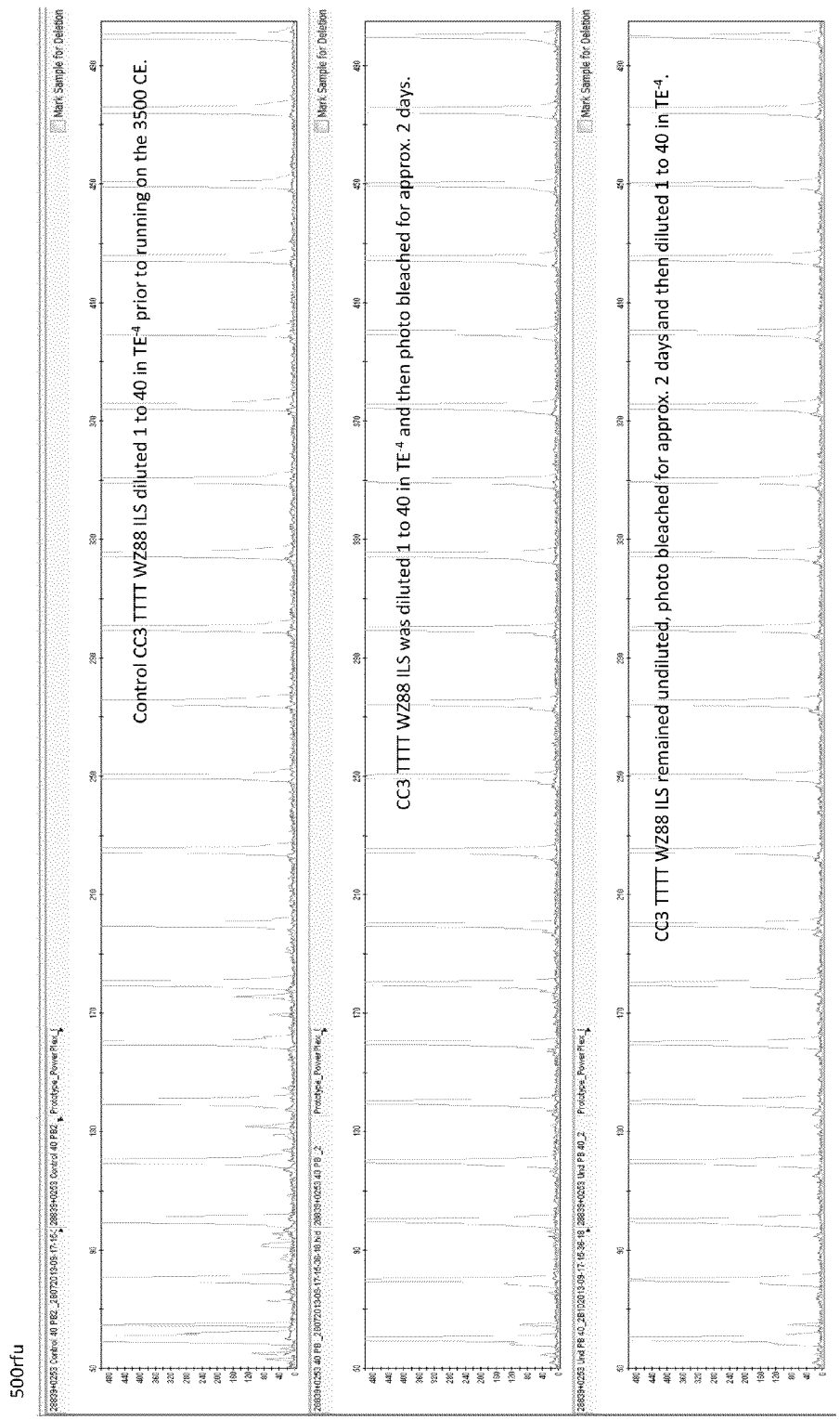
FIG. 16 demonstrates that the CC3-TTTT-WZ88 ILS (diluted or undiluted) showed low signal to noise in the JOE channel after the two day photo-bleaching.
Figure 17:
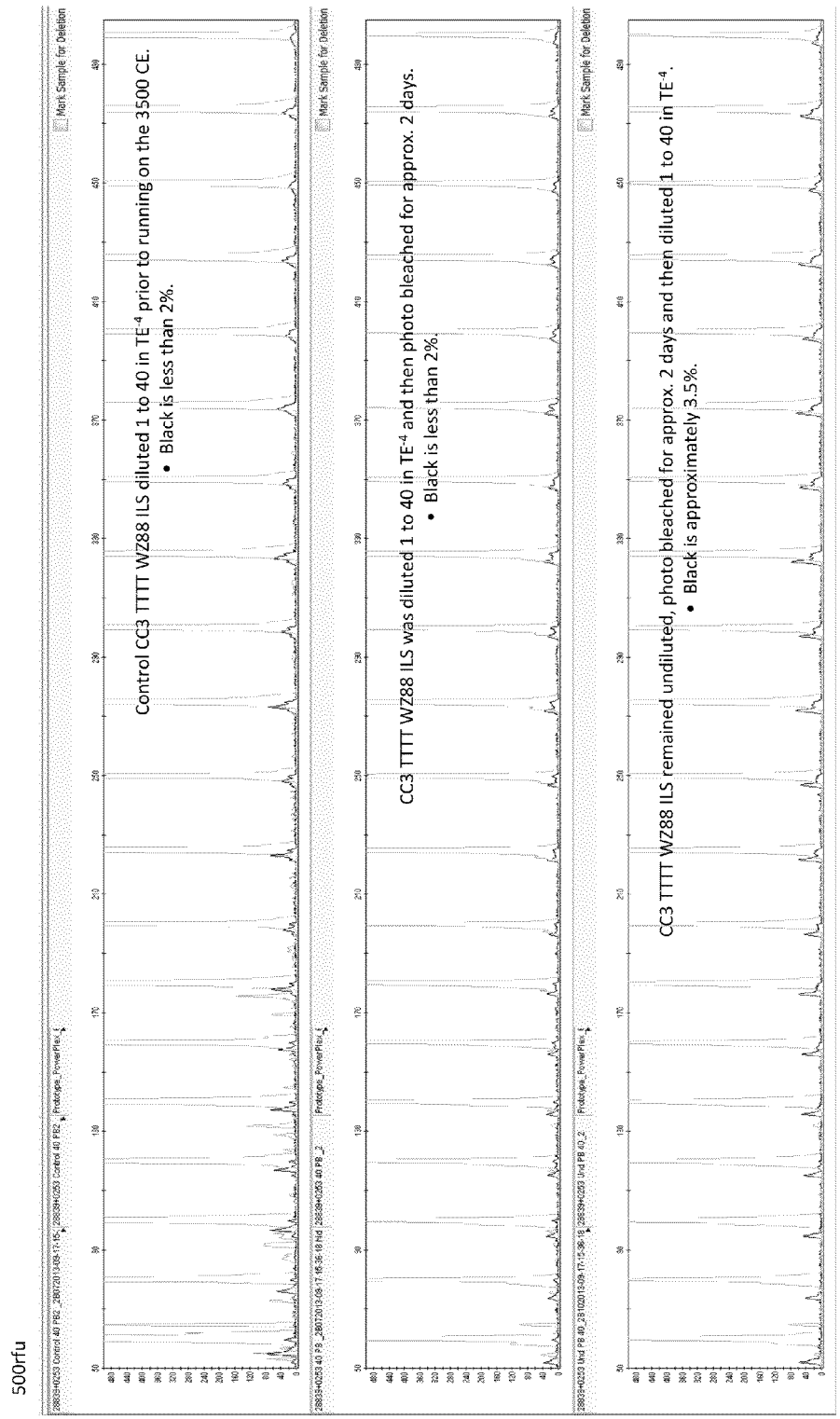
FIG. 17 demonstrates that the CC3-TTTT-WZ88 ILS (diluted or undiluted) experienced approximately 4% black into orange in the ET-TMR channel after the two day photo-bleaching.
Figure 18:
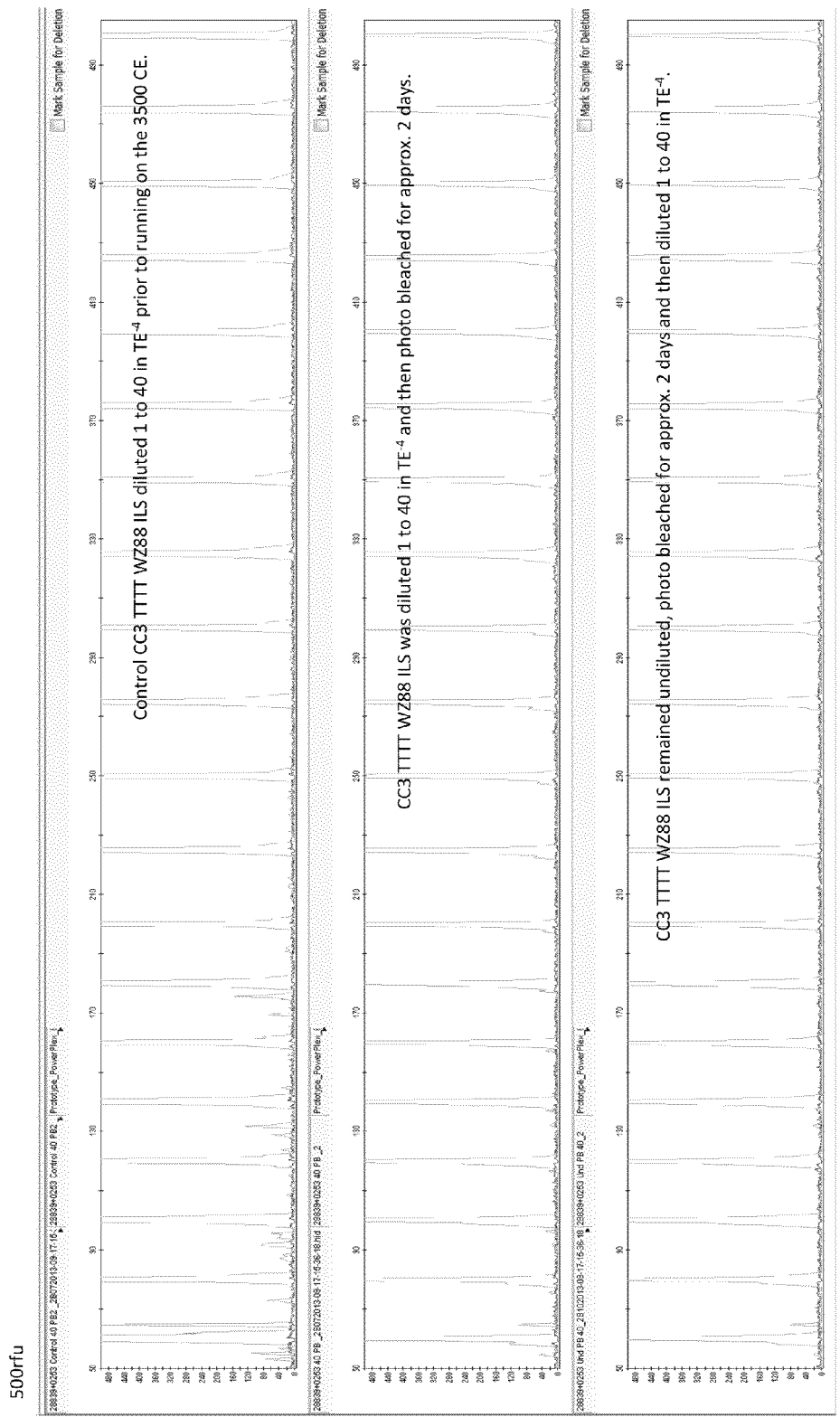
FIG. 18 demonstrates that the CC3-TTTT-WZ88 ILS (diluted or undiluted) showed low signal to noise in the ET-CXR channel after the two day photo-bleaching.
Figure 19:
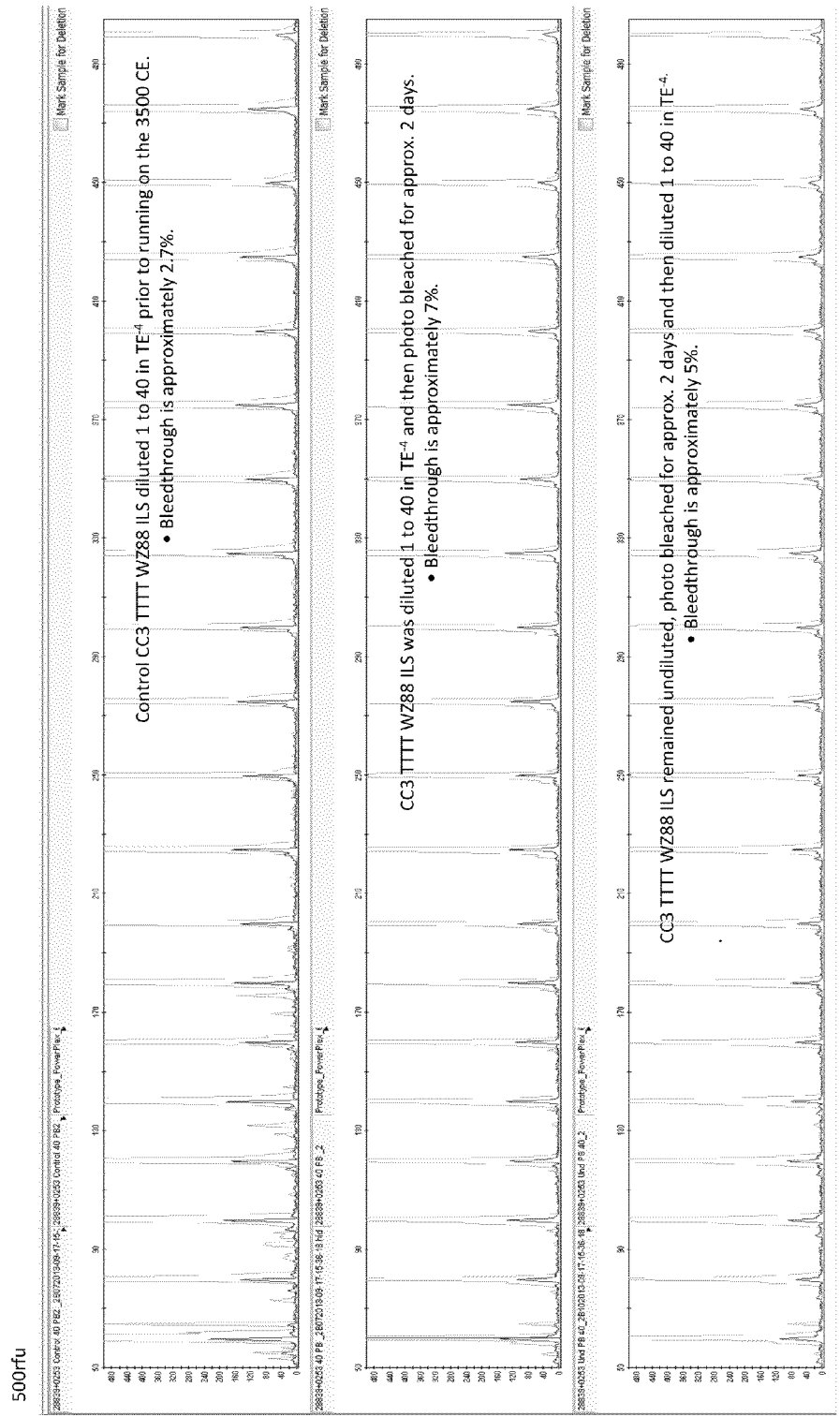
FIG. 19 demonstrates that the CC3-TTTT-WZ88 ILS (diluted or undiluted) experienced approximately 10% bleedthrough in the ET-TOM channel after the two day photo-bleaching.
Figure 20:
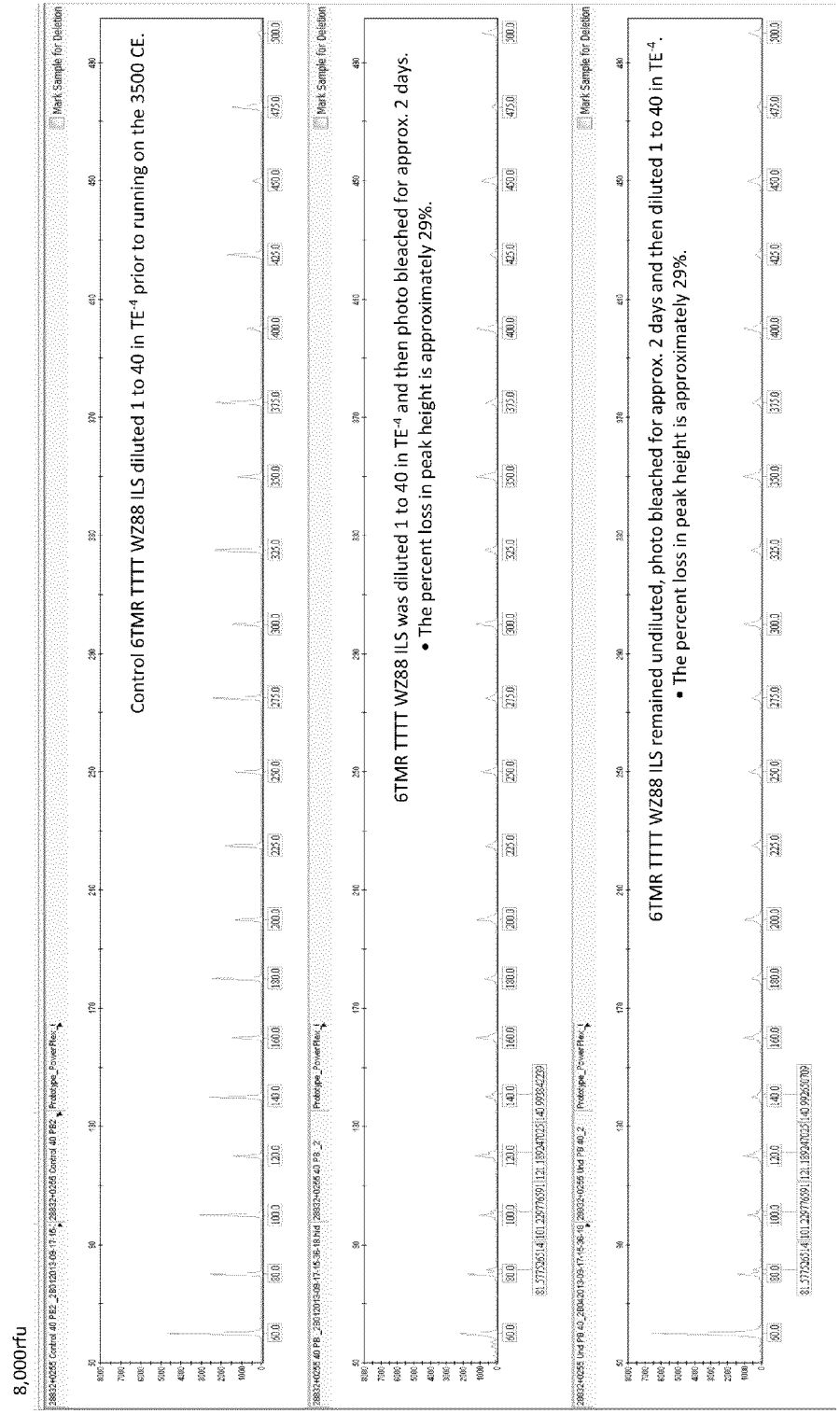
FIG. 20 demonstrates that the 6-TMR-TTTT-WZ88 ILS (diluted or undiluted) experienced approximately 30% loss in peak height after the two day photo-bleaching.
Figure 21:
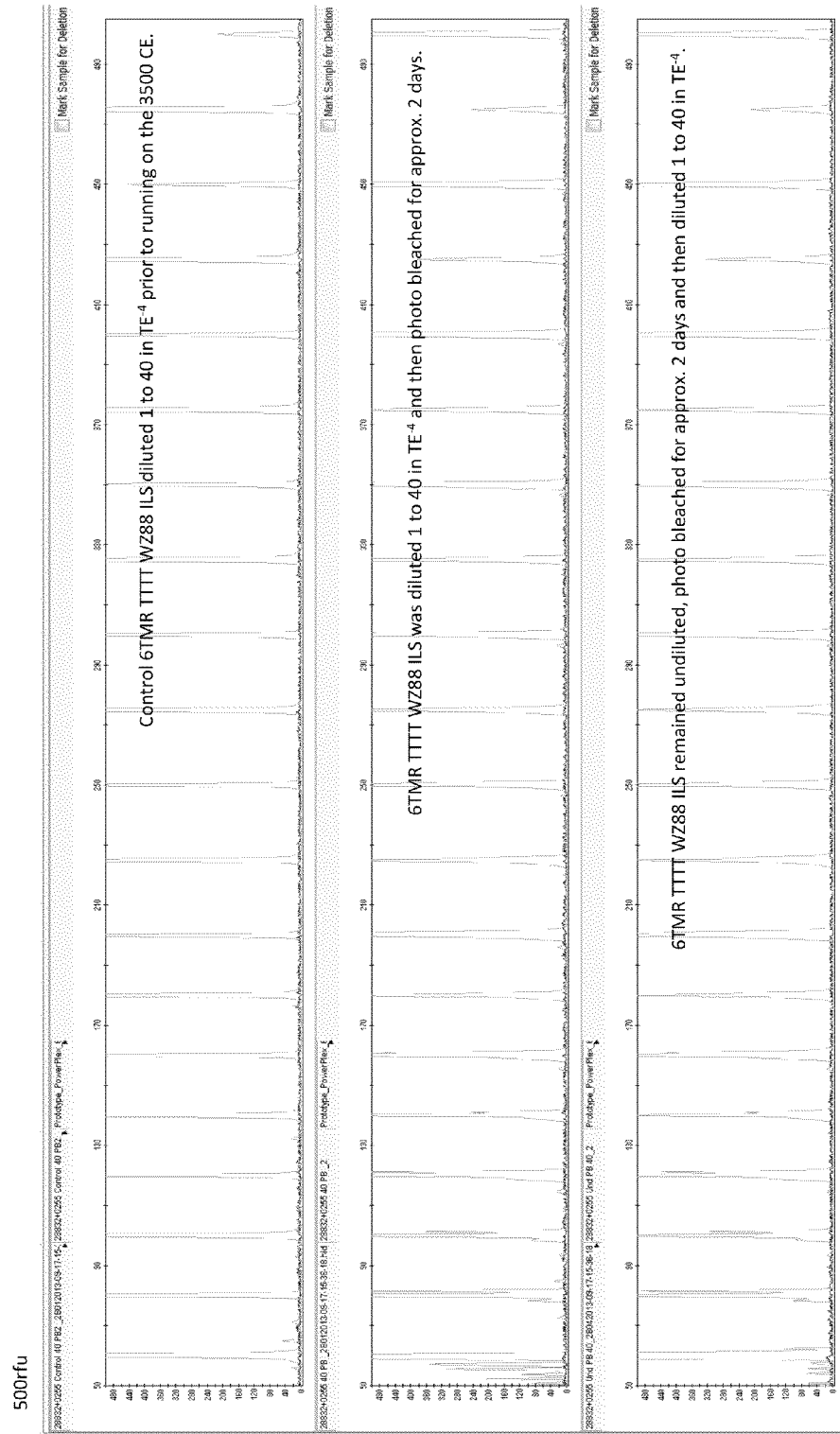
FIG. 21 demonstrates that the 6-TMR-TTTT-WZ88 ILS (diluted or undiluted) showed low signal to noise in the fluorescein channel after the two day photo-bleaching.
Figure 22:
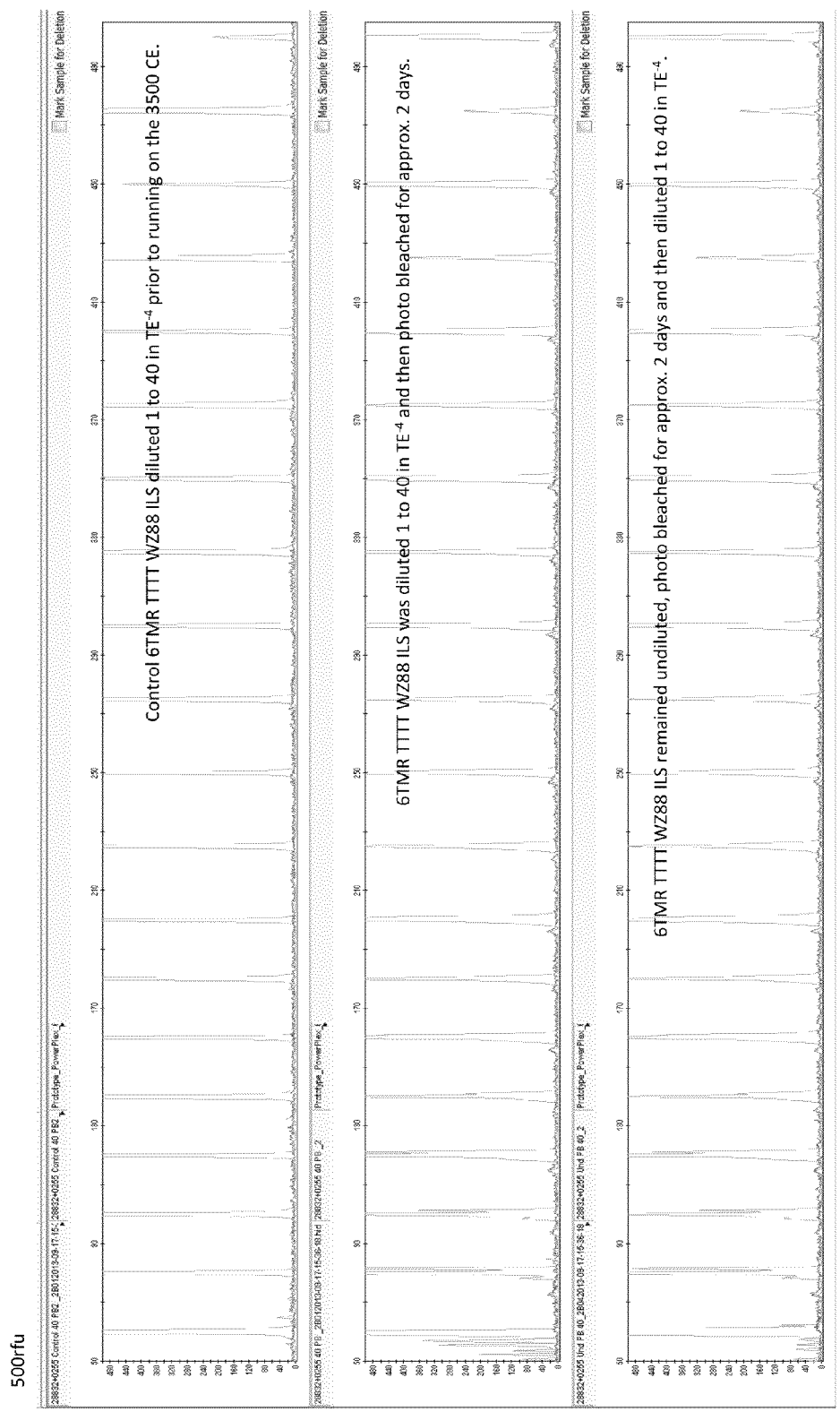
FIG. 22 demonstrates that the 6-TMR-TTTT-WZ88 ILS (diluted or undiluted) showed low signal to noise in the JOE channel after the two day photo-bleaching.
Figure 23:
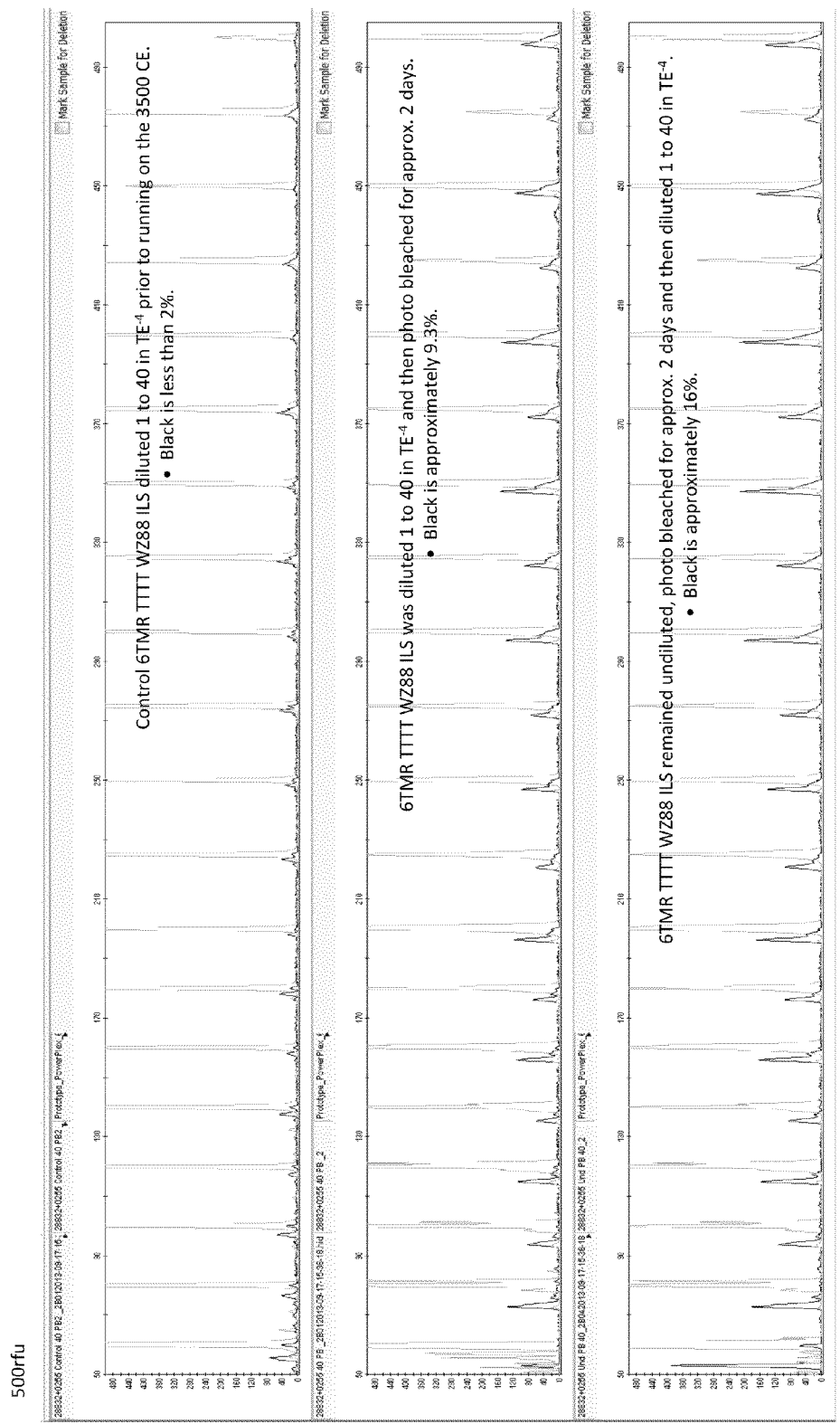
FIG. 23 demonstrates that the 6-TMR-TTTT-WZ88 ILS (diluted or undiluted) experienced approximately 17% black into orange in the ET-TMR channel after the two day photo-bleaching.
Figure 24:
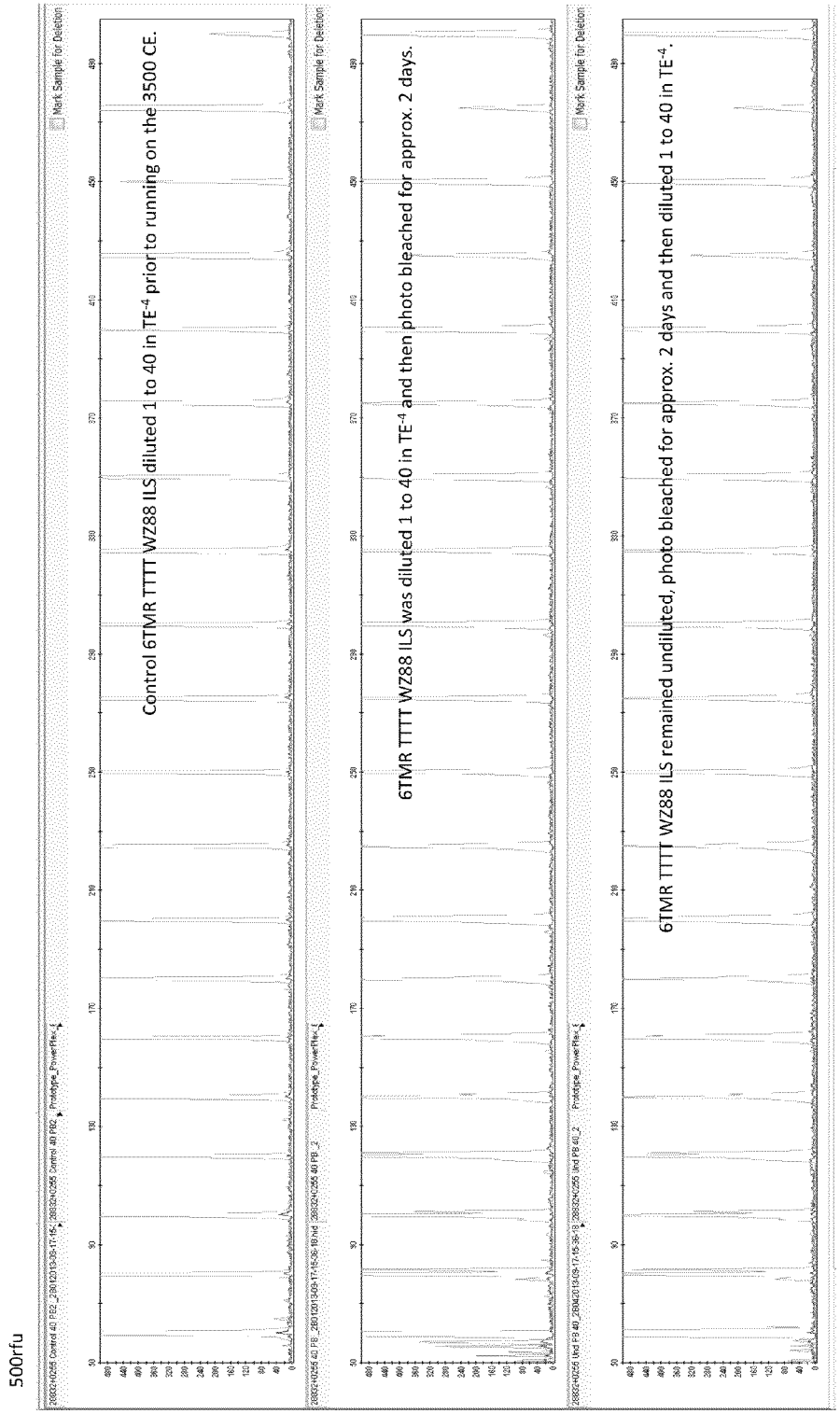
FIG. 24 demonstrates that the 6-TMR-TTTT-WZ88 ILS (diluted or undiluted) showed low signal to noise in the ET-CXR channel after the two day photo-bleaching.
Figure 25:
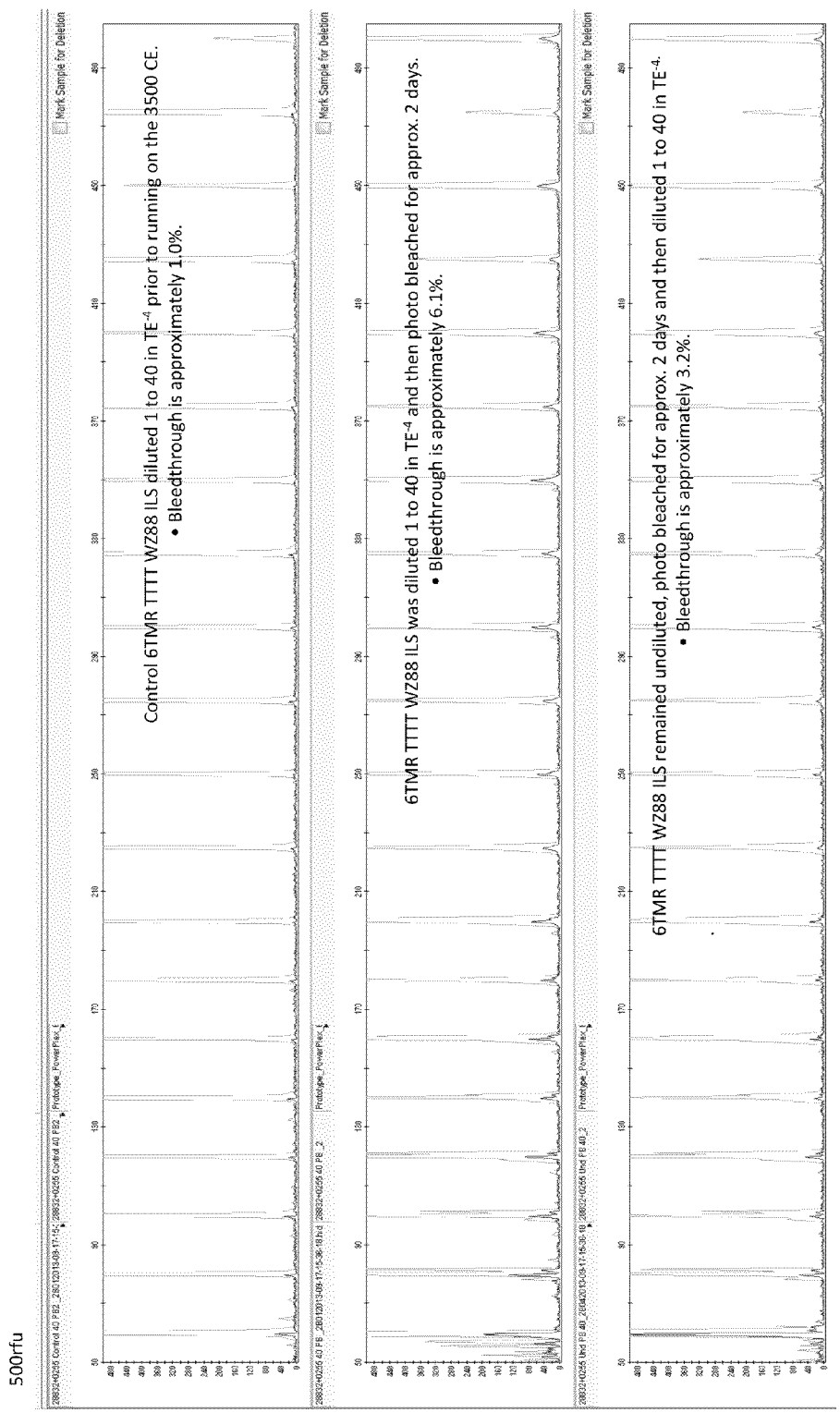
FIG. 25 demonstrates that the 6-TMR-TTTT-WZ88 ILS (diluted or undiluted) experienced approximately 7% bleedthrough in the ET-TOM channel after the two day photo-bleaching.
Figure 26:
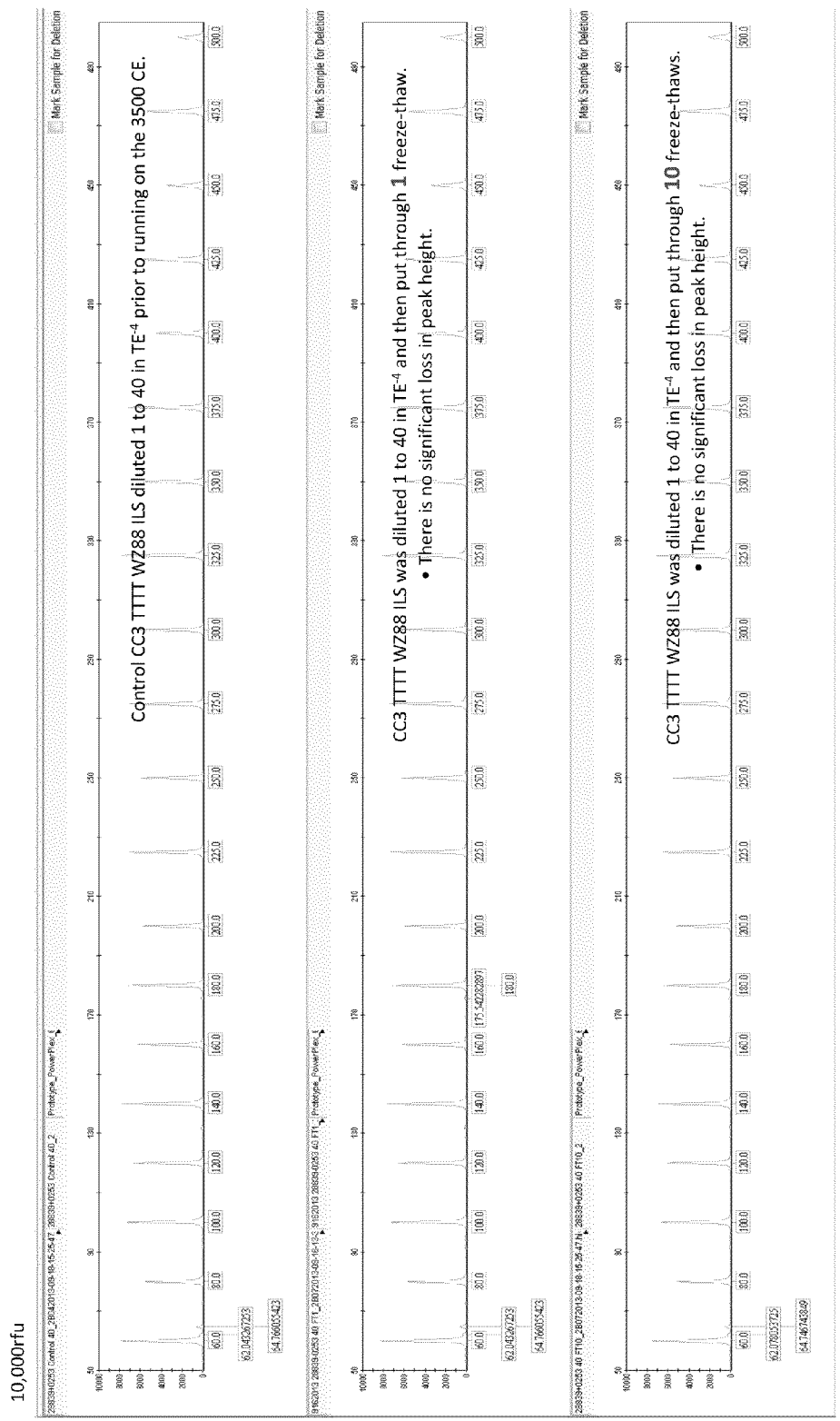
FIG. 26 demonstrates that the CC3-TTTT-WZ88 ILS (diluted) experienced no significant loss in peak height after 1 or 10 freeze-thaw cycles.
Figure 27:
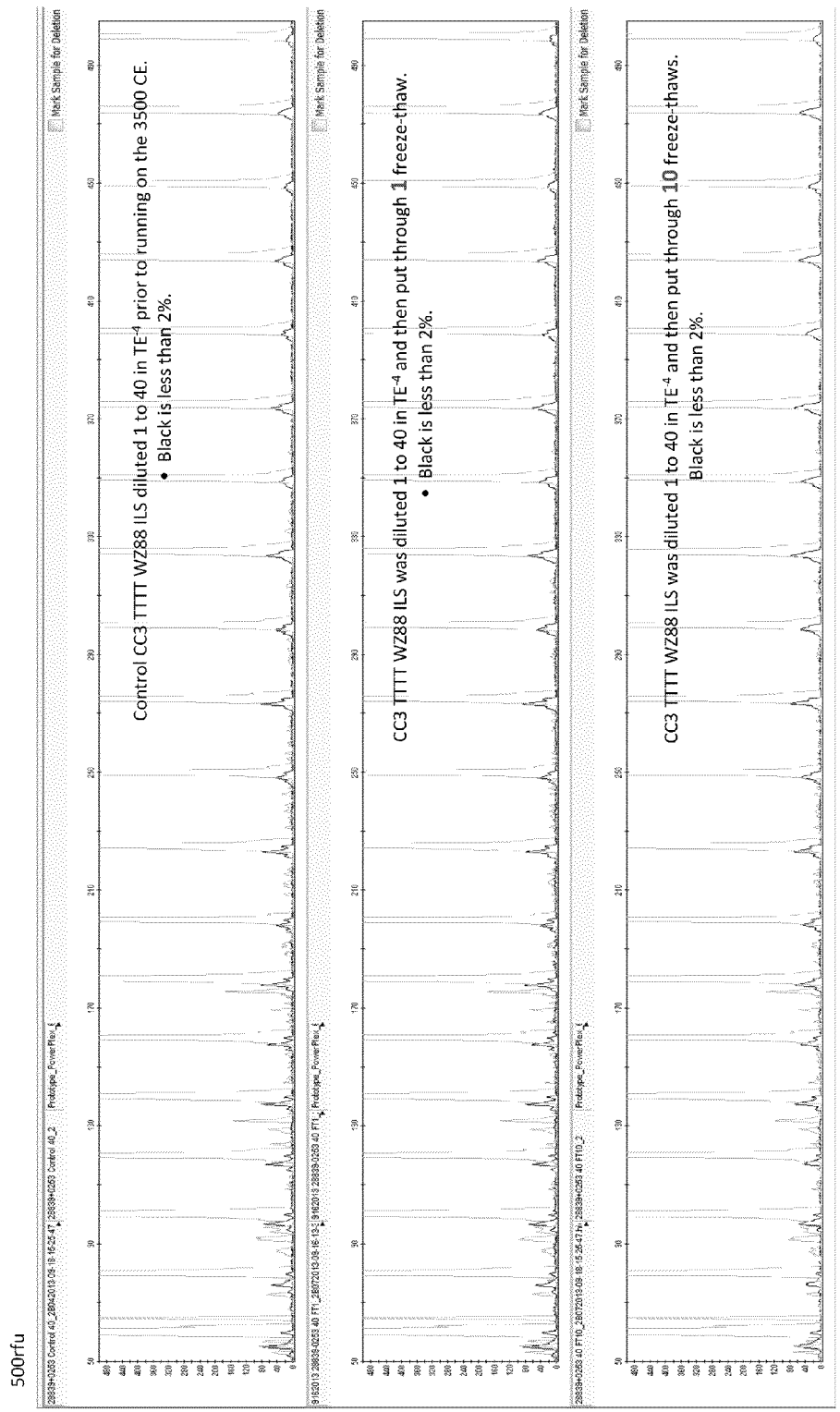
FIG. 27 demonstrates that the CC3-TTTT-WZ88 ILS (diluted) experienced approximately 2% black into orange after 1 or 10 freeze-thaw cycles.
Figure 28:
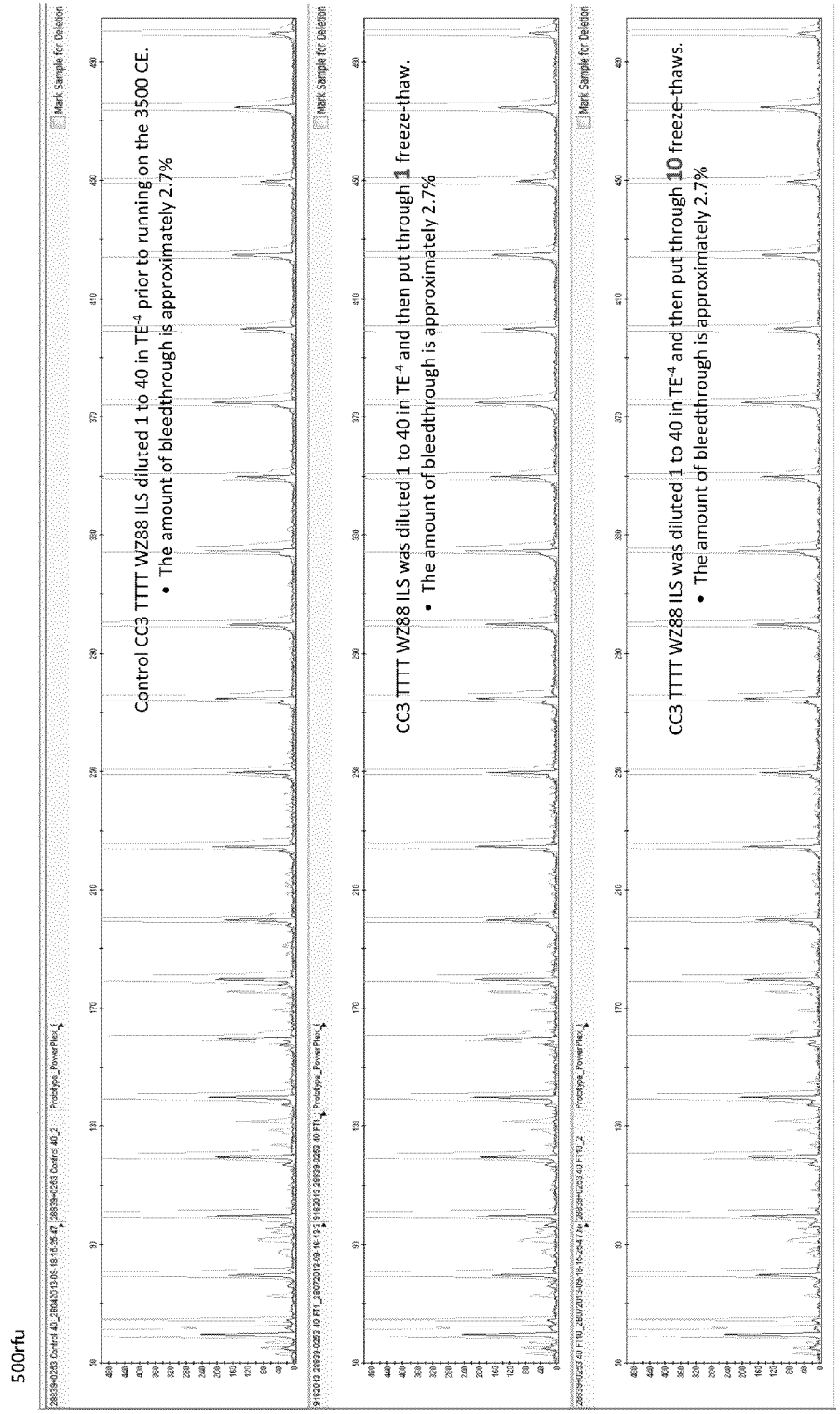
FIG. 28 demonstrates that the CC3-TTTT-WZ88 ILS (diluted) experienced approximately 3% bleedthrough after 1 or 10 freeze-thaw cycles.
Figure 29:
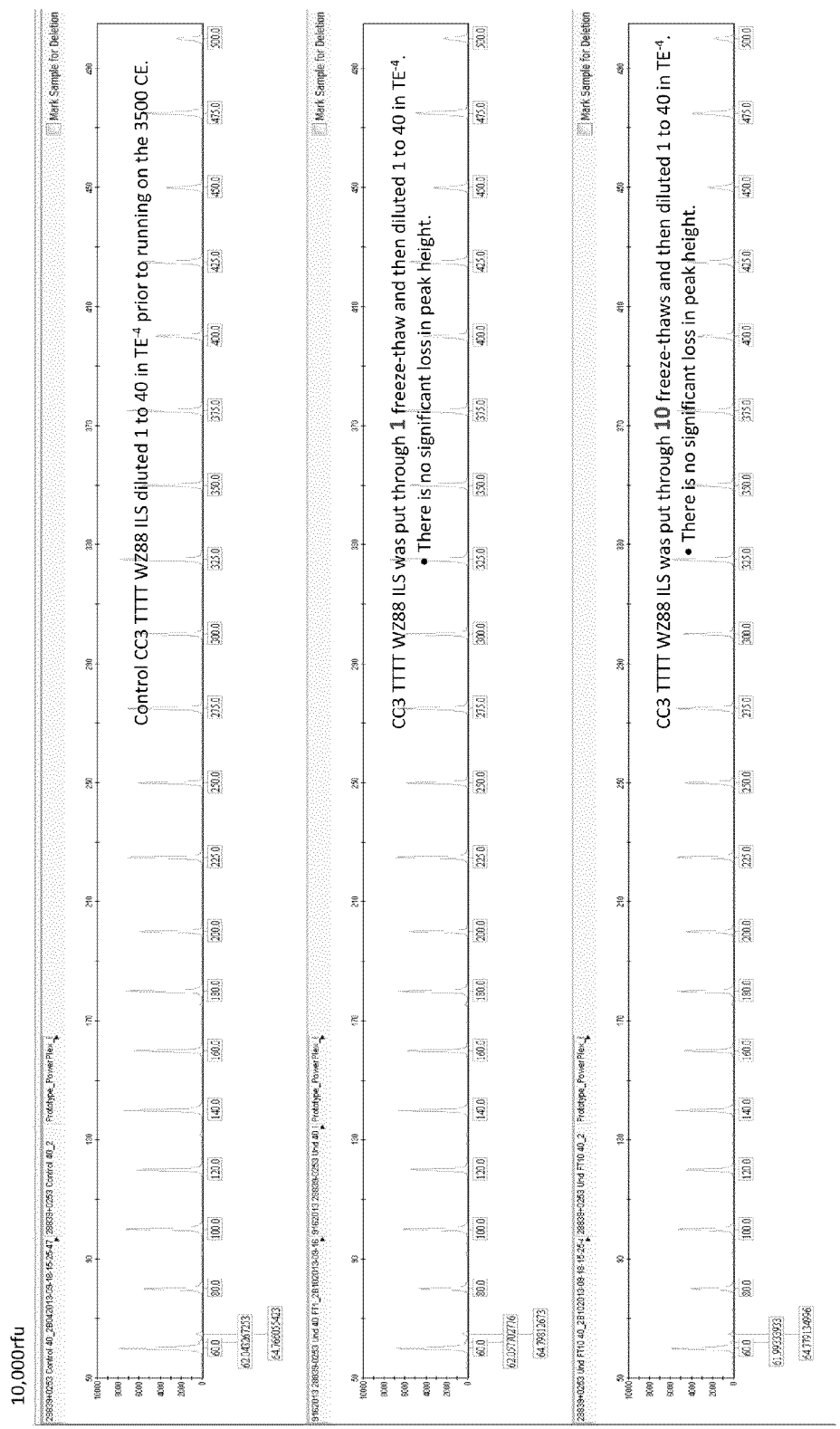
FIG. 29 demonstrates that the CC3-TTTT-WZ88 ILS (undiluted) experienced no significant loss in peak height after 1 or 10 freeze-thaw cycles.
Figure 30:
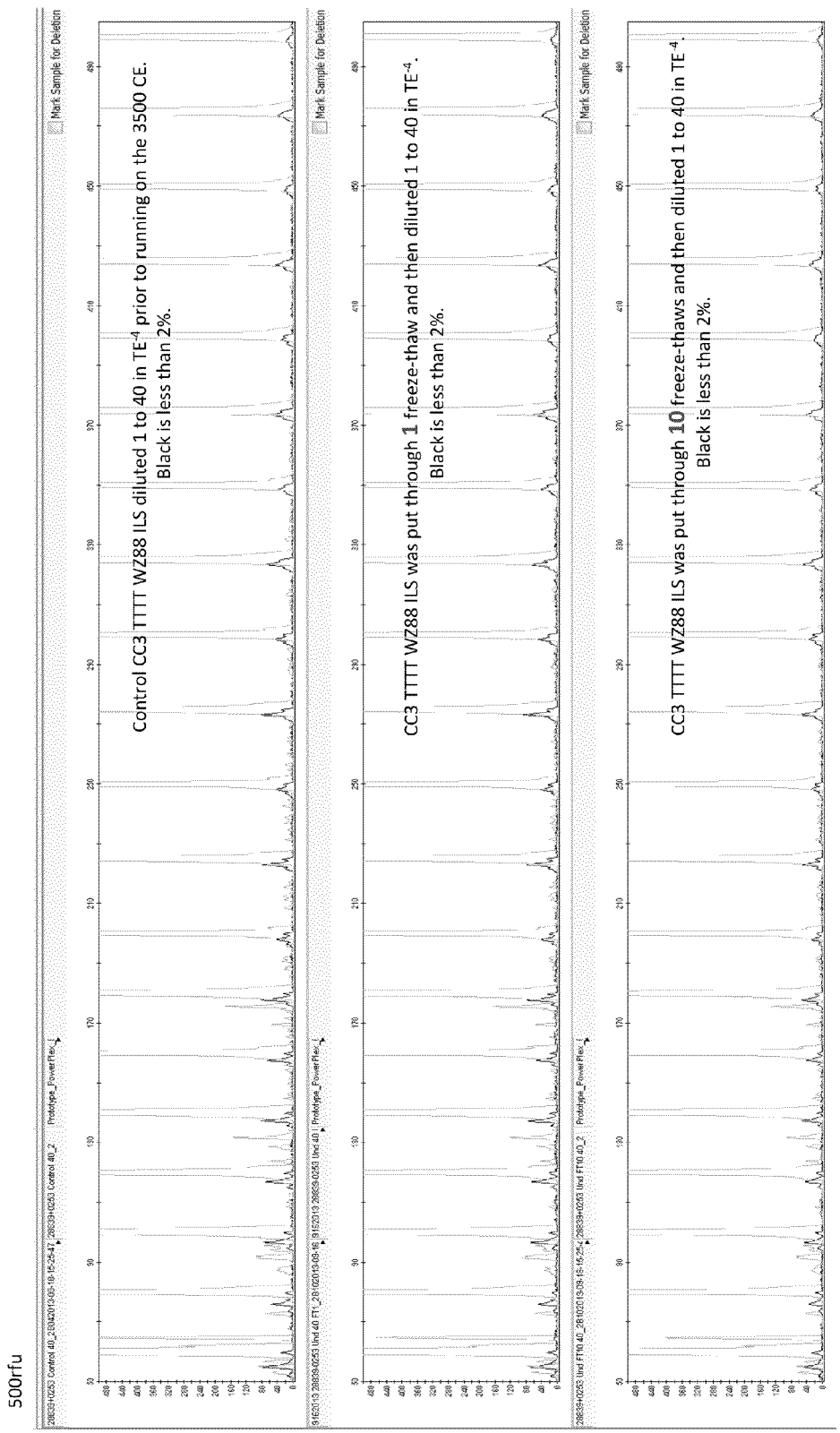
FIG. 30 demonstrates that the CC3-TTTT-WZ88 ILS (undiluted) experienced approximately 2% black into orange after 1 or 10 freeze-thaw cycles.
Figure 31:
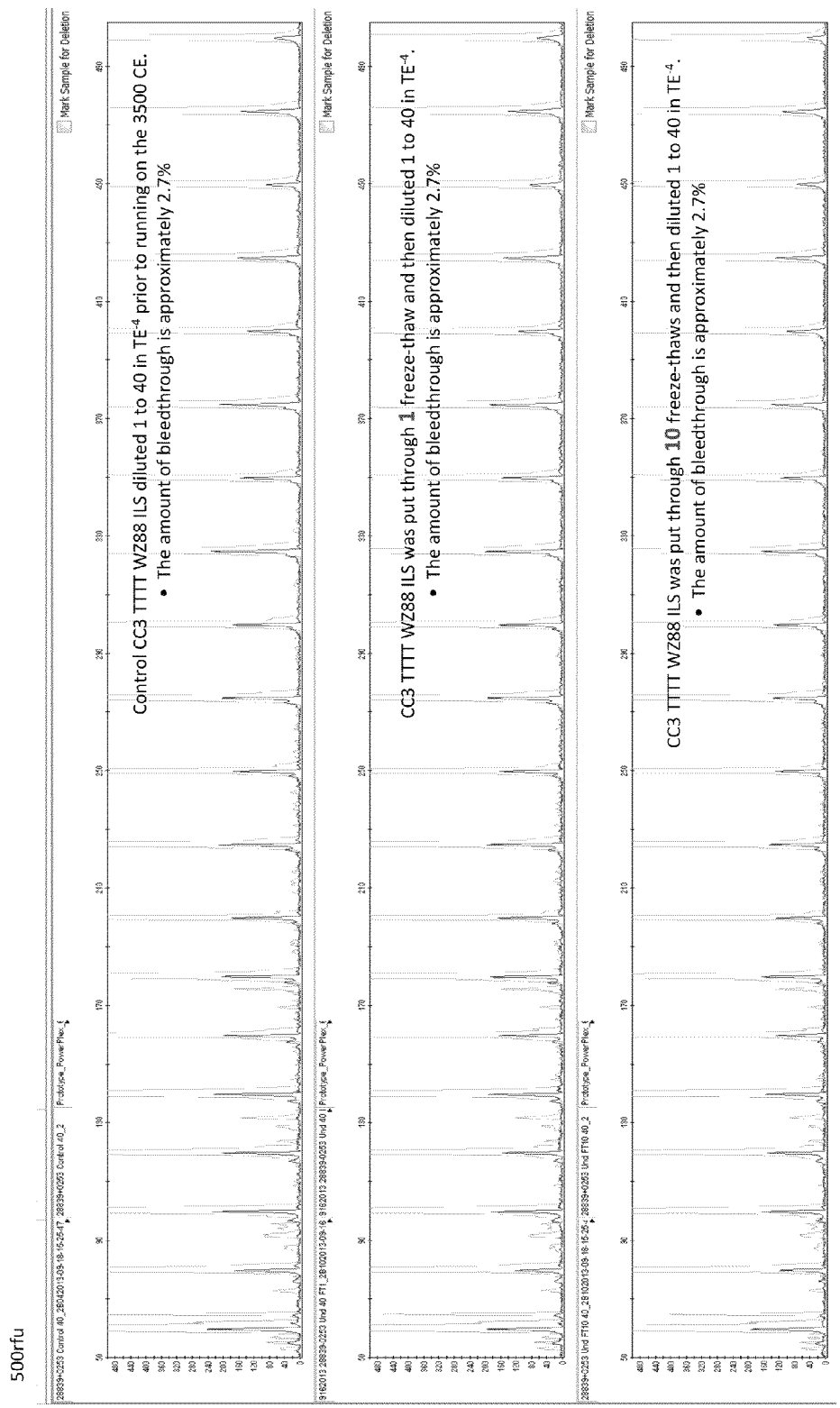
FIG. 31 demonstrates that the CC3-TTTT-WZ88 ILS (undiluted) experienced approximately 3% bleedthrough after 1 or 10 freeze-thaw cycles.
Figure 32:
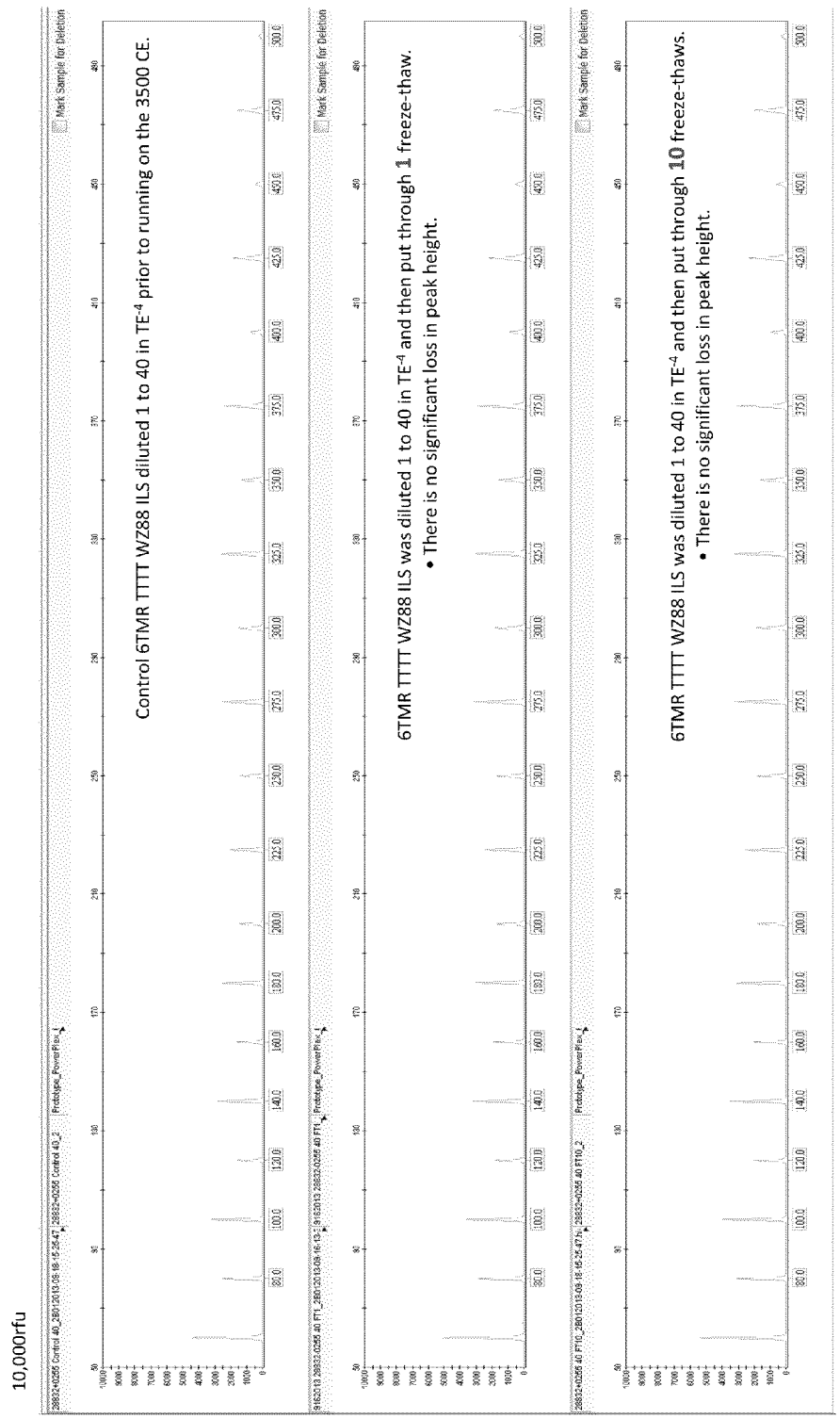
FIG. 32 demonstrates that the 6-TMR-TTTT-WZ88 ILS (diluted) experienced no significant loss in peak height after 1 or 10 freeze-thaw cycles.
Figure 33:
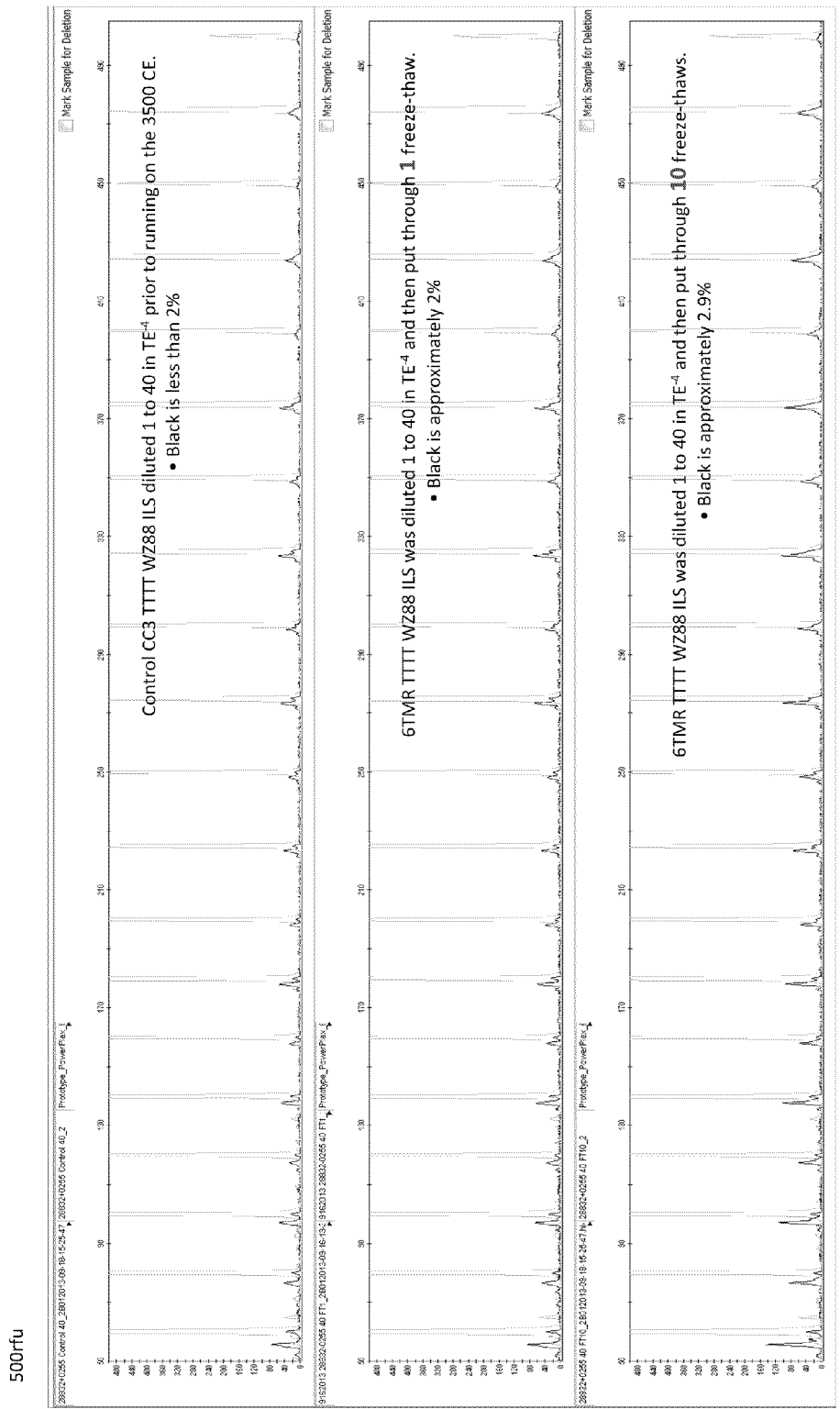
FIG. 33 demonstrates that the 6-TMR-TTTT-WZ88 ILS (diluted) experienced approximately 2% or 3% black into orange after 1 or 10 freeze-thaw cycles, respectively.
Figure 34:
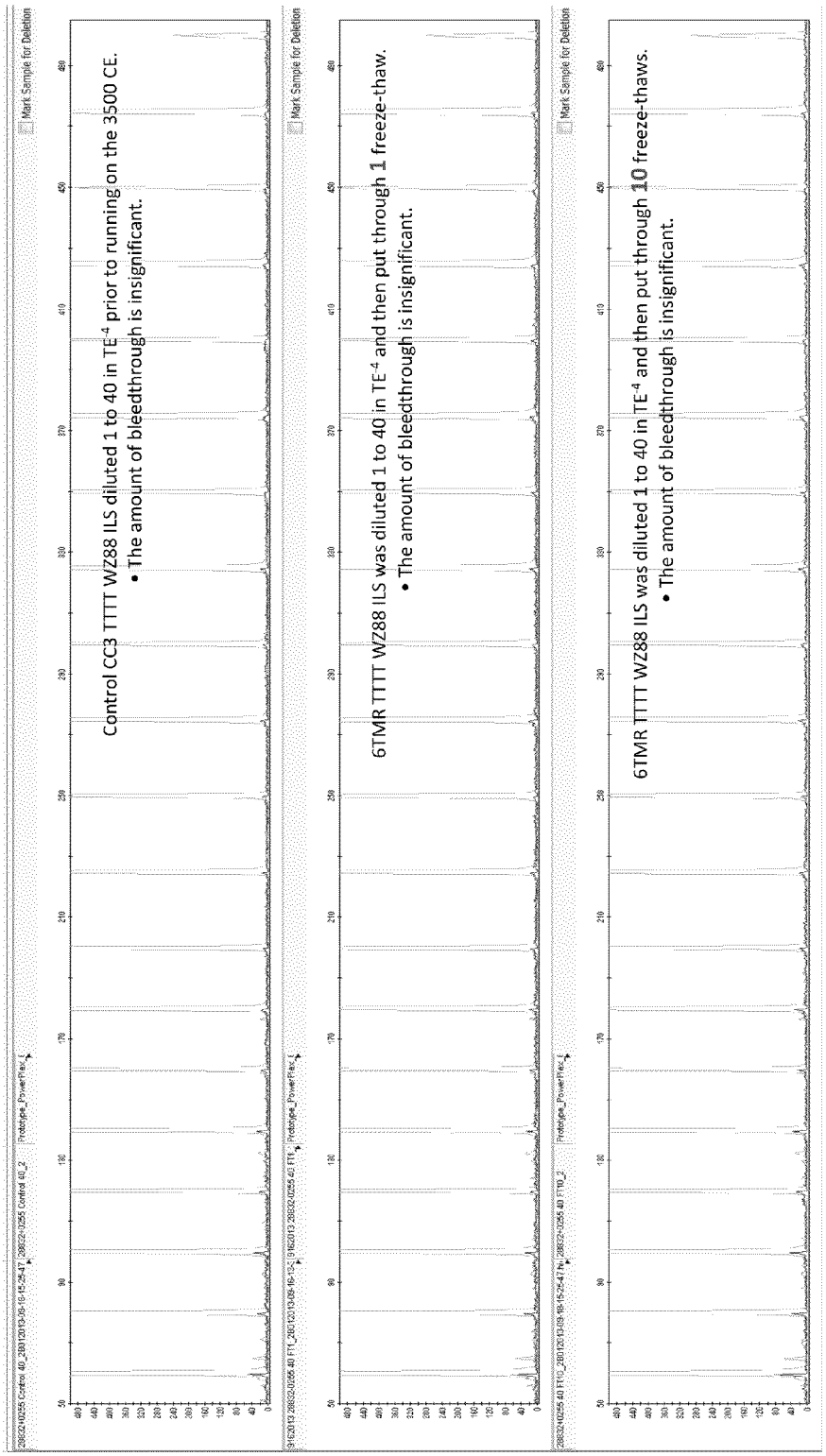
FIG. 34 demonstrates that the 6-TMR-TTTT-WZ88 ILS (diluted) experienced an insignificant amount of bleedthrough after 1 or 10 freeze-thaw cycles.
Figure 35:
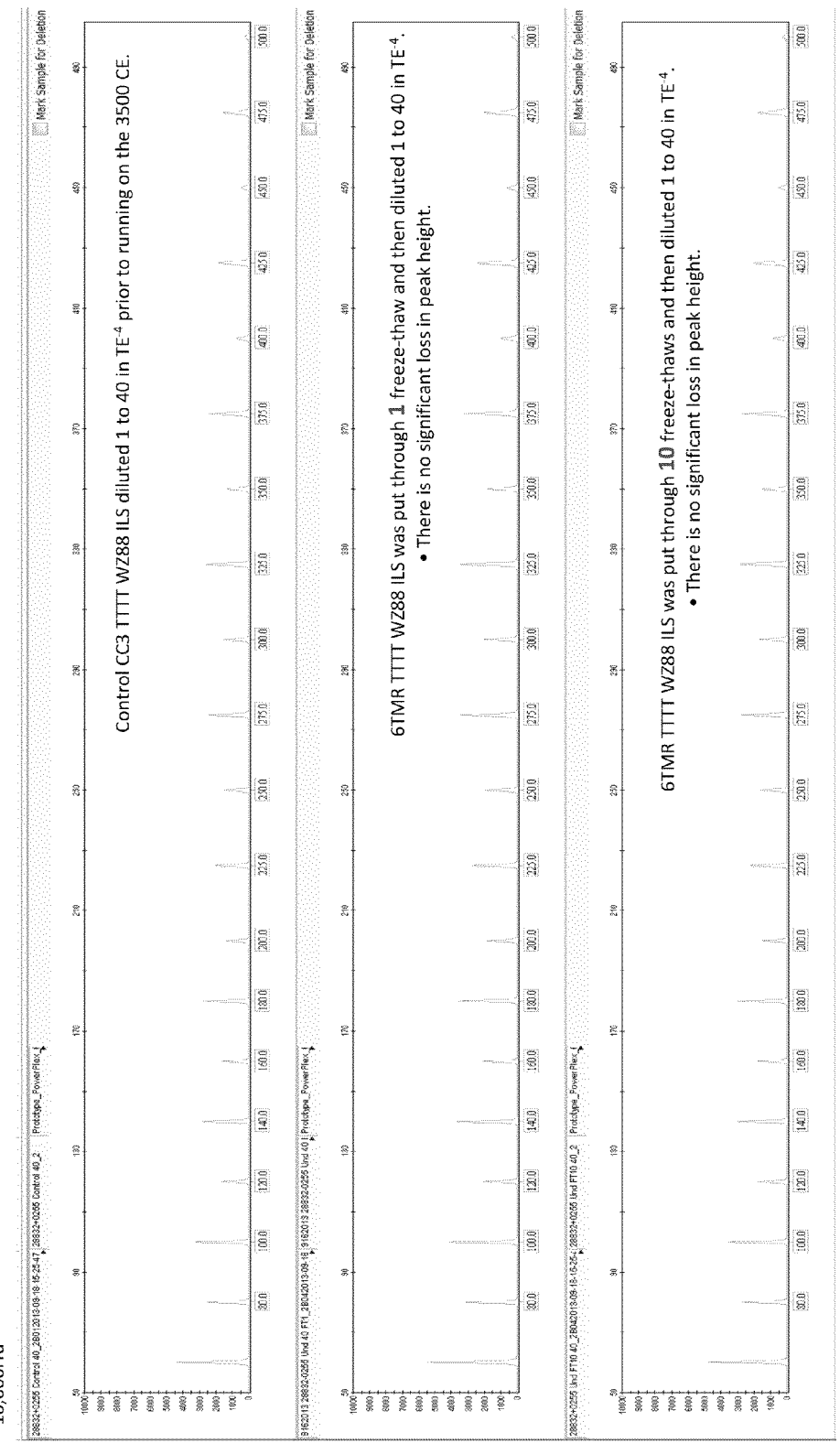
FIG. 35 demonstrates that the 6-TMR-TTTT-WZ88 ILS (undiluted) experienced no significant loss in peak height after 1 or 10 freeze-thaw cycles.
Figure 36:
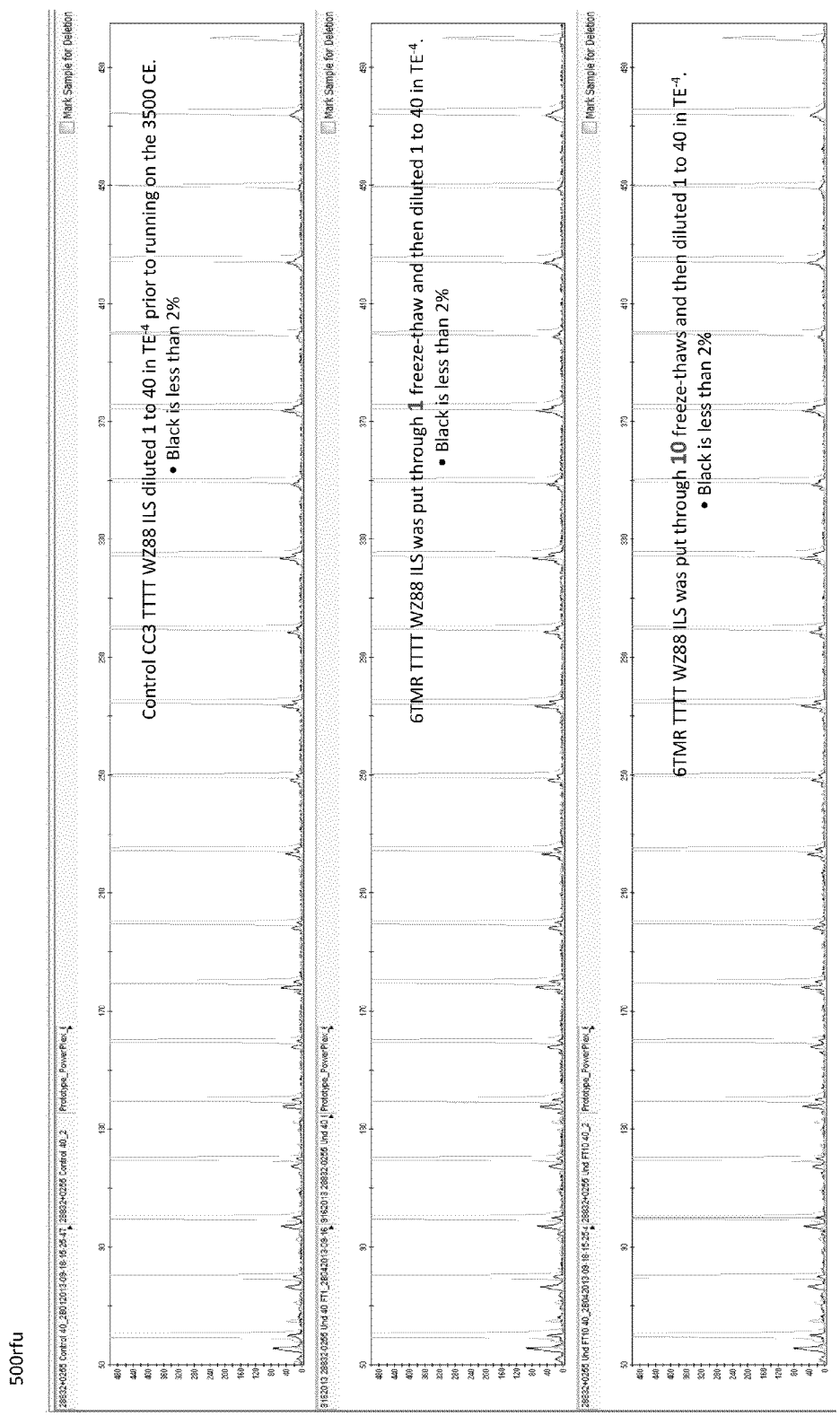
FIG. 36 demonstrates that the 6-TMR-TTTT-WZ88 ILS (undiluted) experienced approximately 2% black into orange after 1 or 10 freeze-thaw cycles.
Figure 37:
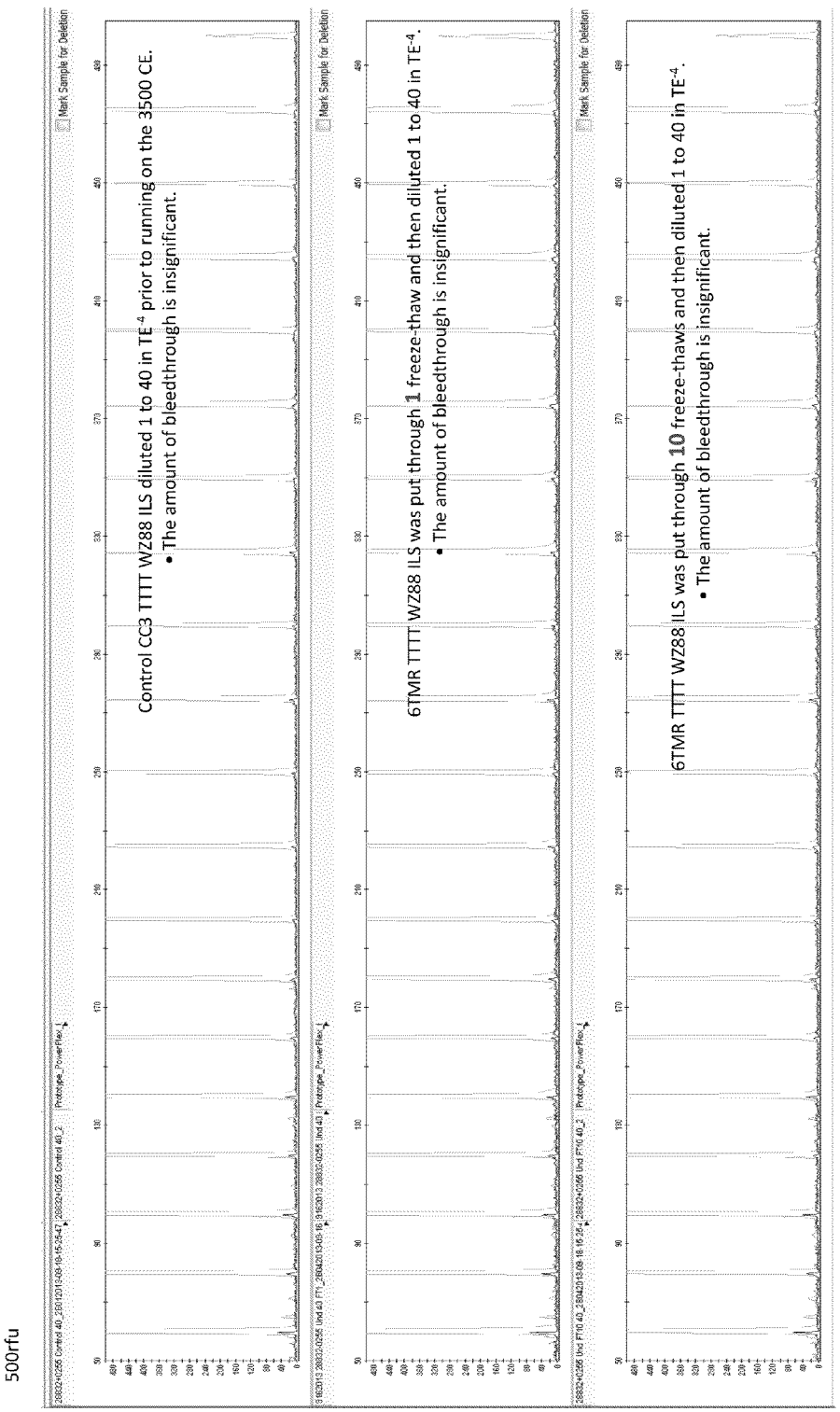
FIG. 37 demonstrates that the 6-TMR-TTTT-WZ88 ILS (undiluted) experienced an insignificant amount of bleedthrough after 1 or 10 freeze-thaw cycles.

Additional compounds useful in the present invention are shown in FIG. 13.

In some embodiments, the present invention provides a compound according to Formula (III):

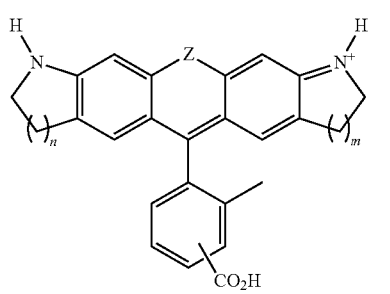

(III)

wherein
Z is $Si(R_{11})(R_{12})$ or $Ge(R_{11})(R_{12})$;
each $R_{11}$ and $R_{12}$ are independently selected from $C_{1-10}$ linear, branched or cyclic alkyl, $C_{1-10}$ alkyl interrupted with one or more heteroatoms, $C_{6-10}$ aryl, heteroaryl, or $R_{11}$ and $R_{12}$ may together form a ring.
and
m and n are independently an integer from 1 to 3

In some embodiments, the present invention provides a compound according to Formula (IV):

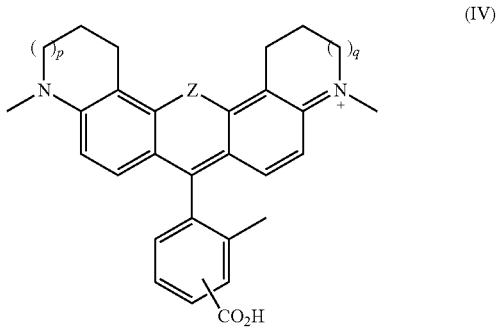

(IV)

wherein
Z is $Si(R_{11})(R_{12})$ or $Ge(R_{11})(R_{12})$;
each $R_{11}$ and $R_{12}$ are independently selected from $C_{1-10}$ linear, branched or cyclic alkyl, $C_{1-10}$ alkyl interrupted with one or more heteroatoms, $C_{6-10}$ aryl, heteroaryl, or $R_{11}$ and $R_{12}$ may together form a ring. and
p and q are independently an integer from 1 to 3.

In some embodiments, the present invention provides a compound according to Formula (V):

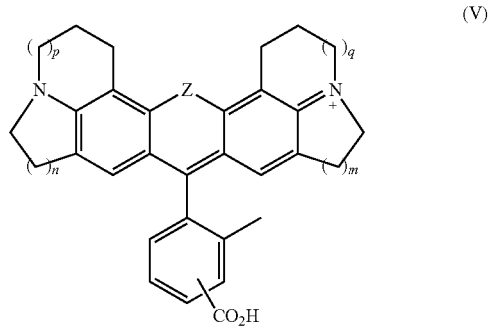

(V)

wherein
Z is $Si(R_{11})(R_{12})$ or $Ge(R_{11})(R_{12})$;
each $R_{11}$ and $R_{12}$ are independently selected from $C_{1-10}$ linear, branched or cyclic alkyl, $C_{1-10}$ alkyl interrupted with one or more heteroatoms, $C_{6-10}$ aryl, heteroaryl, or $R_{11}$ and $R_{12}$ may together form a ring; and
n, m, p and q are independently an integer from 1 to 3.

In some embodiments, a compound according to the present invention is part of an ET cassette.

The dyes of the present invention are fluorescent in the near-infrared range. In some embodiments, the dyes fluoresce at from about 650 to about 900 nanometers or about 700 to about 800 nanometers.

Synthesis

Figure 10:
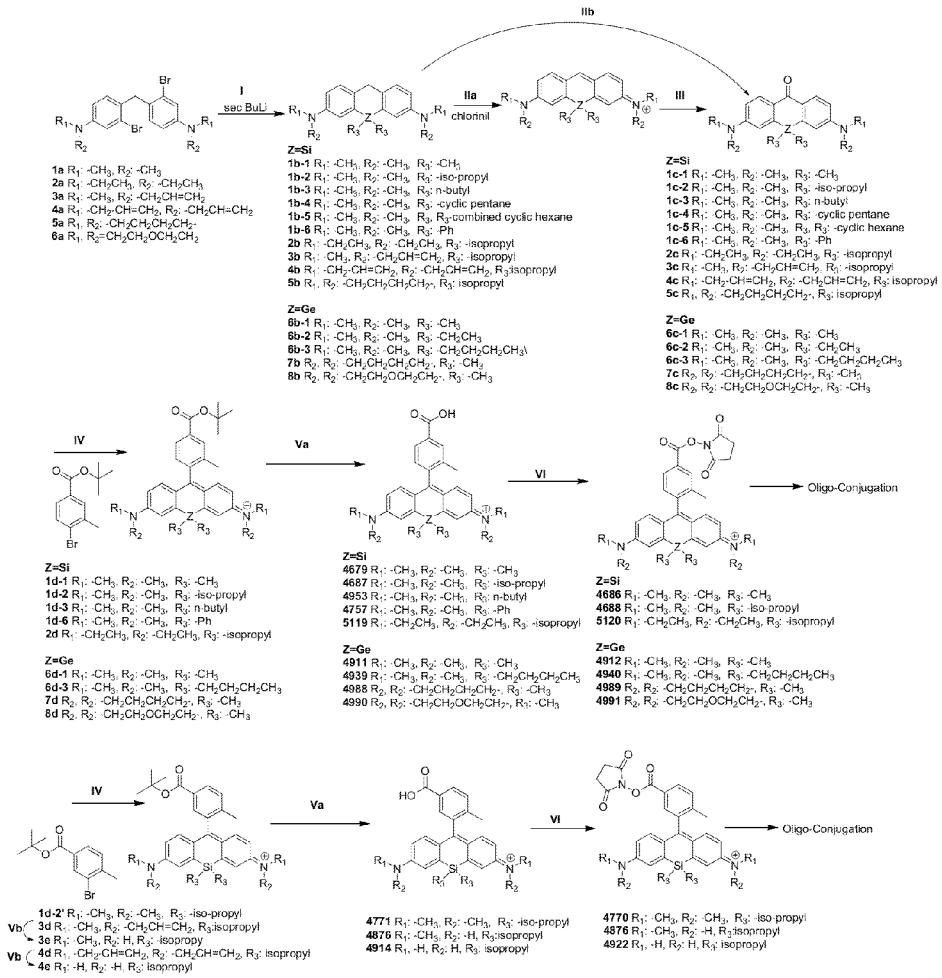
FIG. 10 illustrates a synthetic route to compounds according to the present invention.
Figure 11:
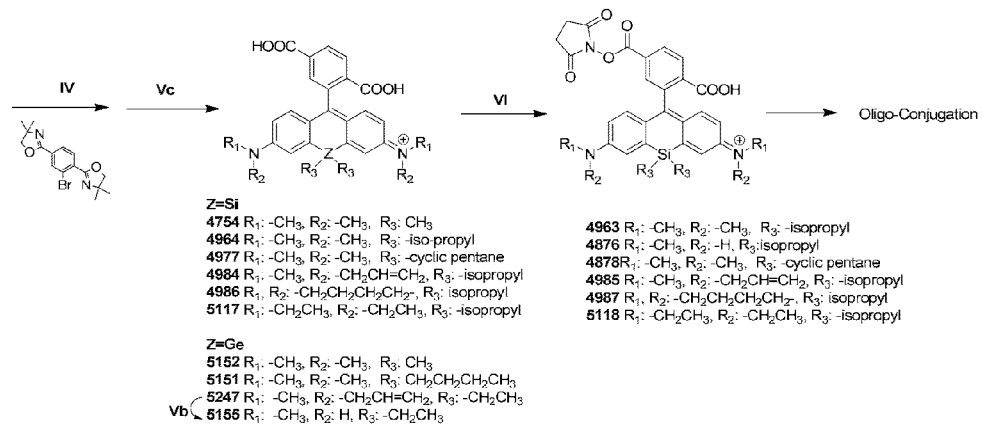
FIG. 11 illustrates a synthetic route to compounds according to the present invention.

Compounds according to the invention may be synthesized in a variety of ways including those shown in FIGS. 10 and 11 and described in the Examples. In general, 4,4'-methylenebis (3-bromo-N,N-dialkylaniline derivatives (1a-6a) were made by reacting 3-bromo-N,N-dialkylaniline with aldehyde in acetic acid. The dibromide compounds (1a-6a) were then lithiated with sec-BuLi in THF at −78° C. followed by addition of dialkyl silica dichloride or dialkyl germanium dichloride to obtain Si- or Ge-ring fused compounds 1b-8b. Compounds 1b-8b were then oxidized by excess chlorinil to form deep blue xanthene dye intermediates. Without isolation, the xanthene intermediates were further treated with chlorinil in basic aqueous solution to get the critical ring-fused ketone intermediates 1c-8c. t-Butyl 4-bromo-3-methylbenzoate was lithiated with sec-BuLi in dry THF at −78° C. and then reacted with the ring fused ketones 1c-8c and then treated with 1N HCl to obtain t-butyl ester of 5-carboxylic acid Si/Ge rhodamines 1d-8d. The t-butyl esters 1d-8d were removed by TFA and purified by HPLC to give the final 5-carboxylic acid Si-/Ge-rhodamines. 6-Carboxylic acid Si-/Ge-rhodamines were made by employing the same method using t-butyl 3-bromo-4-methyl benzoate as reagent. Bis-carboxyl acid Si-/Ge-rhodamines were also made by the above similar method using 2,2'-(2-bromo-1,4-phenylene)bis(4,4-dimethyl-4,5-dihydrooxazole) as reagent, and the deprotection of oxazole or esters steps were conducted in 2N HCl/CAN under reflux or at 80° C. with microwave. All Si-/Ge-dye free acids were converted to active NHS ester by reacting with TSTU in DMF in the presence of DIPEA.

As can be appreciated by the skilled artisan, alternative methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Labeled Substances

Briefly, the dyes of the present invention may be used as labeling agents which allow for the detection of a composition of matter. The dyes of the present invention can be used to label a broad range of substances, including but not limited to, biomolecules such as polypeptides, polypeptide-based toxins, amino acids, nucleotides, polynucleotides including DNA and RNA, lipids, carbohydrate, and enzyme substrates. Additionally, the compounds may be used to label haptens, small molecules, drugs, drug compounds, ion-complexing agents, such as metal chelators, microparticles, synthetic or natural polymers, cells, viruses, other fluorescent molecules or surfaces. The resulting labeled substances may be referred to as conjugates or tracers.

In some aspects, the dyes can be conjugated with a nucleoside, nucleotide or a polynucleotide. The dyes of the invention may be conjugated with nucleoside, nucleotide or polynucleotide in any way known to one of ordinary skill in the art such as through a phosphoramidite, an activated ester or a reactive platinum complex.

Kits

One aspect of the invention is the formulation of kits that facilitate the practice of various assays using any of the dyes of the invention, as described above. The kits of the invention typically comprise a colored or fluorescent dye of the invention, either present as a chemically reactive label useful for preparing dye-conjugates or present as a dye-conjugate where the conjugated substance is a specific binding pair member, or, for instance, a nucleoside, nucleotide, oligonucleotide, polynucleotide, peptide, protein or small molecule, e.g. drug or drug compound. The kit optionally further comprises one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, constructs for expression of fusion proteins, e.g., fusion proteins comprising a luciferase or HaloTag® protein fused to a protein or target of interest, fusion proteins, or instructions for carrying out an assay of the invention.

In some embodiments, a kit of the invention includes one or more locus-specific primers. In some embodiments, a kit of the invention includes an internal lane standard (ILS) which comprises a dye of the present invention. Instructions for use optionally may be included. Other optional kit components may include an allelic ladder directed to each of the specified loci, a sufficient quantity of enzyme for amplification, amplification buffer to facilitate the amplification, loading solution for preparation of the amplified material for electrophoresis, genomic DNA as a template control, a size marker to insure that materials migrate as anticipated in the separation medium, and a protocol and manual to educate the user and to limit error in use. The amounts of the various reagents in the kits also can be varied depending upon a number of factors, such as the optimum sensitivity of the process. It is within the scope of this invention to provide test kits for use in manual applications or test kits for use with automated detectors or analyzers.

In other embodiments, the kit also includes a genetically-modified cell or a vector for gene fusion, e.g., fusion comprising a luciferase or HaloTag® protein fused to a protein or target of interest. Instructions for use optionally may be included.

The following Examples are intended to illustrate the invention above and should not be construed as to narrow its scope. One skilled in the art will readily recognize that the Examples may suggest other ways in which the present invention could be practiced. It should be understood that variations and modifications may be made while remaining within the scope of the invention.

EXAMPLES

Example 1

Syntheses of diisopropyl-Si-tetramethylrhodamine 5-COOH (PBI-4687) and diisopropyl-Si-tetramethylrhodamine 5-SE (PBI-4688)

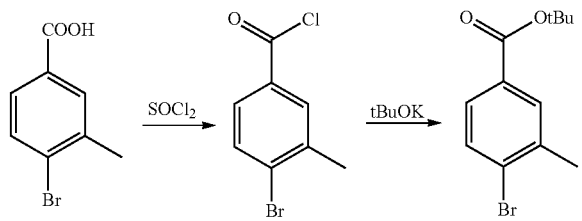

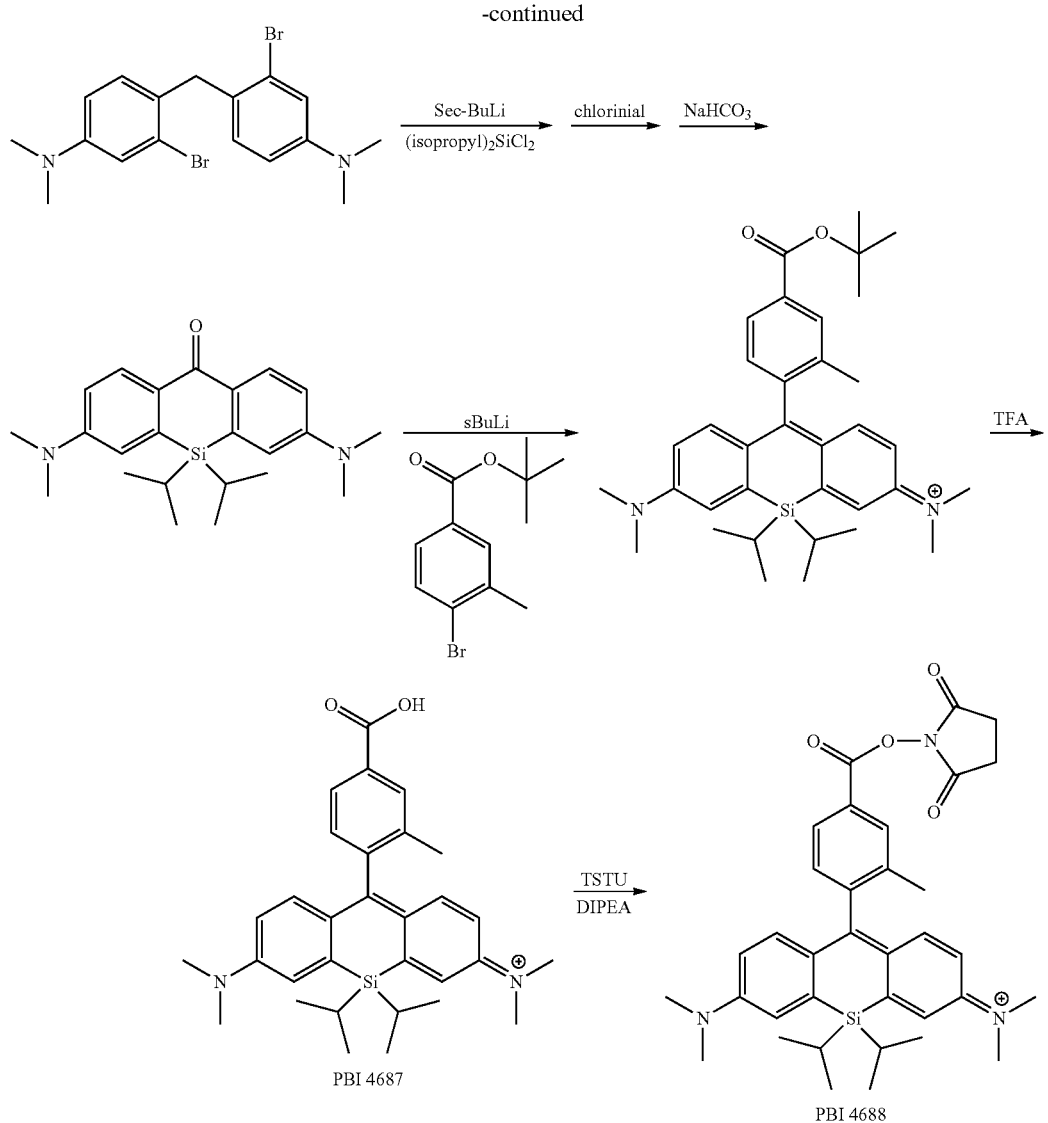

Synthesis of 4-bromo-3-methylbenzoyl chloride

A mixture of 4-bromo-3-methylbenzoic acid (5.0 g, 23.25 mmol) and thionylchloride (50 ml) was refluxed for 5 hours. After removal of thionyl chloride, the residue was dried under high vacuum and used in next step without further purification.

Synthesis of tert-butyl 4-bromo-3-methylbenzoate

To a solution of the above 4-bromo-3-methylbenzoyl chloride residue in THF (100 mL), a solution of potassium ten-butoxide (6.0 g, 53.5 mmol) in THF (60 mL) was added dropwise at 0° C. under nitrogen. The mixture was stirred at room temperature for 30 min. The reaction mixture was poured into ice-cold water and extracted with ethyl acetate. The organic layer was washed with water and brine and dried over $Na_2SO_4$. The compound was purified by silica column chromatography using heptane and ethyl acetate as eluent to give a yield of 96%. $^1$HNMR (300 MHz, $CD_2Cl_2$): δ 7.88 (s, 1H), 7.53-7.7 (m, 2H), 2.42 (s, 3H, $CH_3$), 1.57 (s, 9H, $CH_3$); MS (m/e): calculated 215.96/213.96 (1:1). found 215.0/217.0 (1:1), for [M+H−tBu]$^+$.

Synthesis of 3,7-bis(dimethylamino)-5,5-diisopropyldibenzo[b,e]silin-10(5H)-one To the solution of 4,4'-methylene-bis(3-bromo-N,N-dimethylaniline) (6.0 g, 14.56 mmol) in anhydrous THF (50 mL), 2.5 M sec-BuLi (44 mmol) at −78° C. was added, and the mixture was stirred for 30 min. At the same temperature, a solution of Si(i-propyl)$_2$Cl$_2$ (5.39 g, 30 mmol) in anhydrous THF (15 mL) was slowly added. The mixture was warmed to room temperature and stirred for 1 h. The reaction was quenched by addition of 2 N HCl (7 ml), and the mixture was neutralized with $NaHCO_3$ and extracted with $CH_2Cl_2$. The organic layer was washed with brine and dried over $Na_2SO_4$. The residue was dissolved in methylene chloride/acetone (150 mL/150 ml). To this solution, the sufficient chlorinil (5 eq.) was added, and the resulted mixture was stirred overnight. The mixture was diluted with $CH_2Cl_2$ (200 mL), filtered through glasswool, and the filtrate was evaporated to dryness. The residue was purified by silica column chromatography using heptane/methylene chloride/ethyl acetate as eluent to give light yellow compound. $^1$HNMR (300 MHz, CD$_2$Cl$_2$): δ 8.30 (d, 2H), 6.8-6.90 (m, 4H), 3.10 (s, 12H, NCH$_3$), 1.4-1.6 (m, 2H, SiCH), 1.04 (d, 12H, CH$_3$); MS (m/e): calculated 380.23. found 381.33 for [M+H]$^+$.

Synthesis of PBI-4687

To the solution of tert-butyl 4-bromo-3-methylbenzoate (0.36 g, 1.31 mmol) and anhydrous THF (8 ml), 1.4 M sec-BuLi (0.84 ml, 1.18 mmol) were added at −78° C. under nitrogen, and the mixture was stirred for 30 min. At the same temperature, 3,7-bis(dimethylamino)-5,5-diisopropyldibenzo[b,e]silin-10(5H)-one (50 mg, 0.13 mmol) dissolved in anhydrous THF (5 mL) was slowly added. The mixture was warmed to room temperature, stirred for 1 h, 2 N HCl aq. (5 mL) added, and the resultant mixture stirred for 10 minutes. After removal of THF, 5 ml of water was added, the mixture extracted with CH$_2$Cl$_2$, and the organic layer washed with brine and dried over Na$_2$SO$_4$. After the solvent was removed, the residue was purified with silica chromatography using methylene chloride/methanol as eluent. The resulting product was dissolved in 20 ml of CH$_2$Cl$_2$/TFA (1:1) in the presence of 50 ul of triisopropylsilane and stirred for 1 hour. The solvent was removed, and the product purified by HPLC using 0.1% TFA/acetonitrile as eluent. $^1$HNMR (300 MHz, DMSO): δ 7.99 (s, 1H), 7.92 (d, 1H), 7.2-7.3 (m, 3H), 6.8-7.0 (m, 4H), 3.28 (s, 12H, NCH$_3$), 2.40 (s, 3H, CH$_3$), 1.67 (m, 2H, CHSi), 1.0 (dd, 12H, SiCH3); MS (m/e): calculated 499.28. found 4499.6 for M.

Synthesis of PBI-4688

To the solution of PBI-4687 (60 mg, 97.76 umol) and N,N,N',N'-tetramethyl-O—(N-succinimidyl)uromium tetrafluoroborate (TSTU, 58.86 mg, 195.52 umol) in 10 ml of anhydrous DMF, DIPEA (63.2 mg, 488.8 umol) was added. The resultant mixture was stirred for 1 hour at room temperature. The mixture was acidified with acetic acid, and the product purified by HPLC using 0.1% TFA/acetonitrile as eluent. MS (m/e). found 596.6. calculated 596.29 for M$^+$; HPLC purity 95.6% at 647 nm.

Example 2

Syntheses of diisopropyl-Si-tetramethyl rhodamine 6-COOH (PBI-4770) and diisopropyl-Si-tetramethyl rhodamine 6-SE (PBI-4771)

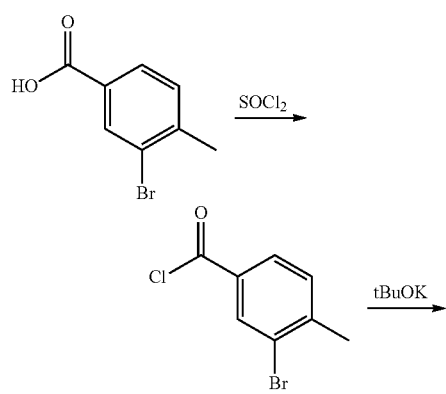

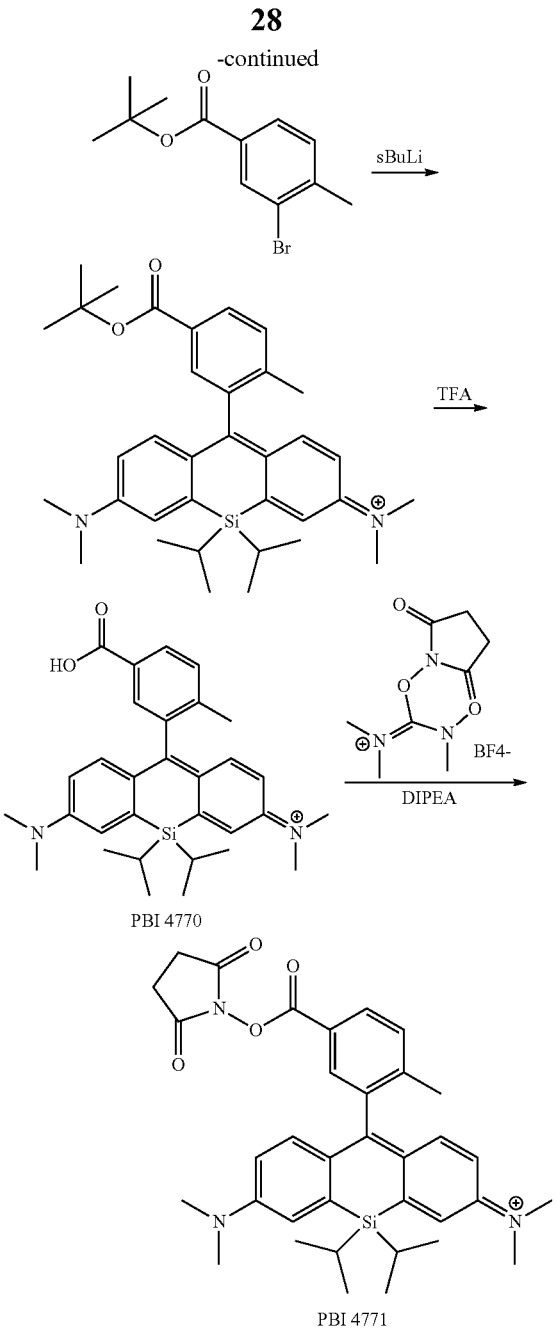

Synthesis of 3-bromo-4-methylbenzoyl chloride

The mixture of 4-bromo-3-methylbenzoic acid (10.0 g, 46.5 mmol) and thionylchloride (100 ml) was refluxed for 5 hours. After removal of thionyl chloride, the residue was dried under high vacuum and used in next step without further purification Synthesis of tert-butyl 3-bromo-4-methylbenzoate To a solution of the above 4-bromo-3-methylbenzoyl chloride residue in THF (100 mL), a solution of potassium ten-butoxide (12.0, 107 mmol) in THF (100 mL) was added dropwise at 0° C. under nitrogen. The mixture was stirred at room temperature for 30 minutes. The reaction mixture was poured into ice-cold water and extracted with ethyl acetate.

The organic layer was washed with water and brine and dried over Na$_2$SO$_4$. The compound was purified by silica column chromatography using heptane and ethyl acetate as eluent to give a yield of 82%. $^1$HNMR (300 MHz, CD$_2$Cl$_2$): δ 8.18 (s, 1H), 7.83 (d, 1H), 7.31 (d, 1H), 2.44 (s, 3H, CH$_3$), 1.59 (s, 9H, CH$_3$); MS (m/e). found 215.0/217.0 (1:1). calculated 215.96/213.96 (1:1) for [M+H−tBu]$^+$.

Synthesis of PBI-4770

To the solution of tert-butyl 4-bromo-3-methylbenzoate (0.36 g, 1.31 mmol) in an anhydrous THF (8 ml), 1.4 M sec-BuLi (0.94 ml, 1.31 mmol) was added at −78° C. under nitrogen, and the mixture stirred for 30 min. At the same temperature, 3,7-bis(dimethylamino)-5,5-diisopropyldibenzo[b,e]silin-10(5H)-one (50 mg, 0.13 mmol) dissolved in anhydrous THF (5 mL) was slowly added. The mixture was warmed to room temperature and stirred for 1 h, 2 N HCl aq. (5 mL) added, and the resultant mixture stirred for 10 minutes. After removal of THF, 5 ml of water was added, the mixture extracted with CH$_2$Cl$_2$, and the organic layer washed with brine and dried over Na$_2$SO$_4$. The solvent was removed, and without further purification, the residue dissolved in 20 ml of CH$_2$Cl$_2$/TFA (1:1) in the presence of 50 ul of triisopropylsilane and stirred for 1 hour. The solvent was removed, and the product purified by HPLC using 0.1% TFA/acetonitrile as eluent. $^1$HNMR (300 MHz, DMSO): δ 8.0 (s, br, 1H), 7.80 (d, br, 1H), 7.4-7.6 (m, 2H), 7.2 (s, 1H), 6.8-7.0 (m, 4H), 3.25 (s, 12H, NCH$_3$), 2.40 (s, 3H, CH$_3$), 1.67 (m, 2H, CHSi), 1.0 (dd, 12H, SiCH3); MS (m/e): calculated 499.28. found 499.6 for M.

Synthesis of PBI-4771

To the solution of PBI-4677 (150 mg, 0.244 mmol) and N,N,N',N'-tetramethyl-O—(N-succinimidyl)uromium tetrafluoroborate (TSTU, 147 mg, 0.488 mmol) in 10 ml of anhydrous DMF, DIPEA (158 mg, 1.22 mmol) was added. The resultant mixture was stirred for 1 hour at room temperature. The mixture was acidified with acetic acid, and the product purified by HPLC using 0.1% TFA/acetonitrile as eluent. MS (m/e). found 596.6. calculated 596.29 for M$^+$; HPLC purity 90.5% at 647 nm Example 3

Syntheses of dimethyl Ge-tetramethyl rhodamine 5-COOH (PBI-4911) and dimethyl Ge-tetramethyl rhodamine 5-COOH (PBI-4912)

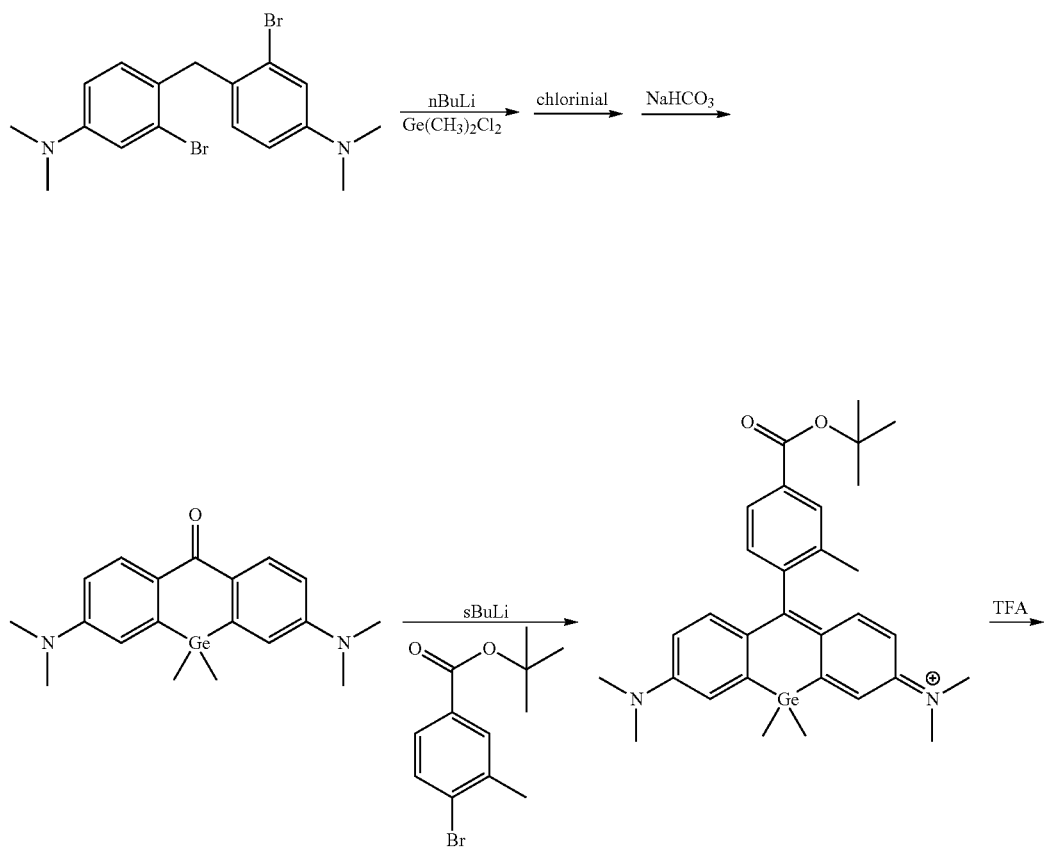

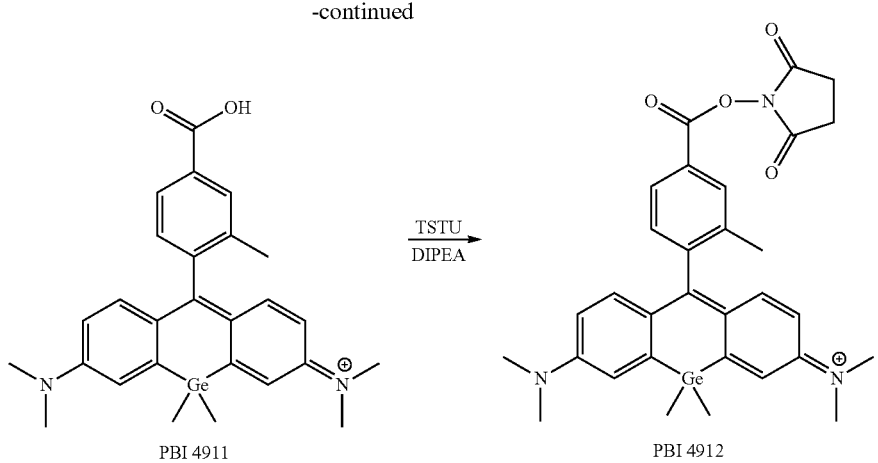

Synthesis of 3,7-bis(dimethylamino)-5,5-dimethyldibenzo[b,e]germin-10(5H)-one To the solution of 4,4'-methylene-bis(3-bromo-N,N-dimethylaniline) (2.0 g, 4.85 mmol) in anhydrous THF (50 mL), 1.4 M sec-BuLi (12.13 mmol) at −78° C. was added, and the mixture stirred for 30 min. At the same temperature, a solution of GeMe$_2$Cl$_2$ (1.26 g, 7.28 mmol) in anhydrous THF (15 mL) was slowly added. The mixture was warmed to room temperature and stirred for 1 h. The reaction was quenched by addition of 2 N HCl (7 ml), and the mixture neutralized with NaHCO$_3$ and extracted with CH$_2$Cl$_2$. The organic layer was washed with brine and dried over Na$_2$SO$_4$. To this solution, the sufficient chlorinil (5 eq.) was added, and the resultant mixture stirred for 2 hours. Acetone/saturated NaHCO3 (50 mL/100 ml) were added, and the mixture stirred overnight. The mixture was then diluted with CH$_2$Cl$_2$ (200 mL), filtered through glass wool, and the filtrate extracted three times with methylene chloride and evaporated to dryness. The residue was purified by silica column chromatography using heptane/methylene chloride/ethyl acetate as eluent to give light yellow compound. $^1$HNMR (300 MHz, CD$_2$Cl$_2$): δ 8.32 (d, 2H), 6.7-6.90 (m, 4H), 3.20 (s, 12H, NCH$_3$), 0.6 (d, 6H, CH$_3$); MS (m/e): calculated 370.11. found 371.0 for [M+H]$^+$.

Synthesis of PBI-4911

To the solution of tert-butyl 4-bromo-3-methylbenzoate (0.36 g, 1.31 mmol) in an anhydrous THF (8 ml), 1.4 M sec-BuLi (0.84 ml, 1.18 mmol) at −78° C. was added under nitrogen, and the mixture stirred for 30 min. At the same temperature, 3,7-bis(dimethylamino)-5,5-dimethyldibenzo[b,e]germin-10(5H)-one (50 mg, 0.13 mmol) dissolved in anhydrous THF (5 mL) was slowly added. The mixture was warmed to room temperature and stirred for 1 h, 2 N HCl aq. (5 mL) added, and the resultant mixture stirred for 10 minutes. After removal of THF, 5 ml of water was added, the mixture extracted with CH$_2$Cl$_2$, and the organic layer washed with brine and dried over Na$_2$SO$_4$. After the solvent was removed, the residue was purified with silica chromatography using methylene chloride/methanol as eluent. The resulting product was dissolved in 20 ml of CH$_2$Cl$_2$/TFA (1:1) in the presence of 50 ul of triisopropylsilane and stirred for 1 hour. The solvent was removed, and the product purified by HPLC using 0.1% TFA/acetonitrile as eluent. MS (m/e): calculated 488.19. found 487.8 for M.

Synthesis of PBI-4912

To the solution of PBI-4911 (60 mg, 97.76 umol) and N,N,N',N'-tetramethyl-O—(N-succinimidyl)uromium tetrafluoroborate (TSTU, 58.86 mg, 195.52 umol) in 10 ml of anhydrous DMF, DIPEA (63.2 mg, 488.8 umol) was added. The resultant mixture was stirred for 1 hour at room temperature. The mixture was acidified with acetic acid, and the product purified by HPLC using 0.1% TFA/acetonitrile as eluent. MS (m/e). found 586.4. calculated 585.26 for M$^+$; HPLC purity 95.6% at 647 nm.

Example 4

General Procedures for Use of Si-Xanthene Dye N-Hydroxysuccinimidyl Esters Conjugating to Oligonucleotides A. 1 µMole Scale 5'-amino labeled or internal amino-deoxyuridine oligonucleotide was synthesized on an ABI 394 DNA synthesizer (1 µmole) using 5' Amino modifier C6 TFA amidite from Glen Research or Aminoallyl-dU amidite from PBI. Deprotection in concentrated ammonium hydroxide overnight at 60° C. yielded the amino-labeled oligonucleotide. The resulting oligonucleotide was evaporated to dryness, redissolved in 1 ml 2M NaCl (performed for counter-ion exchange) and desalted on NAP-10 size exclusion cartridge (GE Healthcare). After desalting, the oligonucleotide was evaporated to dryness followed by re-dissolution in 200 µl 0.5M sodium carbonate buffer, pH 8.5. The succinimidyl ester dye (PBI-4688) was dissolved in DMF at a concentration of 20 µl/mg. Two 20 µl aliquots of the dye/DMF solution were added to the dissolved oligonucleotide, 30 minutes apart. After the second addition, the reaction was mixed for 1 hour. After one hour, it was diluted to 1 ml with water and desalted on a NAP-10 column (GE Healthcare). The NAP-10 eluate was purified by reversed phase HPLC on a Phenomonex Jupiter C18 column using an acetonitrile/0.1M TEAA buffer system. The HPLC purified oligonucleotide was evaporated to dryness redissolved in 0.01M triethylammonium bicarbonate and desalted on a NAP-10 column. After final desalt step, the oligonucleotide was evaporated to dryness.

B. 100 µmole scale

The 5'-amino labeled or internal amino-deoxyuridine oligonucleotide was synthesized on an AKTA OligoPilot (100

µmole) DNA synthesizer using 5' Amino modifier C6 TFA amidite from Glen Research or Aminoallyl dU amidite from PBI. Deprotection in concentrated ammonium hydroxide overnight at 60° C. yielded the 5'-aminohexyl labeled oligonucleotide. The resulting oligonucleotide was evaporated to dryness, redissolved in 75 ml 2M NaCl and desalted on a 500 ml G-25 column (GE Healthcare). After desalting, the oligonucleotide was evaporated to dryness followed by re-dissolution in 50 ml 0.5M sodium carbonate buffer, pH 8.5. The succinimidyl ester dye (PBI-4688) was dissolved in DMF at a concentration of 20 µl/mg. 2400 µl of the dye/DMF solution was added dropwise to the dissolved oligonucleotide. The reaction was mixed for 1 hour. The dye conjugated oligonucleotide was neutralized with sodium acetate, pH 5.5 solution and precipitated from 2× volume of ethanol. The precipitated oligonucleotide was centrifuged at 9000 rpm for 60 minutes. The supernatant was decanted to waste. The resulting solid was dissolved in 70 ml water and purified by ion-exchange chromatography. The oligonucleotide was concentrated and desalted using tangential flow ultrafiltration and subsequently evaporated to dryness.

Example 51

Lane Standard for Multiplex PCR of STRs Using the Dyes of the Present Invention

Experiments were conducted during development of embodiments of the present invention to determine the energy transfer characteristics of exemplary dyes PBI-4686 and PBI-4688 for potential use in an internal lane standard for use in multiplex PCR of STRs (short tandem repeats).

Oligonucleotides (oligos) were made as energy transfer (ET) oligos for use with JOE or 6-FAM donor dye using the dyes, PBI-4686 and PBI-4688. The oligos were made with either a 3 nucleotide spacer (JOE and 6-FAM donor dye) or 5 nucleotide spacer (JOE donor).

The oligos were then used in amplification reactions that can be used in spectral calibrations placed on the ANYDYE dye set on the ABI 3500 instrument or the G5 dye set on the ABI 3500 or 3130 instruments.

The following amplification reaction conditions were used for each reaction:
Nanopure water: 90.5 ul
25×SSB Buffer: 4.0 ul
100 uM Labeled Oligo: 1.0 ul
100 uM Unlabeled Oligo: 1.0 ul
Taq DNA Polymerase (5 U/ul): 3.0 ul.

The reaction mix was vortexed and dispensed into wells of a 96-well plate. 50 ng/µl (0.5 ul) of plasmid DNA was then added to each well. Each well contained a different labeled oligo and plasmid size. When running a spectral calibration on the ABI 3500 instrument, each dye has to be within a specific size range and dye order (SEE FIG. 5 for example). Therefore, all of the dyes of the present invention would have the same size, but all of the other dye-labeled oligos (colors) would have to be a separate size. All dyes colors must be in a specific order for the spectral calibration to obtain a passing Q value. Additionally, the plasmids are added, separately, to get a range of sizes for an accurate evaluation on the dyes on CE instruments.

The reactions were run in a 2-step amplification as follows:
1 cycle: 98° C. for 2 minutes;
10 cycles:
  94° C. for 30 seconds;
  70° C. for 2.5 minutes;
20 cycles:
  90° C. for 30 seconds;
  66° C. for 2 minutes;
  70° C. for 2.5 minutes; and
1 cycle: 60° C. for 60 minutes.

Following the amplification reactions, the reactions were cleaned-up using Amicon Ultra 0.5 ml centrifugal filters as follows: 100 ul of each reaction was added to separate filters; the filters were capped, placed in a standard fixed angle rotor and centrifuged at 14,000 g for 10 minutes; 100 ul TE-4 was added to each filter, the filter removed from the microcentrifuge tube and placed upside-down in a new, microcentrifuge tube; the filter was spun at 2000×g for minutes; and the sample collected.

The samples were then prepared to be placed on an ABI 3500×L instrument and spectral calibrations run. The samples were prepared as follows:
1) The oven on the instrument was pre-heated for 30 minutes to 60° C.;
2) The ANYDYE dye set on the instrument was used, but the calibration peak order was changed. The start point was changed to 800;
3) 6-FAM, JOE, ET-TMR, ET-ROX and ET-PBI-3885 were constants in the experiment; ET and non-ET PBI-4686 or PBI-4688 were variables;
4) Into 6 different flip-top tubes containing 500 ul Hi Di formamide, the following was added:
  a) 3.0 ul diluted 6-FAM amplicon;
  b) 5.0 ul diluted JOE amplicon;
  c) 5.0 ul diluted ET-TMR amplicon;
  d) 2.0 ul diluted ET-ROX amplicon; and
  e) 5.0 ul diluted ET-PBI-3885 amplicon.

10 ul of one of the variable ET or non-ET PBI-4686 or PBI-4688 was added into one of the 6 different tubes and repeated for each variable, i.e., each of the 6 tubes had a different variable ET or non-ET dye. The samples were vortexed, and 15 ul added into 24 wells of a 96-well plate. The plate was spun and spectral calibrations run.

Figure 2:
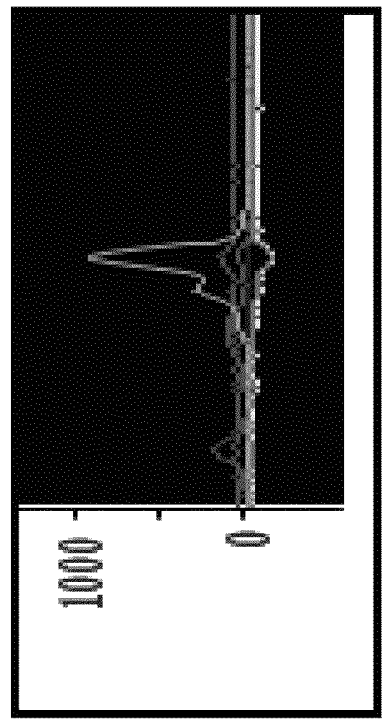
FIG. 2 illustrates a spectral calibration run with PBI-4686 wherein an increase in the donor JOE (green) interfered with the PBI-4686 (orange).
Figure 3:
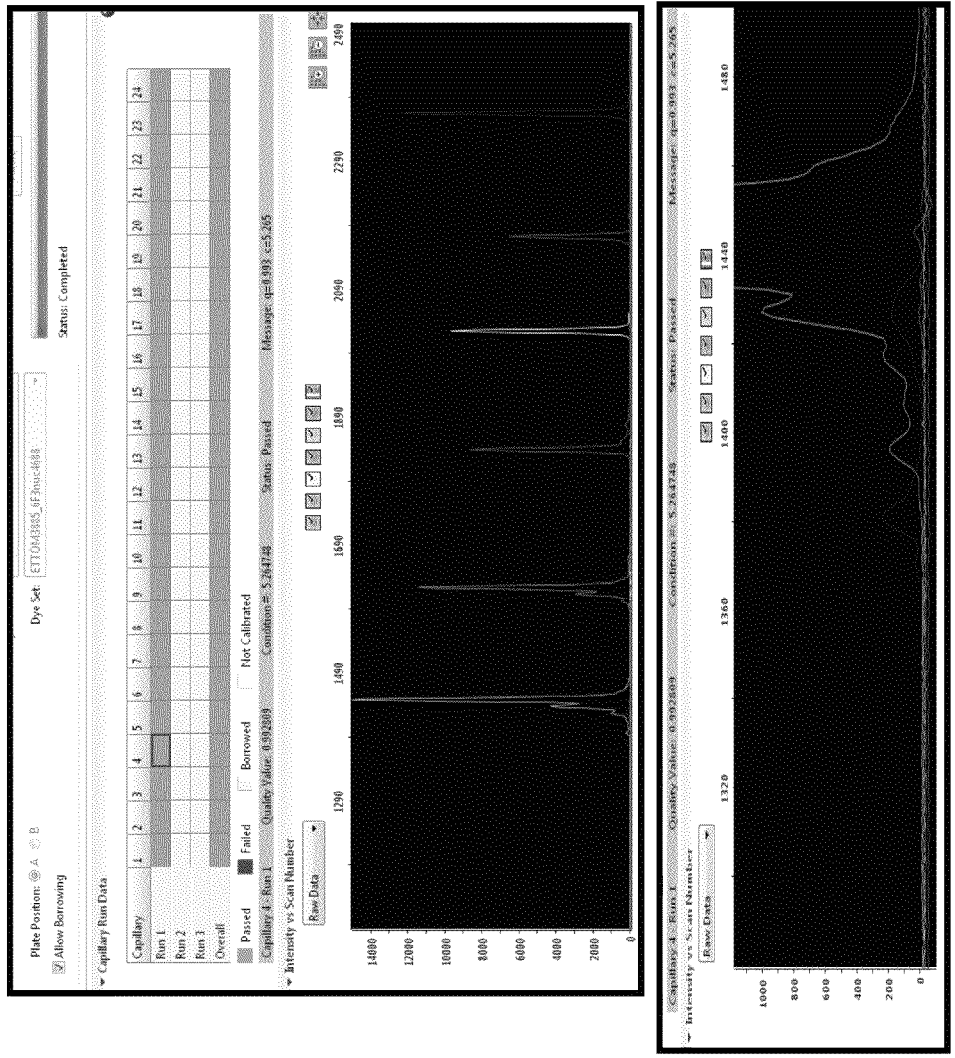
FIG. 3 illustrates a spectral calibration run with PBI-4688 wherein very little JOE (green) interfering with the PBI-4688 (orange), but even less interference of 6-FAM (blue) interfering with the PBI-4688 (orange)
Figure 4:
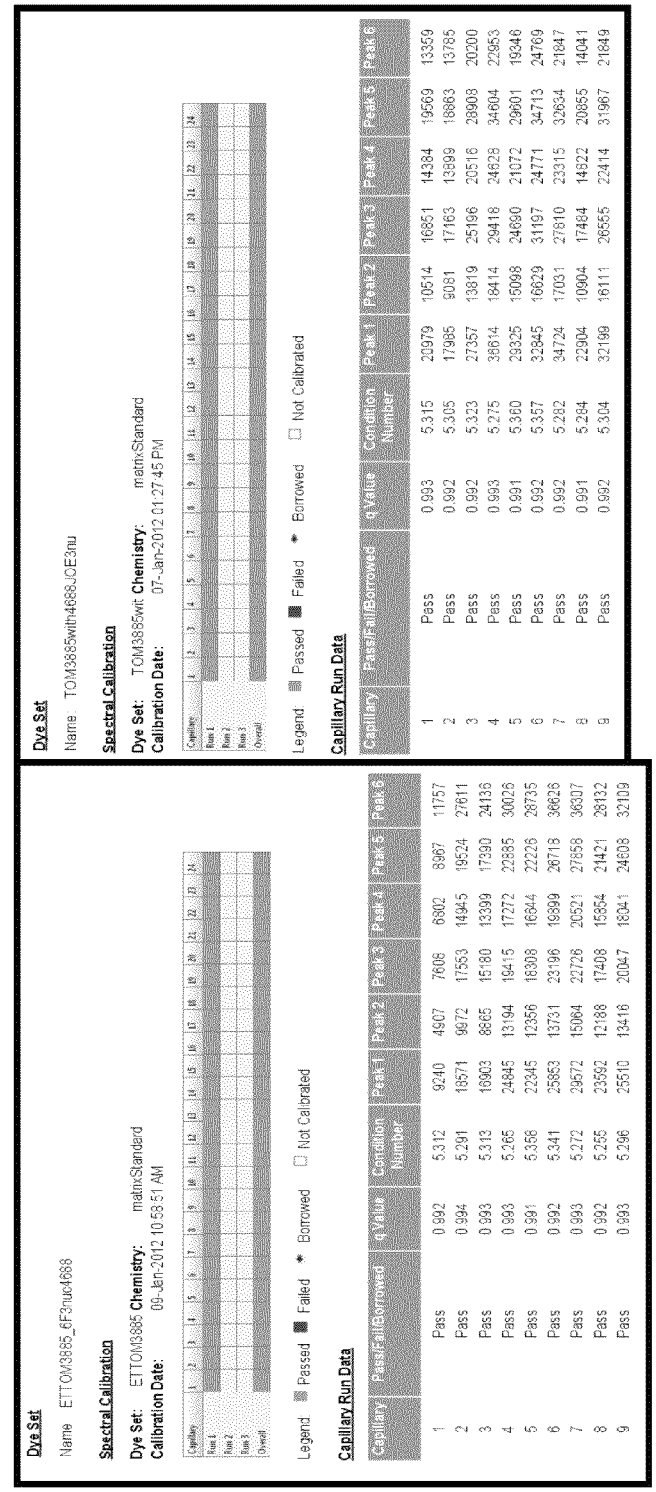
FIG. 4 illustrates a spectral calibration run with PBI-4688 with Q values above 0.99 with oligos that had both JOE and 6-FAM donor dye and 3 nucleotide spacer.

FIGS. 1-4 illustrate the results of the spectral calibration runs. An acceptable spectral calibration must have a minimum of a 0.95 Q value, and the closer to 0.99, the better. PBI-4686 had an excellent Q value of 0.99 (FIG. 1), but had an increase in the donor JOE green interfering with the PBI-4686 orange (FIG. 2). PBI-4688 had Q values above 0.99 (FIG. 4) with oligos that had both JOE and 6-FAM donor dye and 3 nucleotide spacer. There was also very little JOE green interfering with the PBI-4688 orange, but even less interference of 6-FAM blue interfering with the PBI-4688 orange (FIG. 3).

Example 6

Stability of the Internal Lane Standard for Multiplex PCR of STRs Using a Dye of the Present Invention Experiments were conducted during development of embodiments of the present invention to determine the stability of exemplary dye PBI-4688 for potential use in an internal lane standard for use in multiplex PCR of STRs (short tandem repeats).

Oligonucleotides (oligos) were made as energy transfer (ET) oligos for use with JOE or 6-FAM donor dye using the dye PBI-4688. The oligos were made with either a 3 nucleotide spacer (JOE and 6-FAM donor dye or a 5 nucleotide spacer (JOE donor dye).

The following amplification reaction conditions were used for each reaction:
Nanopure water: 91 ul
25×SSB Buffer: 4.0 ul
100 uM Labeled Oligo: 1.0 ul
100 uM Unlabeled Oligo: 1.0 ul
Taq DNA Polymerase (5 U/ul): 2.5 ul.

The reaction mix was vortexed and dispensed into wells of a 96-well plate. 50 ng (0.5 ul) of variable plasmid DNA was then added to each well. Each well contained a different plasmid size. The plasmids are added, separately, to get a range of sizes for an accurate evaluation on the dyes on CE instruments.

The reactions were run in a 2-step amplification as follows:
1 cycle: 98° C. for 2 minutes;
10 cycles:
  97° C. for 1 minute;
  66° C. for 2 minutes;
  72° C. for 1 minutes;
20 cycles:
  92° C. for 1 minute;
  66° C. for 2 minutes;
  72° C. for 1 minute; and
1 cycle: 60° C. for 60 minutes.

Following the amplification reactions, the reactions were cleaned-up using Amicon Ultra 0.5 ml centrifugal filters as follows: 100 ul of each reaction was added to separate filters; the filters were capped, placed in a standard fixed angle rotor and centrifuged at 14,000 g for 10 minutes; 100 ul of either 10 mM MOPS/0.1 mM EDTA, pH 7.4 or 0.1 mM EDTA, pH 8.0 was added to each filter, the filter removed from the microcentrifuge tube and placed upside-down in a new, microcentrifuge tube; the filter was spun at 2000×g for 5 minutes; and the sample collected.

The amplification reactions were then diluted 1:100 in either 10 Mm MOPS/0.1 mM EDTA, pH 7.4 or 0.1 mM EDTA, pH 8.0 and all samples stored at 4° C. except for 1 set of samples for which a single freeze/thaw was performed.

The samples were then prepared to be placed on an ABI 3500×L instrument using a 1.2 kV, 12 sec injection. The dye set G5 was used according to manufacturer's protocol (Promega Corp). The spectral calibration, with a current ABI 3130 5-dye matrix kit was already set on the instrument.

Figure 5:
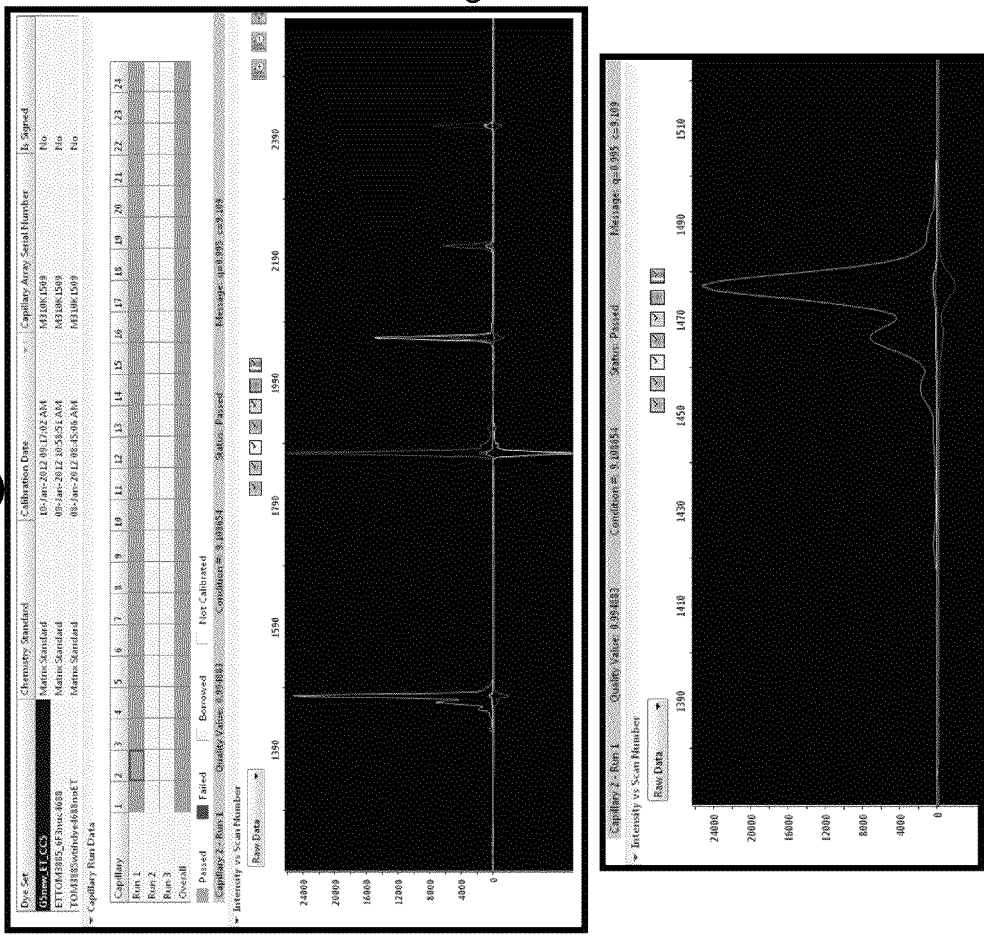
FIG. 5 shows a Raw Data image (top panel) of the various dye-labeled amplicons from a 3500×L spectral calibration on the G5 dye set. The orange peak in the spectral calibration is 6FAM+PBI-4688 and is the close-up image of the bottom panel. This peak is typically represented by the CC5 dye labeled amplicon.

In FIG. 5, the top panel provides a Raw Data image of the various dye-labeled amplicons from a 3500×L spectral calibration on the G5 dye set. The orange peak in the spectral calibration is 6FAM+PBI-4688 and is the close-up image in the bottom panel. This peak is typically represented by the CC5 dye labeled amplicon.

Figure 6:
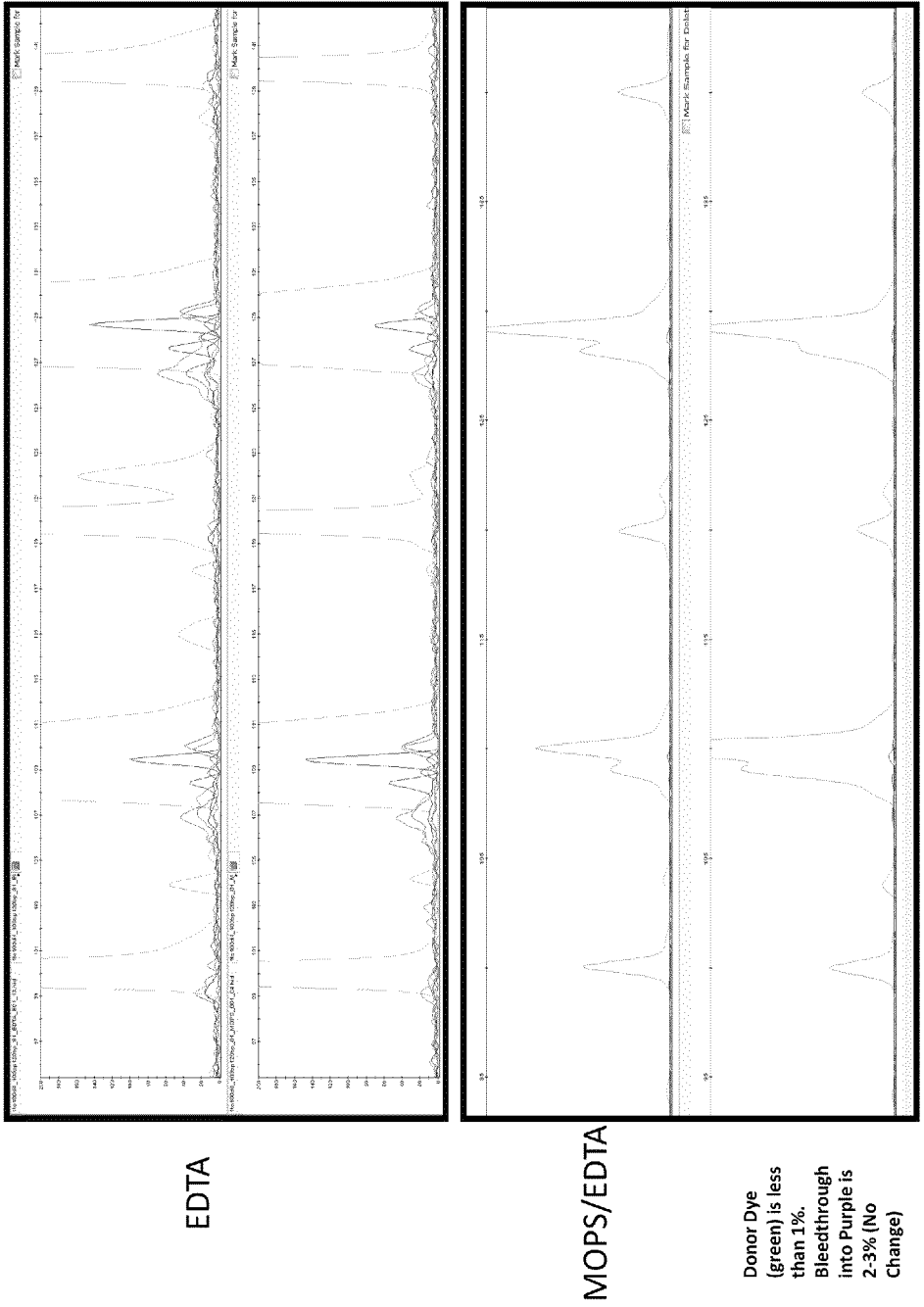
FIG. 6 shows amplicons from the Dyomics 485×L C6 SE-TT-PBI-4688dU PBI AM oligonucleotide that had been buffer exchanged into water and EDTA.

In FIG. 6, the top image in each panel, with the purple under the orange, represents amplicons from the Dyomics 485×L C6 SE-TT-PBI-4688-dU PBI AM oligo that had been buffer exchanged into water and EDTA. The bottom image in each panel, with the purple under the orange, represents amplicons from the Dyomics 485×L C6 SE-TT-PBI-4688-dU PBI AM oligo that had been buffer exchanged into MOPS and EDTA. The top panel is a close-up image of the bottom panel. The orange peaks without purple under them are from the CC5 ILS 500 (Internal Lane Standard, Promega Corporation). Percent bleedthrough and donor dye were evaluated on the ANYDYE dye set (6-dye).

Figure 7:
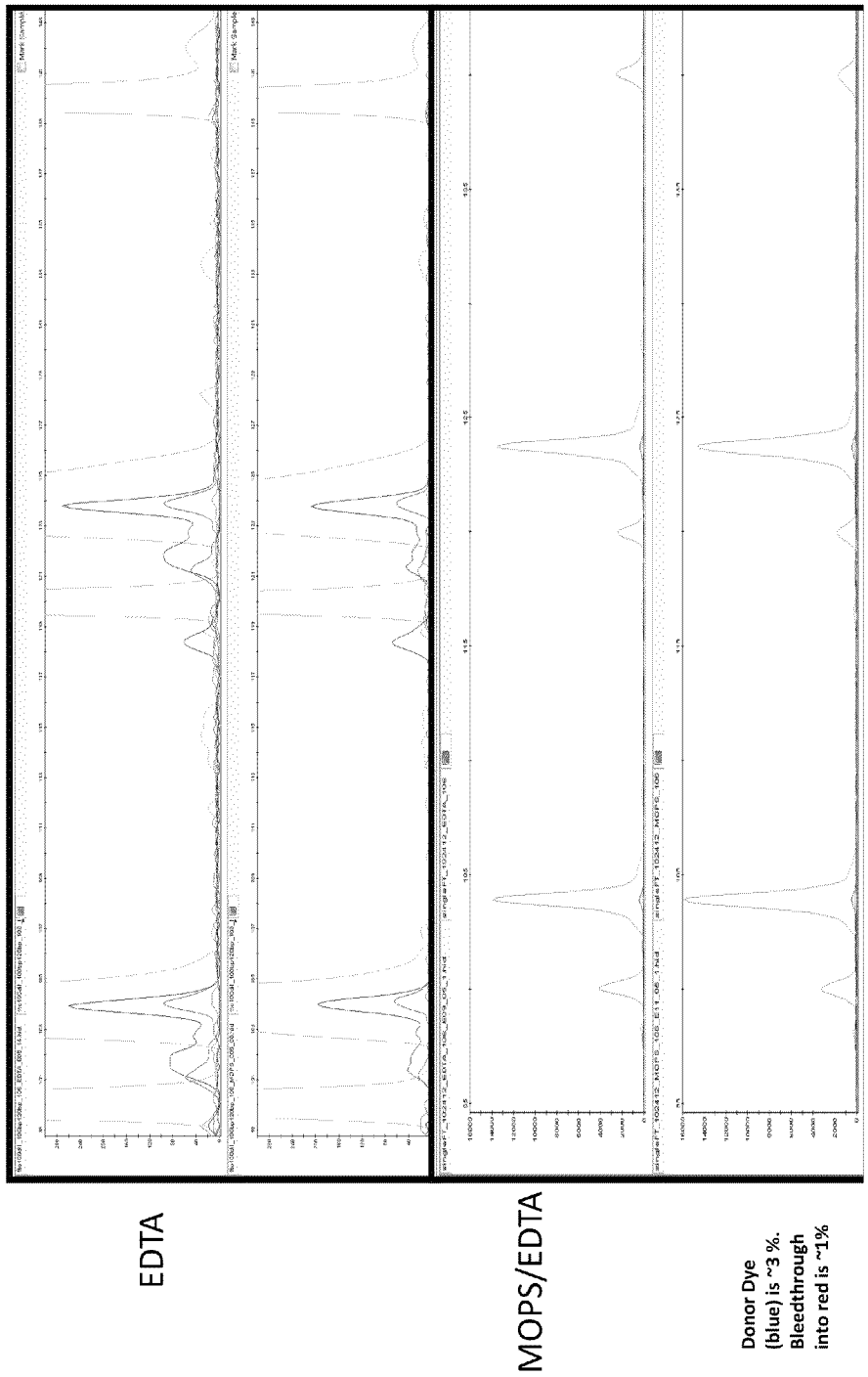
FIG. 7 shows amplicons from the 6FAM C6 AM-TT-PBI-4688dY PBI AM (ultra pure) oligonucleotide that had been buffer exchanged into water and EDTA.

In FIG. 7, the top image in each panel, with the blue under the orange, represents amplicons from the 6FAM C6 AM-TT-PBI-4688-dU PBI AM (ultra pure) oligo that had been buffer exchanged into water and EDTA. The bottom image in each panel, with the blue under the orange, represents amplicons from the 6FAM C6 AM-TT-PBI-4688-dU PBI AM (ultra pure) oligo that had been buffer exchanged into MOPS and EDTA. The top panel is a close-up image of the bottom panel. The orange peaks without blue under them are from the CC5 ILS 500 (Internal Lane Standard, Promega Corporation). Percent bleedthrough and donor dye were evaluated on the ANYDYE dye set (6-dye).

Figure 8:
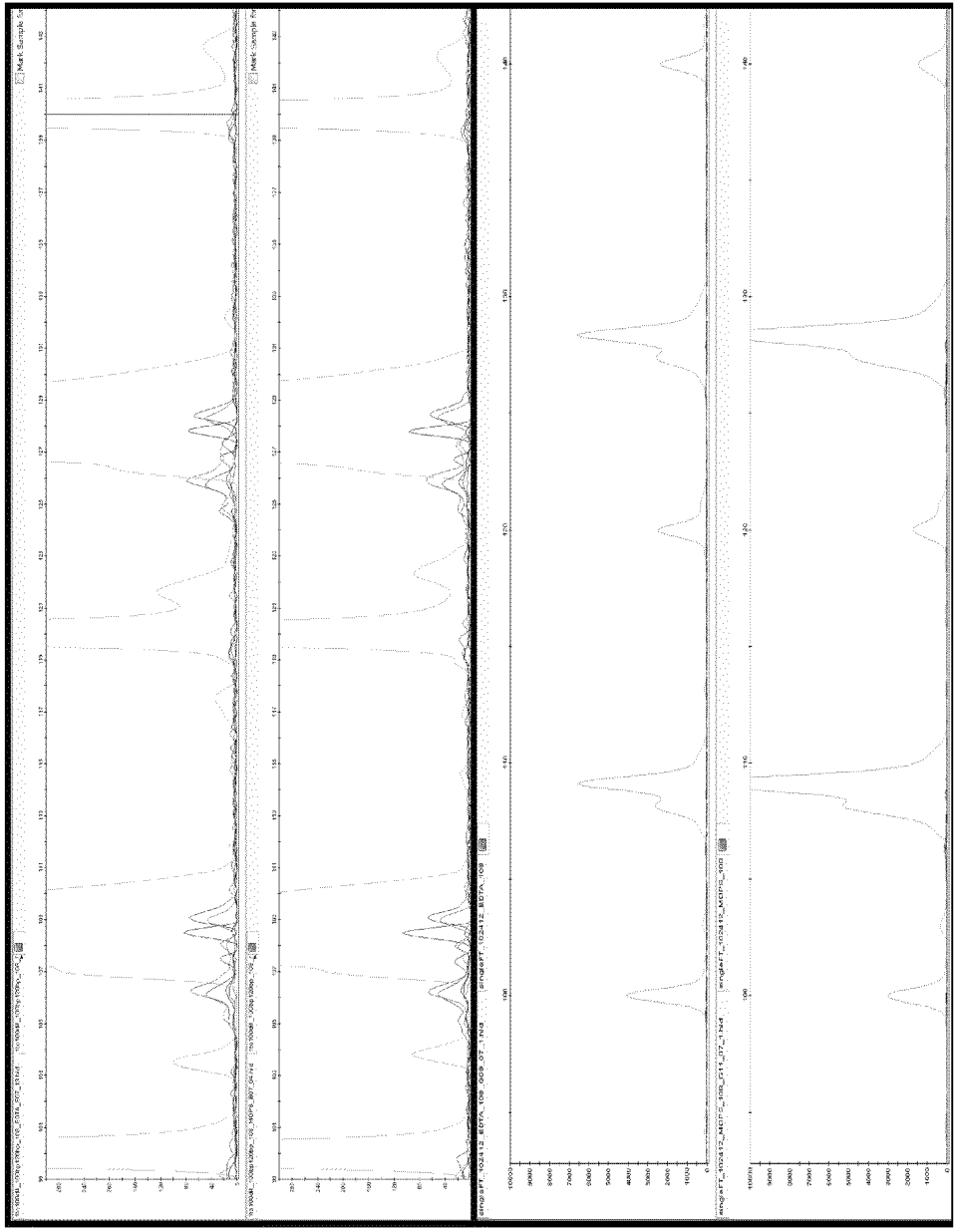
FIG. 8 shows amplicons from the Dyomics 485×L C6 SE-TT-PBI-4770 dU PBI AM oligonucleotide that had been buffer exchanged into water and EDTA.

In FIG. 8, the top image in each panel, with the purple and red under the orange, represents amplicons from the Dyomics 485×L C6 SE-TT-PBI-4770-dU PBI AM oligo that had been buffer exchanged into water and EDTA. The bottom image in each panel, with the purple and red under the orange, represents amplicons from Dyomics 485×L C6 SE-TT-PBI-4770-dU PBI AM oligo that had been buffer exchanged into MOPS and EDTA. The top panel is a close-up image of the bottom panel. The orange peaks without purple and red under them are from the CC5 ILS 500 (Internal Lane Standard, Promega Corporation). Percent bleedthrough and donor dye were evaluated on the ANYDYE dye set (6-dye).

Example 7

Absorption and Emission of Dyes

Si- and Ge-dyes were dissolved in DMSO and diluted in TE-4, pH 7.5 buffer. The absorbance and emission spectra were recorded on Beckman Du 640 spectrometer and Hriba Jobin Yvon Fluorolog, respectively. The fluorescence quantum yields for the dyes with maximal emission around ~660 nm were calculated by using Cy-5 as a standard with quantum yield $\Phi_0$ 0.4 after correcting emission area and absorbance intensity at the excited wavelength by the following equation. The quantum yields of other dyes were obtained by using the standard dyes with similar absorbance and emission spectra. (See FIG. 12).

$$\Phi_{unknown} = \Phi_0 \frac{\text{Emisson Area (unknown)} \times \text{Absorbance Intensity (Standard)}}{\text{Emisson Area (Standard)} \times \text{Absorbance Intensity (unknown)}}$$

Example 8

Stability of the Internal Lane Standard for Multiplex PCR of STRs Using a Dye of the Present Invention Experiments were conducted during development of embodiments of the present invention to determine the stability of exemplary dye PBI-4688 (WZ88) for potential use in an internal lane standard (ILS) for use in multiplex PCR of STRs (short tandem repeats). Oligonucleotides (oligos) were made as energy transfer (ET) oligos for use with TMR or CC3 donor dye using the dye PBI-4688. The oligos were made with a 4 nucleotide spacer (TTTT) to yield 6-TMR-TTTT-WZ88 ILS and CC3-TTTT-WZ88 ILS.

The two ILS samples were stored in a clear tube by the window, in the sun for approximately two days in order to observe, side by side, the integrity of the respective dyes. Two sets of 6-TMR-TTTT-WZ88 ILS and CC3-TTTT-WZ88 ILS samples were exposed to the sun. Each set consisted of an undiluted ILS sample and a diluted (1 to 40 in TE-4) ILS sample. Prior to putting the samples on the 3500 CE device (Applied Biosystems), the undiluted ILS samples were diluted 1 to 40 in TE-4. The control was stored undiluted in an amber tube at 4° C.

1 µl of ILS sample +10 µl of formamide was added to each well of a 96 well assay plate. The samples were then heat denatured for 3 minutes and put on ice for another 3 minutes. The samples were then put on the 3500 CE and analyzed.

As FIGS. 14-25 demonstrate, CC3-TTTT-WZ88 ILS overall had higher peak heights than the 6TMR-TTTT-WZ88 ILS. The CC3-TTTT-WZ88 ILS and the 6-TMR-TTTT-WZ88 ILS demonstrated approximately a 30% loss in peak height after approximately 2 days in the sun when stored in a clear tube. The 6-TMR-TTTT-WZ88 ILS appeared to have a greater percentage of black into orange, ranging from approximately 9.3%, with the diluted sample to approximately 16% with the undiluted sample. The percentage of black into orange for the CC3-TTTT-WZ88 ILS ranged from approximately 2.0% with the diluted sample to approximately 3.5% with the undiluted sample. The CC3-TTTT-WZ88 ILS demonstrated a higher percentage of bleedthrough of purple into orange than the 6TMR TTTT WZ88 ILS.

Example 9

Stability of the Internal Lane Standard for Multiplex PCR of STRs Using a Dye of the Present Invention Experiments were conducted during development of embodiments of the present invention to determine the stability of exemplary dye PBI-4688 (WZ88) for potential use in an internal lane standard (ILS) for use in multiplex PCR of STRs (short tandem repeats). Oligonucleotides (oligos) were made as energy transfer (ET) oligos for use with TMR or CC3 donor dye using the dye PBI-4688. The oligos were made with a 4 nucleotide spacer (TTTT) to yield 6-TMR-TTTT-WZ88 ILS and CC3-TTTT-WZ88 ILS.

The 6-TMR-TTTT-WZ88 ILS and CC3-TTTT-WZ88 ILS were put through 1 or 10 freeze (−20° C.)-thaw (RT) cycles in order to observe, side by side, the integrity of the respective dyes.

Two sets of 6-TMR-TTTT-WZ88 and CC3-TTTT-WZ88 ILS samples were put through 1 or 10 freeze (−20° C.) thaw (RT) cycles. Each set consisted of an undiluted ILS sample and a diluted (1 to 40 in TE-4) ILS sample. Prior to putting the samples on the 3500 CE, the undiluted ILS samples were diluted 1 to 40 in TE-4. All samples tested were put in amber tubes. The control was stored undiluted in an amber tube at 4° C.

1 µl of ILS sample +10 µl of formamide was added to each well of a 96-well assay plate. The samples were then heat denatured for 3 minutes and put on ice for another 3 minutes. The samples were then put on the 3500 CE.

As FIGS. 26-37 demonstrate, the CC3-TTTT-WZ88 ILS overall had higher peak heights than the 6-TMR-TTTT-WZ88 ILS. There was no significant loss in peak height for the CC3-TTTT-WZ88 ILS or the 6-TMR TTTT-WZ88 ILS after 1 or 10 freeze-thaw cycles. Both the diluted sample and undiluted sample of CC3-TTTT-WZ88 ILS showed approximately 2% black into orange after 1 or 10 freeze-thaw cycles. The 6-TMR-TTTT WZ88 ILS showed an approximately 2% or 3% black into orange after 1 or 10 freeze-thaw cycles, respectively, with the diluted sample and approximately 2% with the undiluted sample after 1 or 10 freeze-thaw cycles. The CC3-TTTT-WZ88 ILS demonstrated approximately 2.7% of bleedthrough of purple into orange in the diluted and undiluted samples after 1 or 10 freeze-thaw cycles, where the 6-TMR-TTTT WZ88 ILS showed approximately 2% of bleedthrough of purple into orange in either diluted or undiluted samples after 1 or 10 freeze-thaw cycles.

Various features and advantages of the invention are set forth in the following claims.

What is claimed is:

1. A method of detecting the presence of a nucleic acid polymer in a sample comprising:
    a) contacting a sample suspected of containing a nucleic acid polymer with a composition comprising a conjugate comprising a compound of Formula (I) and an oligonucleotide; and
    b) detecting the presence or amount of the compound in the sample;
    wherein the compound of formula (I) is a component in an ET cassette; and
    wherein the compound of formula (I) is as shown below:

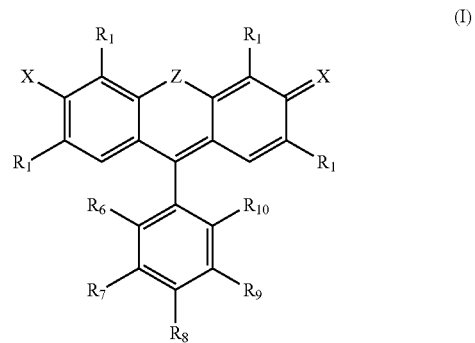

(I)

wherein
    Z is $Si(R_{11})(R_{12})$ or $Ge(R_{11})(R_{12})$;
    each $R_{11}$ and $R_{12}$ are independently selected from $C_{1-10}$ linear, branched or cyclic alkyl, $C_{1-10}$ alkyl interrupted with one or more heteroatoms, $C_{6-10}$ aryl, heteroaryl or $R_{11}$ and $R_{12}$ may together form a ring;
    each X is independently selected from $OR_2$ or $N(R_3)(R_4)$;
    each $R_1$ is independently selected from H, $C_{1-4}$ alkyl, sulfonate or halo;
    $R_2$ is H, $C_{1-10}$ alkyl, L-R or L-$C_S$;
    $R_3$ and $R_4$ are independently selected from H, $C_{1-4}$ alkyl, $C_{1-4}$ alkyl interrupted with one or more heteroatoms, $C_{6-10}$ aryl, peptidyl, heteroaryl, L-R or L-$C_S$;
    $R_{6-10}$ are independently H, halo, alkoxy, amino, alkyl, aryl, heteroaryl, $CO_2H$, $SO_3H$, L-$CO_2H$, L-$SO_3H$, L-R or L-$C_S$;
    L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;
    R is a reactive group; or
    $C_S$ is a conjugated substance;
    one or more of $R_3$ and $R_4$ or $R_3$ and $R_1$ or $R_4$ and $R_1$ may together form a ring;
    and
    one or more of $R_{6-10}$ may together form a ring.

2. The method of claim 1, wherein more than one nucleic acid polymer is detected in a single reaction.

3. A method of detecting the presence of a nucleic acid polymer in a sample comprising:
    a) contacting a sample suspected of containing a nucleic acid polymer with a composition comprising a conjugate comprising a compound of Formula (II) and an oligonucleotide; and b) detecting the presence or amount of the compound in the sample;

wherein the compound of formula (II) is a component in an ET cassette; and wherein the compound of formula (II) is as shown below:

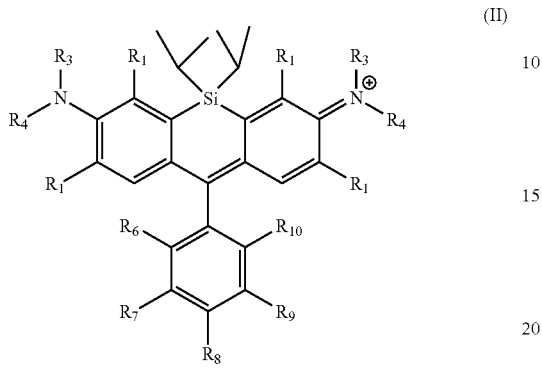

(II)

wherein each $R_1$ is independently selected from H, $C_{1-4}$ alkyl, sulfonate or halo;

$R_3$ and $R_4$ are independently selected from H, $C_{1-4}$ alkyl, $C_{1-4}$ alkyl interrupted with one or more heteroatoms, L-R or L-$C_S$;

$R_{6-9}$ are independently H, halo, alkyl, aryl, heteroaryl, $CO_2H$, $SO_3H$, L-$CO_2H$, L-$SO_3H$, L-R or L-$C_S$;

$R_{10}$ is alkoxy, alkyl, aryl, heteroaryl, $CO_2H$, $SO_3H$, $SO_2N(R_N)_2$, $CON(R_N)_2$, L-$CO_2H$, L-$SO_3H$, L-R or L-$C_S$;

each $R_N$ is independently selected from H, alkyl, aryl, heteroaryl, L-R, and L-$C_S$ L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group; or $C_S$ is a conjugated substance;

one or more of $R_3$ and $R_4$ or $R_3$ and $R_1$ or $R_4$ and $R_1$ may together form a ring;

and one or more of $R_{6-9}$ may together form a ring.

4. The method of claim 3, wherein more than one nucleic acid polymer is detected in a single reaction.

5. A compound selected from the group consisting of:

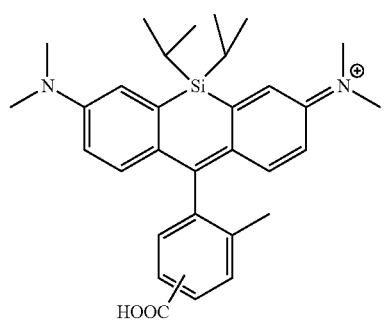

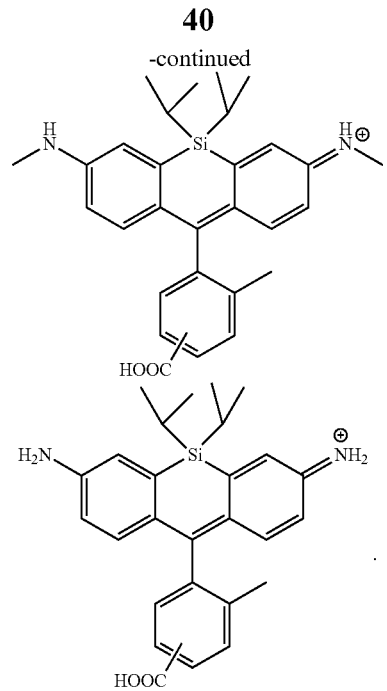

6. A kit comprising a compound according to formula (I) or (II) in an ET cassette, at least one locus-specific primer, and instructions for use; wherein the compound of formula (I) is

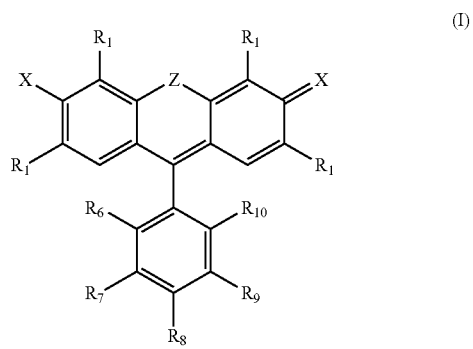

(I)

wherein

Z is $Si(R_{11})(R_{12})$ or $Ge(R_{11})(R_{12})$;

each $R_{11}$ and $R_{12}$ are independently selected from $C_{1-10}$ linear, branched or cyclic alkyl, $C_{1-10}$ alkyl interrupted with one or more heteroatoms, $C_{6-10}$ aryl, heteroaryl or $R_{11}$ and $R_{12}$ may together form a ring;

each X is independently selected from $OR_2$ or $N(R_3)(R_4)$;

each $R_1$ is independently selected from H, $C_{1-4}$ alkyl, sulfonate or halo;

$R_2$ is H, $C_{1-10}$ alkyl, L-R or L-$C_S$;

$R_3$ and $R_4$ are independently selected from H, $C_{1-4}$ alkyl, $C_{1-4}$ alkyl interrupted with one or more heteroatoms, $C_{6-10}$ aryl, peptidyl, heteroaryl, L-R or L-$C_S$;

$R_{6-10}$ are independently H, halo, alkoxy, amino, alkyl, aryl, heteroaryl, $CO_2H$, $SO_3H$, L-$CO_2H$, L-$SO_3H$, L-R or L-$C_S$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group; or
$C_S$ is a conjugated substance;
one or more of $R_3$ and $R_4$ or $R_3$ and $R_1$ or $R_4$ and $R_1$ may together form a ring;
and
one or more of $R_{6-10}$ may together form a ring;
and wherein the compound of formula (II) is

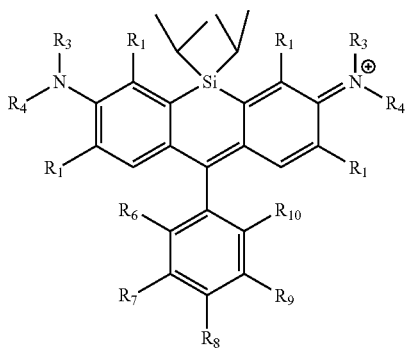

(II)

wherein
each $R_1$ is independently selected from H, $C_{1-4}$ alkyl, sulfonate or halo;
$R_3$ and $R_4$ are independently selected from H, $C_{1-4}$ alkyl, $C_{1-4}$ alkyl interrupted with one or more heteroatoms, L-R or L-$C_S$;
$R_{6-9}$ are independently H, halo, alkyl, aryl, heteroaryl, $CO_2H$, $SO_3H$, L-$CO_2H$, L-$SO_3H$, L-R or L-$C_S$;
$R_{10}$ is alkoxy, alkyl, aryl, heteroaryl, $CO_2H$, $SO_3H$, $SO_2N(R_N)_2$, $CON(R_N)_2$, L-$CO_2H$, L-$SO_3H$, L-R or L-$C_S$;
each $R_N$ is independently selected from H, alkyl, aryl, heteroaryl, L-R, and L-$C_S$
L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;
R is a reactive group; or
$C_S$ is a conjugated substance;
one or more of $R_3$ and $R_4$ or $R_3$ and $R_1$ or $R_4$ and $R_1$ may together form a ring;
and
one or more of $R_{6-9}$ may together form a ring.

* * * * *